(12) United States Patent
Kawanishi et al.

(10) Patent No.: US 8,969,376 B2
(45) Date of Patent: Mar. 3, 2015

(54) PYRAZOLOPYRIMIDINE COMPOUNDS AND THEIR USE AS PDE10 INHIBITORS

(75) Inventors: Eiji Kawanishi, Osaka (JP); Mitsuya Hongu, Osaka (JP); Yoshihito Tanaka, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 45 days.

(21) Appl. No.: 13/579,095

(22) PCT Filed: Feb. 25, 2011

(86) PCT No.: PCT/JP2011/054997
§ 371 (c)(1),
(2), (4) Date: Aug. 15, 2012

(87) PCT Pub. No.: WO2011/105628
PCT Pub. Date: Sep. 1, 2011

(65) Prior Publication Data
US 2012/0309754 A1 Dec. 6, 2012

Related U.S. Application Data

(60) Provisional application No. 61/308,706, filed on Feb. 26, 2010.

(51) Int. Cl.
*A61K 31/415* (2006.01)
*C07D 293/00* (2006.01)
*C07D 487/00* (2006.01)
*C07D 487/04* (2006.01)

(52) U.S. Cl.
CPC .................................... *C07D 487/04* (2013.01)
USPC ......... 514/303; 514/403; 548/121; 548/360.1

(58) Field of Classification Search
USPC ........................ 514/303, 403; 548/121, 360.1
See application file for complete search history.

(56) References Cited

U.S. PATENT DOCUMENTS

| | | | |
|---|---|---|---|
| 4,093,617 | A | 6/1978 | Robins et al. |
| 5,294,612 | A | 3/1994 | Bacon et al. |
| 5,459,145 | A | 10/1995 | Saccomano et al. |
| 2004/0249148 | A1 | 12/2004 | Erguden et al. |
| 2007/0112006 | A1 | 5/2007 | Schiemann et al. |

FOREIGN PATENT DOCUMENTS

| | | | |
|---|---|---|---|
| EP | 0 531 901 A2 | | 3/1993 |
| EP | 1 250 923 A2 | | 10/2002 |
| WO | WO 03/000693 A1 | | 1/2003 |
| WO | WO 03/014117 A1 | | 2/2003 |
| WO | WO 03/101993 A1 | | 12/2003 |
| WO | WO 2004/022560 A1 | | 3/2004 |
| WO | WO 2005/012485 A2 | | 2/2005 |
| WO | WO 2005/054246 A2 | | 6/2005 |
| WO | WO 2005/082883 A2 | | 9/2005 |
| WO | WO 2005/120514 A1 | | 12/2005 |
| WO | WO 2006/071988 A1 | | 7/2006 |
| WO | WO 2006/072828 A2 | | 7/2006 |
| WO | WO 2007/076055 A2 | | 7/2007 |

OTHER PUBLICATIONS

Francis et al., "Cyclic Nucleotide Phosphodiesterases: Relating Structure and Function", Prog. Nucleic Acid Res., 2001, vol. 65, pp. 1-52.
Fujishige et al., "Cloning and Characterization of a Novel Human Phosphodiesterase That Hydrolyzes Both cAMP and cGMP (PDE10A)", The Journal of Biological Chemistry, Jun. 25, 1999, vol. 274, No. 26, pp. 18438-18445.
Ghozlan et al., "β-Amino-β-(pyrid-4-yl)acrylonitrile in heterocyclic synthesis: synthesis of some new pyridine, pyridone, pyrazole, thiophene, fused pyrimidine and triazine derivatives", Tetrahedron, 2002, vol. 58, No. 46, pp. 9423-9429.
International Search Report, issued in PCT/JP2011/054997, dated Apr. 5, 2011.
Kotera et al., "Characterization and Phosphorylation of PDE10A2, a Novel Alternative Splice Variant of Human Phosphodiesterase That Hydrolyzes cAMP and cGMP", Biochemical and Biophysical Research Communications, 1999, vol. 261, pp. 551-557.
Loughney et al., "Isolation and characterization of PDE10A, a novel human 3',5'cyclic nucleotide phosphodiesterase", Gene, 1999, vol. 234, pp. 109-117.
Menniti et al., "Phosphodiesterase 10A inhibitors: A novel approach to the treatment of the symptoms of schizophrenia", Current Opinion in Investigational Drugs, 2007, vol. 8, No. 1, pp. 54-59.
Novinson et al., "Adenosine Cyclic 3', 5'-Monophosphate Phosphodiesterase Inhibitors. 2. 3-Substituted 5,7-Dialkylpyrazolo[1,5-a]pyrimidines", Journal of Medicinal Chemistry, 1975, vol. 18, No. 5, pp. 460-464.

(Continued)

*Primary Examiner* — Jeffrey H Murray
*Assistant Examiner* — Oluwafemi Masha
(74) *Attorney, Agent, or Firm* — Birch, Stewart, Kolasch & Birch, LLP

(57) ABSTRACT

The present invention relates to a compound represented by formula [I]:

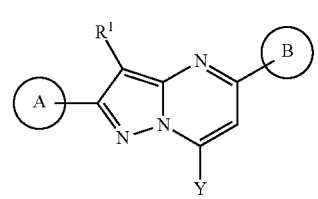

wherein:
$R^1$ is hydrogen, halogen, lower alkyl or cyano;
Ring A is an optionally substituted heterocyclic group;
Ring B is an optionally substituted 3 to 6-membered monocyclic group; and
Y is optionally substituted amino, optionally substituted cyclic amino, optionally substituted aliphatic 3 to 6-membered monocycylyloxy, optionally substituted lower alkyl or optionally substituted lower alkyl-O—,
or a pharmaceutically acceptable salt thereof, and to their use as PDE10 inhibitor.

14 Claims, No Drawings

(56) References Cited

OTHER PUBLICATIONS

Soderling at al., "Isolation and characterization of a dual-substrate phosphodiesterase gene family: PDE10A", Proc. Natl. Acad. Sci. USA, Jun. 1999, vol. 96, pp. 7071-7076.

Springer et al., "Synthesis and Enzymic Activity of 6-Carbethoxy- and 6-Ethoxy-3,7-disubstituted-pyrazolo[1,5-a]pyrimidines and Related Derivatives as Adenosine Cyclic 3',5'-Phosphate Phosphodiesterase Inhibitors", J. of Medicinal Chemistry, 1982, vol. 25, No. 3, pp. 235-242.

Extended European Search Report for European Application No. 11747579.8, dated Jul. 16, 2013.

PYRAZOLOPYRIMIDINE COMPOUNDS AND THEIR USE AS PDE10 INHIBITORS

CROSS REFERENCED TO RELATED APPLICATIONS

This application is the National Phase of PCT/JP2011/054997 filed on Feb. 25, 2011, which claims priority under 35 U.S.C. 119(e) to U.S. Provisional Application No. 61/308,706 filed on Feb. 26, 2010, all of which are hereby expressly incorporated by reference into the present application.

TECHNICAL FIELD

The present invention relates to novel pyrazolopyrimidine compounds having an excellent phosphodiesterase 10 (PDE10) inhibitory activity and useful as pharmaceuticals, and to processes for preparing such compounds and to their use.

BACKGROUND ART

Cyclic nucleotide phosphodiesterase (hereinafter referred to as phosphodiesterase or PDE) is an enzyme that hydrolyses a phosphodiester bond in cyclic nucleotides such as cAMP (adenosine 3',5'-cyclic monophosphate) or cGMP (guanosine 3',5'-cyclic monophosphate), etc. as a substrate, to provide nucleotides such as 5'AMP (adenosine 5'-monophosphate) or 5'GMP (guanosine 5'-monophosphate), etc.

Cyclic nucleotides such as cAMP and cGMP are involved in the regulation of many functions within a living body as second messengers of intracellular signaling. Intracellular concentrations of cAMP and cGMP, which vary in response to extracellular signals, are regulated by a balance between enzymes involved in synthesis of cAMP and cGMP (adenylate cyclase and guanylate cyclase) and PDE involved in hydrolysis of such enzymes.

For PDE of mammals, many kinds of PDEs have been isolated and identified in mammals so far, and they have been classified into plural families in accordance with amino-acid sequence homology, biochemical properties, characterization by inhibitors and the like (Francis et al., Prog. Nucleic Acid Res., vol. 65, pp. 1-52, 2001).

Among such various families of PDEs of mammals, phosphodiesterase 10 (PDE10) [more specifically phosphodiesterase 10A (PDE10A)] recognizes both cAMP and cGMP as a substrate. It has been reported that PDE10 has a greater affinity for cAMP. Further, cDNAs of human, mouse and rat PDE10As have been isolated and identified. Furthermore, the existence of PDE10 proteins has been confirmed. (Fujishige et al., J. Biol. Chem., vol. 274, pp. 18438-18445, 1999; Kotera et al., Biochem. Biophys. Res. Commun., vol. 261, pp. 551-557, 1999; Soderling et al., Proc. Natl. Acad. Sci. USA, vol. 96, pp. 7071-7076, 1999; and Loughley et al., Gene, vol. 234, pp. 109-117, 1999).

Regarding PDE10 inhibitory compounds (PDE10 inhibitors), that is, compounds having inhibitory action on the enzyme activity of PDE10, the following have been reported:

For example, in EP1250923 (Pfizer) and WO2005/082883 (Pfizer), papaverine and various aromatic heterocyclic compounds such as quinazoline and isoquinazoline compounds are disclosed as PDE10 inhibitors.

It also has been disclosed therein that PDE10 inhibitors are useful for the treatment or prophylaxis of diseases or conditions such as:

Psychotic Disorder:
for example, schizophrenia, schizophreniform disorder, delusional disorder, schizoaffective disorder, substance-induced psychotic disorder, paranoid or schizoid personality disorder, etc;

Anxiety Disorder:
for example, panic disorder, agoraphobia, specific phobia, social phobia, obsessive-compulsive disorder, post-traumatic stress disorder, acute stress disorder, generalized anxiety disorder, etc;

Movement Disorder:
for example, Huntington's disease, dyskinesia associated with dopamine agonist therapy, Parkinson's disease, restless leg syndrome, etc;

Drug Addiction:
for example, addiction to alcohol, amphetamine, cocaine, or opiate, etc;

Disorders Comprising Deficient Cognition as a Symptom:
for example, dementia (including Alzheimer's disease, multi-infarct dementia, etc), delirium, amnestic disorder, post-traumatic stress disorder, mental retardation, a learning disorder, attention deficit hyperactivity disorder (ADHD), age-related cognitive decline, etc; and Mood Disorder:
for example, major depressive disorder, dysthymic disorder, minor depressive disorder, bipolar disorder (including bipolar I disorder, bipolar II disorder), cyclothymic disorder, etc; or Mood Episode:
for example, major depressive episode, manic or mixed episode, hypomanic episode, etc.

Further, it also has been disclosed therein that PDE10 inhibitors are useful for the treatment or prophylaxis of neurodegenerative disorders, for example, Parkinson's disease, and Hungtington's disease, etc.

In the literature of Menniti et al. [Menniti et al., Curr. Opin. Investig. Drugs., 2007, 8(1):54-59], it is disclosed that PDE10 inhibitors have potential as antipsychotic agents along with potential to improve cognitive symptoms in schizophrenia.

WO2003/000693 (Bayer) discloses imidazotriazine compounds as PDE10 inhibitors. It also discloses that PDE10 inhibitors are useful for the treatment or prophylaxis of neurodegenerative disorders, especially for Parkinson's disease.

WO2003/014117 (Bayer) discloses various pyrroloisoquinoline compounds as PDE10 inhibitors. It also discloses that these compounds having inhibitory action on PDE10 activity show antiproliferative activity and are useful for treating cancer. Further, it discloses that those compounds are useful for treating conditions of pain and/or for lowering the temperature of the body in fever condition.

WO2005/12485 (Bayer) discloses that PDE10 inhibitors are useful for stimulating insulin release from pancreatic cells. Further, it is disclosed that PDE10 inhibitors are useful for the treatment or prophylaxis of diabetes and diseases related thereof:

for example, type 1 or type 2 diabetes, maturity-onset diabetes of the young (MODY), latent autoimmune diabetes adult (LADA), impaired glucose tolerance (IGT), impaired fasting glucose (IGF), gestational diabetes, metabolic syndrome X, etc.

See also WO2005/120514 (Pfizer), which discloses PDE10 inhibitors that are said to be useful to decrease body weight and/or body fat in the treatment of obese patients. Further, it is disclosed therein that those PDE10 inhibitors are useful for treatment of non-insulin dependent diabetes (NIDDM), metabolic syndrome and glucose intolerance etc.

Here, with respect to the pyrazolopyrimidine compounds, the following compounds are known.

WO2007/076055 (Entremed Inc.) discloses pyrazolopyrimidine compounds having an action as a proteinase activated receptor antagonist. However, they are clearly different from the compounds of the present invention in terms of their pharmacological action and structure.

DISCLOSURE OF THE INVENTION

The present invention provides novel compounds having an excellent PDE10 inhibitory activity, processes for preparing such compounds, use of the compounds, and pharmaceutical compositions comprising the compounds, and the like.

The inventors of the present invention have found novel pyrazolopyrimidine compounds having an excellent PDE10 inhibitory activity, thereby leading to completion of the invention.

Namely, the present invention relates to a compound represented by formula [I]:

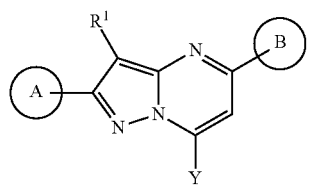

[I]

wherein:
$R^1$ is hydrogen, halogen, lower alkyl or cyano;
Ring A is an optionally substituted heterocyclic group;
Ring B is an optionally substituted 3 to 6-membered monocyclic group; and
Y is optionally substituted amino,
optionally substituted cyclic amino,
optionally substituted aliphatic 3 to 6-membered monocyclyloxy,
optionally substituted lower alkyl or
optionally substituted lower alkyl-O—,
or a pharmaceutically acceptable salt thereof.

Also, the present invention relates to a method for treating or preventing a disease comprising administering to a patient in need thereof an effective amount of the compound of formula [I] or a pharmaceutically acceptable salt thereof.

Further, the present invention relates to a pharmaceutical composition comprising the compound of formula [I] or a pharmaceutically acceptable salt thereof as an active ingredient, as well as to the use of said compound for the manufacture of a medicament.

Furthermore, the present invention relates to a process for preparing the compound of formula [I] or a pharmaceutically acceptable salt thereof.

EFFECT OF THE INVENTION

The compounds of formula [I] or a pharmaceutically acceptable salt thereof according to the present invention has an excellent PDE10 inhibitory activity (that is, inhibitory activity on the enzyme activity of phosphodiesterase 10).

INDUSTRIAL APPLICABILITY

The compounds of the present invention and a pharmaceutical composition containing thereof as an active ingredient are useful for the treatment or prophylaxis of a disease or condition which is expected to be ameliorated by inhibition of PDE10 activity (that is, inhibition on the enzyme activity of phosphodiesterase 10) [for example, schizophrenia, anxiety disorder, drug addiction, a disease comprising as a symptom a deficiency in cognition, mood disorder and mood episode, etc].

BEST MODE FOR CARRYING OUT THE INVENTION

In the present invention, the following terms have the following meanings, unless otherwise indicated.

Lower alkyl, including "lower alkyl" in lower alkyl amino or di-lower alkyl amino and the like, includes a straight or branched group having 1 to 6 carbon atoms ($C_{1-6}$), preferably 1 to 4 carbon atom(s) ($C_{1-4}$). Specifically included in the lower alkyl are methyl, ethyl, propyl, isopropyl, butyl, isobutyl, t-butyl, sec-butyl and the like.

Lower cycloalkyl includes a cyclic group having 3 to 8 carbon atoms ($C_{3-8}$), preferably 3 to 6 carbon atoms ($C_{3-6}$). Also included are ones having 1 to 2 lower alkyl substituent(s) on their cyclic moiety. Specifically included in the lower cycloalkyl are cyclopropyl, cyclobutyl, cyclopentyl, cyclohexyl, cycloheptyl, cyclooctyl and the like.

Lower cycloalkane includes a ring having 3 to 8 carbon atoms ($C_{3-8}$), preferably 3 to 6 carbon atoms ($C_{3-6}$). Also included are ones having 1 to 2 lower alkyl substituent(s) on their cyclic moiety. Specifically included in the lower cycloalkane are cyclopropane, cyclobutane, cyclopentane, cyclohexane, cycloheptane, cyclooctane and the like.

Lower alkoxy includes ones having 1 to 6 carbon atoms ($C_{1-6}$), preferably 1 to 4 carbon atom(s) ($C_{1-4}$). Also included are any of lower alkyl-O— or lower cycloalkyl-O—. Specifically included in the lower alkoxy are methoxy, ethoxy, propoxy, isopropoxy, butoxy, isobutoxy, t-butoxy, sec-butoxy and the like.

Lower alkanoyl includes a straight or branched group having 2 to 7 carbon atoms ($C_{2-7}$), preferably 2 to 5 carbon atoms ($C_{2-5}$). Also included are any of lower alkyl-CO— or lower cycloalkyl-CO—. Specifically included in the lower alkanoyl are formyl, acetyl, propanoyl, butanoyl, isobutanoyl, pivaloyl and the like.

Lower alkylene includes a straight or branched group having 1 to 6 carbon atom(s) ($C_{1-6}$), preferably 1 to 4 carbon atoms ($C_{1-4}$).

Lower alkenyl and lower alkenylene include ones having 2 to 7 carbon atoms ($C_{2-7}$), preferably 2 to 5 carbon atoms ($C_{2-5}$), and at least one double bond.

Lower cycloalkenyl includes a cyclic group having 3 to 8 carbon atoms ($C_{3-8}$), preferably 3 to 6 carbon atoms ($C_{3-6}$). Also included in the lower cycloalkenyl are ones having 1 to 2 lower alkyl substituent(s) on their cyclic moiety.

Halogen includes fluorine, chlorine, bromine or iodine. Halo includes fluoro, chloro, bromo or iodo.

Halo-lower alkyl includes lower alkyl substituted by halogen (usually 1 to 5, preferably 1 to 3). Specifically included in the halo-lower alkyl are fluoroalkyl, difluoroalkyl, trifluoroalkyl, perfluoroalkyl and the like. More specifically included are fluoromethyl, difluoromethyl, trifluoromethyl and the like.

Halo-lower alkoxy includes lower alkoxy substituted with halogen (usually 1 to 5, preferably 1 to 3). Specifically included in the halo-lower alkoxy are fluoroalkoxy, difluoroalkoxy, trifluoroalkoxy, perfluoroalkoxy and the like. More specifically included are difluoromethoxy, trifluoromethoxy and the like.

Aryl includes a $C_{6-14}$ monocyclic, bicyclic or tricyclic aromatic hydrocarbon group, preferably $C_{6-10}$ monocyclic or bicyclic ones. Specifically included in the aryl are phenyl, naphthyl, phenanthryl, anthryl and the like.

Substituted amino includes mono-or di-substituted acyclic amino.

Cyclic amino includes 1-pyrrolidinyl, 1-piperidyl, 1-piperazinyl, morpholin-4-yl and the like.

Secondary hydroxy is hydroxy which connects with a carbon atom connecting with one hydrogen and two carbon atoms.

Tertiary hydroxy is hydroxy which connects with a carbon atom connecting with three carbon atoms.

In compound of formula [I] of the present invention, $R^1$ includes hydrogen, halogen, lower alkyl or cyano, and hydrogen is preferable.

Heterocycle moiety of the "optionally substituted heterocylic group" represented by Ring A preferably includes "monocyclic or bicylic heteroaryl containing 1 to 3 nitrogen atoms as a hetero atom or a group having an aliphatic 5 to 6-membered ring fused thereon". The "aliphatic 5 to 6-membered ring" which becomes fused includes 5 to 6-membered cycloalkane and aliphatic 5 to 6-membered heterocyclic ring (the preferable aliphatic 5 to 6-membered heterocyclic ring has a hetero atom selected from oxygen atom, nitrogen atom and sulfur atom, in particular oxygen atom), for example, specifically cyclohexane, tetrahydropyran and the like.

Specific examples of the heterocycle moiety include pyridyl, pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl, pyrazolo[1,5-a]pyrimidinyl and the like. Among these, pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl, and pyrazolo[1,5-a]pyrimidinyl are preferable, and pyrazinyl and quinoxalinyl are especially preferable. In addition, the heterocycle moiety preferably has a structure represented by formula [II]:

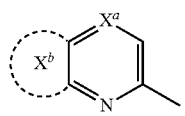

[II]

wherein:

$X^a$ is N or CH; and

Ring $X^b$ is a benzene ring, pyridine ring or an aliphatic 5 to 6-membered ring, or absent.

Specific examples of the heterocycle moiety include pyridin-2-yl, pyrazin-2-yl, quinolin-2-yl, quinoxalin-2-yl, 5,6,7,8-tetrahydroquinoxalin-2-yl, 7,8-dihydro-6H-pyrano[2,3-b]pyrazin-2-yl, 7,8-dihydro-6H-pyrano[2,3-b]pyrazin-3-yl, pyrido[3,4-b]pyrazin-2-yl, pyrido[3,4-b]pyrazin-3-yl and the like. Among these, pyrazin-2-yl, quinolin-2-yl, quinoxalin-2-yl, 5,6,7,8-tetrahydroquinoxalin-2-yl, 7,8-dihydro-6H-pyrano[2,3-b]pyrazin-2-yl, 7,8-dihydro-6H-pyrano[2,3-b]pyrazin-3-yl, pyrido[3,4-b]pyrazin-2-yl, and pyrido[3,4-b]pyrazin-3-yl and the like are preferred, and pyrazin-2-yl and quinoxalin-2-yl are especially preferable.

The "optionally substituted heterocyclic group" represented by Ring A may be unsubstituted, or may have 1 or more (for example, 1 to 6, preferably 1 to 3) substituent(s) which are the same or different. Examples of such substituent include
lower alkyl;
lower cycloalkyl,
halogen;
halo-lower alkyl;
hydroxy;
lower alkoxy;
halo-lower alkoxy;
optionally substituted amino (for example, it may have 1 to 2 substituent(s) which are the same or different and selected from lower alkyl, halogen and the like); and
optionally substituted cyclic amino (for example, it may have 1 to 3 substituent(s) which are the same or different and selected from lower alkyl, halogen, and the like). Among these, lower alkyl, cycloalkyl, halogen, halo-lower alkyl, optionally substituted amino and optionally substituted cyclic amino are preferable. In particular, lower alkyl, and halogen are preferable.

Preferable Ring A includes a group of formula [VI] or [VII]:

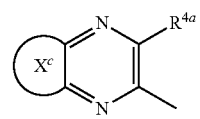

[VI]

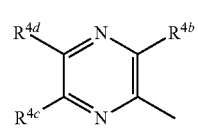

[VII]

wherein $X^c$ is a benzene ring, pyridine ring or an aliphatic 5 to 6-membered ring, each of which is optionally substituted by 1 to 2 substituents selected from lower alkyl; cycloalkyl; halogen; halo-lower alkyl; amino optionally substituted by 1 to 2 substituent(s) which are the same or different and selected from lower alkyl and halogen; and cyclic amino optionally substituted by 1 to 3 substituent(s) which are the same or different and selected from lower alkyl and halogen;
$R^{4a}$ is hydrogen or lower alkyl in particular, methyl;
$R^{4b}$ is hydrogen or lower alkyl in particular, methyl;
$R^{4c}$ and $R^{4d}$ are independently selected from lower alkyl; cycloalkyl; halogen; halo-lower alkyl; amino optionally substituted by 1 to 2 substituent(s) which are the same or different and selected from lower alkyl and halogen; and cyclic amino optionally substituted by 1 to 3 substituent(s) which are the same or different and selected from lower alkyl and halogen.

The "aliphatic 5 to 6-membered ring" in $X^b$ or $X^c$ includes 5 to 6-membered cycloalkane and aliphatic 5 to 6-membered heterocyclic ring (the preferable aliphatic 5 to 6-membered heterocyclic ring has a hetero atom selected from oxygen atom, nitrogen atom and sulfur atom, in particular oxygen atom).

Specific example of Ring A includes 3-methylpyrazin-2-yl; 3,6-dimethylpyrazin-2-yl; 3,5,6-trimethylpyrazin-2-yl; 3-methylpyridin-2-yl; 3,6-dimethylpyridin-2-yl; 3-methylquinoxalin-2-yl; 3-ethylquinoxalin-2-yl; 4-ethylquinoxalin-2-yl; 3-trifluoromethylquinoxalin-2-yl; 3,6-dimethylquinoxalin-2-yl; 3,7-dimethylquinoxalin-2-yl; 3,8-dimethylquinoxalin-2-yl; 7-fluoro-3-methylquinoxalin-2-yl; 3-methyl-7-trifluoroquinoxalin-2-yl; 3,6,7-trimethylquinoxalin-2-yl; 5-fluoro-3,7-dimethylquinoxalin-2-yl; 3-methylquinolin-2-yl; 4-methylquinolin-2-yl; 3-methyl-5,6,7,8-tetrahydro-quinoxalin-2-yl; 3-methyl-5-propylpyrazin-2-yl; 2-methyl-5-propylpyrazin-3-yl; 2,6-dimethyl-5-propylpyrazin-3-yl; 5-isobutyl-2-methylpyrazin-3-yl; 2,6-dimethyl-5-isobutylpyrazin-3-yl; 2,6-dimethyl-5-cyclopropylpyrazin-3-yl; 2-methyl-pyrido[3,4-b]pyrazin-3-yl; 3-methyl-pyrido[3,4-b]pyrazin-2-yl; 2-methyl-7,8-dihydro-6H-pyrano[2,3-b]pyrazin-3-yl; 3-methyl-7,8-dihydro-6H- pyrano[2,3-b]pyrazin-2-yl and 6-methyl-pyrazolo[1,5-a]pyrimidin-5-yl; in particular 3-methylquinoxalin-2-yl; and 7-fluoro-3-methylquinoxalin-2-yl.

Monocycle moiety of the "optionally substituted 3 to 6-membered monocyclic group" represented by Ring B includes a "4 to 6-membered monocyclic nitrogen-containing heterocyclic group" and a "3 to 6-membered monocyclic hydrocarbon group". Among these, "4 to 5-membered monocyclic nitrogen-containing aliphatic heterocyclic ring" and a "3 to 5-membered monocyclic aliphatic hydrocarbon group" are preferable. A "4 to 5-membered monocyclic nitrogen-containing aliphatic heterocyclic group having a bonding on the nitrogen atom of the cyclic group" is more preferable.

Specific examples of the "4 to 6-membered monocyclic nitrogen-containing heterocyclic group" include pyrrolidinyl, azetidinyl, imidazolidinyl, pyrazolidinyl, piperidinyl, piperazinyl, morpholinyl, thiomorpholinyl and unsaturated monocyclic group thereof in which a part or all is unsaturated. Among these, pyrrolidinyl, azetidinyl, pyrazolidinyl and unsaturated monocyclic group thereof in which a part or all is unsaturated are preferable. Among these, 1-pyrrolidinyl, 1-azetidinyl, 1-pyrazolidinyl and unsaturated monocylic group thereof in which a part or all is unsaturated (for example,

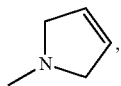

1-pyrazole and the like) are more preferable, 1-pyrrolidinyl and 1-azetidinyl are further preferable, and 1-pyrrolidinyl is especially preferable.

Examples of the "3 to 6-membered monocyclic hydrocarbon group" include $C_{3-6}$ cycloalkyl in which a part is optionally unsaturated. Specific examples include cyclopropyl, cyclobutyl, cyclopentyl, cyclohexyl, cyclopropenyl, cyclobutenyl, cyclopentenyl, cyclohexenyl and the like. Among these, cyclopentyl, cyclopentenyl (1-cyclopentenyl and the like) and the like are preferable.

Examples of the "3 to 6-membered monocyclic group" include 1-pyrrolidinyl, 1-azetidinyl, 1-pyrazolyl, cyclopropyl, cyclopentyl, cyclopenten-1-yl and the like.

The "optionally substituted 3 to 6-membered monocyclic group" represented by Ring B may be unsubstituted or may have 1 or more (for example, 1 to 3) substituent(s) which are the same or different. Examples of such substituent(s) include
halogen;
oxo;
hydroxy;
optionally substituted lower alkyl (for example, it may have 1 to 2 substituent(s) which are the same or different and selected from hydroxy, lower alkoxy and the like);
lower alkoxy;
lower alkylsulfonyloxy;
optionally substituted amino (for example, it may have 1 to 2 substituent(s) which are the same or different and selected from lower alkyl and the like) and the like. Among these, halogen; hydroxy; optionally substituted lower alkyl (for example, it may have 1 to 2 substituent(s) which are the same or different and selected from hydroxy, lower alkoxy and the like) and the like are preferable, and halogen is especially preferable, in particular fluorine.

Preferable examples of Y include a group represented by the following formula [III]:

[III]

wherein:
Z is —N($R^3$)—, —O— or $C_{1-2}$ alkylene;
$R^3$ is hydrogen; lower alkyl optionally substituted by 1 to 2 substituent(s) which are the same or different and selected from hydroxy and lower alkoxy; or lower cycloalkyl; and
$R^2$ is
(1) lower alkyl optionally substituted by 1 to 3 substituent(s) which are the same or different and selected from the group consisting of hydroxy, halogen, cyano, lower alkoxy, lower cycloalkyl, hydroxy-substituted lower cycloalkyl, halo-lower alkyl and mono- or di-lower alkyl amino; or
(2) an optionally substituted aliphatic 3 to 6-membered monocyclic group.

Z is preferably —N($R^3$)— or —O—, more preferably —N($R^3$)—.

$R^3$ is preferably hydrogen or lower alkyl (for example, methyl), more preferably hydrogen.

The "lower alkyl optionally substituted by 1 to 3 substituent(s) which are the same or different and selected from the group consisting of hydroxy, halogen, cyano, lower alkoxy, lower cycloalkyl, hydroxy-substituted lower cycloalkyl, halo-lower alkyl and mono- or di-lower alkyl amino" of $R^2$ is preferably hydroxy-substituted lower alkyl optionally substituted by halo-lower alkyl. Hydroxy of "hydroxy-substituted lower alkyl" of $R^2$ is preferably secondary or tertiary hydroxy, in particular tertiary hydroxy.

Specific example of "lower alkyl optionally substituted by 1 to 3 substituent(s) which are the same or different and selected from the group consisting of hydroxy, halogen, cyano, lower alkoxy, lower cycloalkyl, hydroxy-substituted lower cycloalkyl, halo-lower alkyl and mono- or di-lower alkyl amino" includes
2-hydroxypropan-1-yl;
2-hydroxy-2-methylpropan-1-yl;
1,1,1-trifluoro-2-hydroxypropan-3-yl; and
3-hydroxy-3-methylbutan-1-yl.

Monocycle moiety of the "optionally substituted aliphatic 3 to 6-membered monocyclic group" represented by $R^2$ preferably include a 4 to 6-membered (preferably 5 to 6-membered) aliphatic monocylic heterocyclic group containing 1 to 2 hetero atom(s) selected from oxygen atom, nitrogen atom and sulfur atom; $C_{3-6}$ (preferably $C_{5-6}$) cycloalkyl; and the like.

Specific examples of the monocycle moiety include tetrahydropyranyl, tetrahydrofuranyl, oxetanyl, tetrahydrothiopyranyl, tetrahydrothienyl, thietanyl, piperidyl, $C_{3-6}$cycloalkyl (cyclohexyl, cyclopentyl, cyclobutyl, and cyclopropyl) and the like. Among these, tetrahydropyranyl, tetrahydrofuranyl, oxetanyl, $C_{3-6}$cycloalkyl and the like are preferable. Among these, tetrahydropyranyl, cyclohexyl and the like are especially preferable.

In addition, more specific examples of the monocycle moiety include 3- or 4-tetrahydropyranyl, 3-tetrahydrofuranyl, 3-oxetanyl, 3- or 4-tetrahydrothiopyranyl, 3-tetrahydrothienyl, 3-thietanyl, 4-piperidyl, $C_{3-6}$cycloalkyl and the like. Among these, 3- or 4-tetrahydropyranyl, 3-tetrahydrofuranyl, 3-oxetanyl, 3-tetrahydrothienyl, 4-piperidyl, $C_{3-6}$cycloalkyl and the like are preferable. Among these, 3- or 4-tetrahydropyranyl, 3-tetrahydrofuranyl, cyclohexyl and the like are further preferable.

The "optionally substituted aliphatic 3 to 6-membered monocyclic group" represented by $R^2$ may be unsubstituted, or may have 1 or more (for example, 1 to 3) substitutent(s) which are the same or different. Examples of such substituent(s) include halogen, oxo, hydroxy, lower alkanoyl, lower alkoxy and optionally substituted lower alkyl and the like (for example, it may have 1 to 2 substituent(s) which are the same or different and selected from hydroxy, lower alkoxy and the like). Halogen, oxo, hydroxyl, lower alkanoyl, lower alkoxy, lower alkyl optionally substituted by 1 to 2 substituent(s) which are the same or different and selected from hydroxy and lower alkoxy are further preferable.

The "optionally substituted aliphatic 3 to 6-membered monocyclic group" represented by $R^2$ is preferably a group represented by the following formula [IV]:

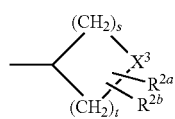

wherein:
$X^3$ is —O—, —S—, —C($R^{2c}$)($R^{2d}$)— or —SO$_2$—;
s and t are each independently 1, 2, 3 or 4;
s+t is 2, 3, 4 or 5; and
$R^{2a}$, $R^{2b}$, $R^{2C}$, $R^{2d}$ are the same or different, and each independently are hydrogen, halogen, oxo, hydroxy, lower alkanoyl, lower alkoxy, or lower alkyl optionally substituted by 1 to 2 substituent(s) which are the same or different and selected from hydroxy and lower alkoxy.

$X^3$ is preferably —O— or —C($R^{2c}$)($R^{2d}$)—.
s and t are preferably 1 or 2, more preferably 2.
s+t is preferably 2, 3 or 4, more preferably 3 or 4.

The "optionally substituted aliphatic 3 to 6-membered monocyclic group" represented by $R^2$ is more preferably a group represented by the following formula [V]:

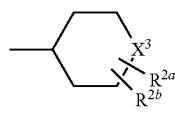

wherein the symbols are the same as defined above.

Examples of the "optionally substituted amino" represented by Y include unsubstituted amino and substituted amino. Among these, substituted amino is preferable.

Examples of the "substituted amino" represented by Y include ones having 1 to 2 substituent(s) which are the same or different. Examples of such substituent(s) of the "substituted amino" include ones that are similar to the aforementioned groups represented by $R^3$ and $R^2$ in formula [III].

The "substituted amino" represented by Y is preferably mono-substituted amino. The substituent in such case is preferably ones that are similar to the aforementioned groups represented by $R^2$ in formula [III], and more preferably ones that are similar to "optionally substituted aliphatic 3 to 6-membered monocyclic group" or "optionally substituted lower alkyl" represented by $R^2$.

Specific examples of "substituted amino" represented by Y of formula [I] include 4-tetrahydropyranylamino; N-methyl-N-tetrahydropyran-4-ylamino; (2-hydroxy-2-methylpropan-1-yl)amino; (4-hydroxy-4-methylcyclohexyl)amino; 3-oxetanylamino; (1-hydroxymethylcyclopropan-1-yl)amino; cyclopropylamino; 2-hydroxypropan-1-ylamino; 2-methoxyethan-1-ylamino; 4-hydroxycyclohexylamino; 4-methoxycyclohexylamino; 4-ethoxycyclohexylamino; 2,2-dimethyltetrahydropyran-4-ylamino; 2,6-dimethyltetrahydropyran-4-ylamino; 1,1,1,-trifluoro-2-hydroxypropan-3-ylamino; 3-tetrahydropyranylamino; 2-cyanoethan-1-ylamino; (1-hydroxy-2-methylpropan-2-yl) amino; 1,1-difluoroethan-2-ylamino; 1-hydroxycyclopropan-1-ylmethylamino; 3-tetrahydrofuranylamino; 1-methylpiperidin-4-ylamino; di(1-methoxyethan-2-yl)amino; N-cyclopropyl-N-tetrahydropyran-4-ylamino; N-ethyl-N-tetrahydropyran-4-ylamino; 2-hydroxypropan-1-ylamino; 3-hydroxy-3-methylbutan-1-ylamino; 2-hydroxycyclohexan-1-ylamino; 1-hydroxy-2,2-dimethylpropan-3-ylamino; 1,1-dioxo-tetrahydrothiophen-3-ylamino; 1-acetylpiperidin-4-ylamino; 1-propylpiperidin-4-ylamino; 1-ethylpiperidin-4-ylamino; 1-(N,N-dimethylamino)ethan-2-ylamino; and 4,4-difluorocyclohexylamino,
in particular 4-tetrahydropyranylamino, (2-hydroxy-2-methylpropan-1-yl)amino, (4-hydroxy-4-methylcyclohexyl) amino, 2-hydroxypropan-1-ylamino, 1,1,1,-trifluoro-2-hydroxypropan-3-ylamino, and 3-hydroxy-3-methylbutan-1-ylamino.

Examples of the "cyclic amino" represented by Y preferably include 1-pyrrolidinyl, morpholin-4-yl, 1-piperidyl, 1-piperazinyl and the like. Among these, 1-pyrrolidinyl, morpholin-4-yl and the like are preferable.

Examples of the "optionally substituted aliphatic 3 to 6-membered monocycle" moiety in the "optionally substituted aliphatic 3 to 6-membered monocyclyloxy" represented by Y include ones that are similar to the aforementioned "optionally substituted aliphatic 3 to 6-membered monocyclic group" represented by $R^2$ in formula [III].

The "optionally substituted lower alkyl" represented by Y may be unsubstituted ones, or may be ones having 1 or more (for example, 1 to 3) substitutent(s) which are the same or different. Examples of such substituent(s) include an optionally substituted aliphatic 3 to 6-membered monocyclic group, hydroxy, halogen, cyano, lower alkoxy, mono- or di-lower alkylamino, cycloalkyl and the like. Examples of such "optionally substituted aliphatic 3 to 6-membered monocyclic group" include ones that are similar to the aforementioned "optionally substituted aliphatic 3 to 6-membered monocylic group" represented by $R^2$ in formula [III].

The "optionally substituted lower alkyl-O—" represented by Y may be unsubstituted ones or may be ones having 1 or more (for example, 1 to 3) substituent(s) which are the same or different. Examples of such substituent(s) include halogen, hydroxy, lower alkoxy and the like.

One aspect of the present invention includes those compound of formula [I] wherein $R^1$ is hydrogen.

Another aspect of the invention includes the aforementioned compound wherein Ring A is optionally substituted monocyclic or bicylic heteroaryl containing 1 to 3 nitrogen atoms as a hetero atom or a group having an aliphatic 5 to 6-membered ring fused thereon In one of these aspects, Ring A is a group of formula [II], which is optionally substituted.

In one of these aspects, Ring A is pyridyl, pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl, pyrazolo[1,5-a]pyrimidinyl, each of which is optionally substituted.

In one of these aspects, Ring A is pyridyl, pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl, and pyrazolo[1,5-a]pyrimidinyl, each of which is optionally substituted.

In one of these aspects, Ring A is pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl and pyrazolo[1,5-a]pyrimidinyl.

In one of these aspects, Ring A is pyrazinyl and quinoxalinyl, each of which is optionally substituted.

In one of these aspects, Ring A is pyrazin-2-yl, quinolin-2-yl, quinoxalin-2-yl, 5,6,7,8-tetrahydroquinoxalin-2-yl, 7,8-dihydro-6H-pyrano[2,3-b]pyrazin-2-yl, 7,8-dihydro-6H-pyrano[2,3-b]pyrazin-3-yl, pyrido[3,4-b]pyrazin-2-yl, and pyrido[3,4-b]pyrazin-3-yl, each of which is optionally substituted.

In one of these aspects, Ring A is pyrazin-2-yl and quinoxalin-2-yl, each of which is optionally substituted.

Another aspects of the invention includes the aforementioned compound wherein Ring A may have 1 or more (for example, 1 to 6, preferably 1 to 3) substituent(s) which are the same or different substituent selected from lower alkyl; lower cycloalkyl, halogen; halo-lower alkyl; hydroxy; lower alkoxy; halo-lower alkoxy; optionally substituted amino (for example, it may have 1 to 2 substituent(s) which are the same or different and selected from lower alkyl, halogen and the like); and optionally substituted cyclic amino (for example, it may have 1 to 3 substituent(s) which are the same or different and selected from lower alkyl, halogen, and the like).

In one of these aspects, the substituents in the "optionally substituted heterocyclic group" represented by Ring A are 1 to 6 substituent(s) which are the same or different and selected from the group consisting of lower alkyl; halogen; halo-lower alkyl; hydroxy; lower-alkoxy; halo-lower alkoxy; amino optionally substituted by 1 to 2 substituent(s) which are the same or different and selected from lower-alkyl and halogen; and cyclic amino optionally substituted by 1 to 3 substituent(s) which are the same or different and selected from lower-alkyl and halogen.

In one of these aspects, the substituents in the "optionally substituted heterocyclic group" represented by Ring A are 1 to 3 substituents) which are the same or different and selected from the group consisting of lower alkyl; halogen; halo-lower alkyl; amino optionally substituted by 1 to 2 substituent(s) which are the same or different and selected from lower-alkyl and halogen; and cyclic amino optionally substituted by 1 to 3 substituents) which are the same or different and selected from lower-alkyl and halogen.

In one of these aspects, the substituents in the "optionally substituted heterocyclic group" represented by Ring A are 1 to 3 substituents) which are the same or different and selected from the group consisting of lower alkyl, and halogen.

Another aspect of the invention includes those compound of formula [I] wherein Ring A is a group of formula [VI] or [VII].

In one of these aspects, Ring A is a group of formula [VI].
In one of these aspects, Ring A is a group of formula [VII].

Another aspect of the invention includes the aforementioned compound wherein the monocycle moiety in the "optionally substituted 3 to 6-membered monocyclic group" represented by Ring B is a 4 to 6-membered monocyclic nitrogen-containing heterocyclic group.

In one of these aspects, monocycle moiety in the "optionally substituted 3 to 6-membered monocyclic group" represented by Ring B is a 4 to 6-membered monocyclic nitrogen-containing heterocyclic group or 3 to 6-membered monocyclic hydrocarbon group.

In one of these aspects, monocyclic moiety in "optionally substituted 3 to 6-membered monocyclic group" represented by Ring B is selected from the group consisting of pyrrolidinyl, azetidinyl, imidazolidinyl, pyrazolidinyl, piperidinyl, piperazinyl, morpholinyl, thiomorpholinyl and $C_{3-6}$ cycloalkyl, or unsaturated monocyclic group thereof;

In one of these aspects, monocyclic moiety in "optionally substituted 3 to 6-membered monocyclic group" represented by Ring B is selected from the group consisting of pyrrolidinyl, azetidinyl, imidazolidinyl, pyrazolidinyl, piperidinyl, piperazinyl, morpholinyl, thiomorpholinyl and unsaturated monocyclic group thereof, in which a part or all is unsaturated.

In one of these aspects, monocyclic moiety in "optionally substituted 3 to 6-membered monocyclic group" represented by Ring B is pyrrolidinyl, azetidinyl, pyrazolidinyl and unsaturated monocyclic group thereof, in which a part or all is unsaturated are preferable.

In one of these aspects, monocyclic moiety in "optionally substituted 3 to 6-membered monocyclic group" represented by Ring B is 1-pyrrolidinyl, 1-azetidinyl, 1-pyrazolidinyl and unsaturated monocylic group thereof in which a part or all is unsaturated.

In one of these aspects, monocyclic moiety in "optionally substituted 3 to 6-membered monocyclic group" represented by Ring B is 1-pyrrolidinyl, 1-azetidinyl, 1-pyrazolyl, cyclopropyl, cyclopentyl, or cyclopenten-1-yl.

In one of these aspects, monocyclic moiety in "optionally substituted 3 to 6-membered monocyclic group" represented by Ring B is 1-pyrrolidinyl.

Another aspect of the invention includes the aforementioned compound wherein the "optionally substituted 3 to 6-membered monocyclic group" represented by Ring B is a 3 to 6-membered monocyclic group optionally substituted by 1 to 3 substituent(s) which are same or different and selected from the group consisting of halogen; oxo; hydroxy; lower alkyl optionally substituted by 1 to 2 substituent(s) which are the same or different and selected from hydroxy and lower alkoxy; lower alkoxy; lower alkylsulfonyloxy; and amino optionally substituted by 1 to 2 substituent(s) which are the same or different and selected from lower alkyl.

In one of these aspects, "optionally substituted 3 to 6-membered monocyclic group" represented by Ring B is a 3 to 6-membered monocyclic group optionally substituted by 1 to 3 substituents) which are same or different and selected from halogen; hydroxy; lower alkyl optionally substituted by 1 to 2 substituent(s) which are the same or different and selected from hydroxy and lower alkoxy.

Another aspect of the invention includes the aforementioned compound, wherein Y is represented by formula [III].

In one of these aspects, Y is represented by formula [III] wherein Z is —N($R^3$)— or —O—.

In one of these aspects, Y is represented by formula [III] wherein Z is —N($R^3$)—.

Another aspect of the invention includes the aforementioned compound, wherein Y is represented by formula [III]: wherein $R^3$ is hydrogen.

Another aspect of the invention includes the aforementioned compound, wherein Y is represented by formula [III] wherein "optionally substituted aliphatic 3 to 6-membered monocyclic group" represented by $R^2$ is an aliphatic 3 to 6-membered monocyclic group optionally substituted by 1 to 3 substituent(s) which are the same or different and selected from the group consisting of halogen; oxo; hydroxy; lower alkanoyl; lower alkoxy; and lower alkyl optionally substituted by 1 to 2 substituent(s) which are the same or different and selected from hydroxy and lower alkoxy.

In one of these aspects, the monocycle moiety in the "optionally substituted aliphatic 3 to 6-membered monocyclic group" is represented by formula [IV].

In one of these aspects, the monocycle moiety in the "optionally substituted aliphatic 3 to 6-membered monocyclic group" is represented by formula [V].

In one of these aspects, the monocycle moiety in the "optionally substituted aliphatic 3 to 6-membered monocyclic group" represented by R² is selected from the group consisting of tetrahydropyranyl, tetrahydrofuranyl, oxetanyl, tetrahydrothiopyranyl, tetrahydrothienyl, thietanyl, piperidyl, cyclohexyl, cyclopentyl and cyclobutyl.

In one of these aspects, the monocycle moiety in the "optionally substituted aliphatic 3 to 6-membered monocyclic group" represented by R² is selected from the group consisting of 3- or 4-tetrahydropyranyl, 3-tetrahydrofuranyl, 3-oxetanyl, 3- or 4-tetrahydrothiopyranyl, 3-tetrahydrothienyl, 3-thietanyl, 4-piperidyl, and $C_{3-6}$cycloalkyl.

In one of these aspects, Y is represented by formula [III] wherein R² is a lower alkyl optionally substituted by 1 to 3 substituent(s) which are the same or different and selected from the group consisting of hydroxy, halogen, cyano, lower alkoxy, lower cycloalkyl, hydroxy-substituted lower cycloalkyl, halo-lower alkyl and mono- or di-lower alkyl amino.

In one of these aspects, Y is represented by formula [III] wherein R² is an optionally substituted aliphatic 3 to 6-membered monocyclic group.

In one of these aspects, Y is represented by formula [III] wherein R² is
(1) lower alkyl optionally substituted by 1 to 3 substituent(s) which are the same or different and selected from the group consisting of hydroxy, halogen, cyano, lower alkoxy, hydroxy-substituted lower cycloalkyl, halo-lower alkyl and mono- or di-lower alkyl amino; or
(2) 3- or 4-tetrahydropyranyl, 3-tetrahydrofuranyl, 3-oxetanyl, 3-tetrahydrothienyl, 4-piperidyl, cyclohexyl, or $C_{3-6}$cycloalkyl, each of which is optionally substituted by 1 to 3 substituent(s) which are the same or different and selected from the group consisting of halogen; oxo; hydroxy; lower alkanoyl; lower alkoxy; and lower alkyl optionally substituted by 1 to 2 substituent(s) which are the same or different and selected from hydroxy and lower alkoxy.

In one of these aspects, Y is represented by formula [III] wherein R² is selected from the group consisting of 4-tetrahydropyranyl; 4-hydroxy-4-methylcyclohexyl; 2-hydroxypropan-1-yl; 2-hydroxy-2-methylpropan-1-yl; 1,1,1-trifluoro-2-hydroxypropan-3-yl; and 3-hydroxy-3-methylbutan-1-yl.

Another aspect of the invention includes the aforementioned compound wherein Y is optionally substituted amino.

Another aspect of the invention includes the aforementioned compound wherein Y is optionally substituted cyclic amino.

Another aspect of the invention includes the aforementioned compound wherein Y is optionally substituted aliphatic 3 to 6-membered monocyclyloxy.

Another aspect of the invention includes the aforementioned compound wherein Y is optionally substituted lower alkyl.

Another aspect of the invention includes the aforementioned compound wherein Y is optionally substituted lower alkyl-O—.

Preferably, examples of the compound of formula [I] include the free form of each compounds described in the Examples (Examples 1.001 to 1.200, 2.001, 3.001, 4.001 to 4.005, 5.001 and 5.002) or pharmaceutically acceptable salts thereof.

Especially preferably, examples of the compound include ones selected from the group consisting of
2-(3-methylquinoxalin-2-yl)-5-pyrrolidin-1-yl-N-(tetrahydro-2H-pyran-4-yl)pyrazolo[1,5-a]pyrimidin-7-amine (Free form of Example 1.001);
N-Methyl-2-(3-methylquinoxalin-2-yl)-5-pyrrolidin-1-yl-N-(tetrahydro-2H-pyran-4-yl)pyrazolo[1,5-a]pyrimidin-7-amine (Free form of Example 1.002);
5-[(3R)-3-fluoropyrrolidin-1-yl]-2-(3-methylquinoxalin-2-yl)-N-(tetrahydro-2H-pyran-4-yl)pyrazolo[1,5-a]pyrimidin-7-amine (Free form of Example 1.003);
1-({2-(7-fluoro-3-methylquinoxalin-2-yl)-5-[(3R)-3-fluoropyrrolidin-1-yl]pyrazolo[1,5-a]pyrimidin-7-yl}amino)-2-methylpropan-2-ol (Free form of Example 1.006);
5-(2,5-dihydro-1H-pyrrol-1-yl)-2-(3-methylquinoxalin-2-yl)-N-(tetrahydro-2H-pyran-4-yl)pyrazolo[1,5-a]pyrimidin-7-amine (Example 1.009);
2-methyl-3-[5-pyrrolidin-1-yl-7-(tetrahydro-2H-pyran-4-yloxy)pyrazolo[1,5-a]pyrimidin-2-yl]quinoxaline (Free form of Example 1.010);
5-cyclopent-1-en-1-yl-2-(3-methylquinoxalin-2-yl)-N-(tetrahydro-2H-pyran-4-yl)pyrazolo[1,5-a]pyrimidin-7-amine (Example 1.011);
trans-4-({2-(7-fluoro-3-methylquinoxalin-2-yl)-5-[(3R)-3-fluoropyrrolidin-1-yl]pyrazolo[1,5-a]pyrimidin-7-yl}amino)-1-methylcyclohexanol (Free form of Example 1.013);
2-(5,7-dipyrrolidin-1-ylpyrazolo[1,5-a]pyrimidin-2-yl)-3-methylquinoxaline (Free form of Example 1.019);
(2S)-1,1,1-trifluoro-3-{[2-(3-methylquinoxalin-2-yl)-5-pyrrolidin-1-ylpyrazolo[1,5-a]pyrimidin-7-yl]amino}propan-2-ol (Free form of Example 1.027);
3-{[2-(3-methylquinoxalin-2-yl)-5-pyrrolidin-1-ylpyrazolo[1,5-a]pyrimidin-7-yl]amino}propanenitrile (Free form of Example 1.031);
N-(trans-4-methoxycyclohexyl)-2-[3-methyl-7-(trifluoromethyl)quinoxalin-2-yl]-5-pyrrolidin-1-ylpyrazolo[1,5-a]pyrimidin-7-amine (Free form of Example 1.047);
2-(3,7-dimethylquinoxalin-2-yl)-N,N-bis(2-methoxyethyl)-5-pyrrolidin-1-ylpyrazolo[1,5-a]pyrimidin-7-amine (Free form of Example 1.050);
5-[(3R)-3-fluoropyrrolidin-1-yl]-2-(3-methylquinoxalin-2-yl)-N-oxetan-3-ylpyrazolo[1,5-a]pyrimidin-7-amine (Example 1.058);
1-{[5-[(3R)-3-fluoropyrrolidin-1-yl]-2-(3-methylquinoxalin-2-yl)pyrazolo[1,5-a]pyrimidin-7-yl]amino}-2-methylpropan-2-ol (Free form of Example 1.059);
N-cyclopropyl-5-[(3R)-3-fluoropyrrolidin-1-yl]-2-(3-methylquinoxalin-2-yl)pyrazolo[1,5-a]pyrimidin-7-amine (Free form of Example 1.062);
2-(3-ethylquinoxalin-2-yl)-5-[(3R)-3-fluoropyrrolidin-1-yl]-N-(trans-4-methoxycyclohexyl)pyrazolo[1,5-a]pyrimidin-7-amine (Free form of Example 1.081);
trans-4-({5-[(3R)-3-fluoropyrrolidin-1-yl]-2-[3-(trifluoromethyl)quinoxalin-2-yl]pyrazolo[1,5-a]pyrimidin-7-yl}amino)-1-methylcyclohexanol (Free form of Example 1.085);
(1S,2S)-2-[{2-(7-fluoro-3-methylquinoxalin-2-yl)-5-pyrrolidin-1-ylpyrazolo[1,5-a]pyrimidin-7-yl]amino}cyclohexanol (Free form of Example 1.097);
2-(3,5-dimethylquinoxalin-2-yl)-5-pyrrolidin-1-yl-N-(tetrahydro-2H-pyran-4-yl)pyrazolo[1,5-a]pyrimidin-7-amine (Free form of Example 1.109);
2-(3,6-dimethylquinoxalin-2-yl)-5-pyrrolidin-1-yl-N-(tetrahydro-2H-pyran-4-yl)pyrazolo[1,5-a]pyrimidin-7-amine (Free form of Example 1.111);
2-(3,7-dimethylquinoxalin-2-yl)-N-[(3R)-1,1-dioxidotetrahydro-3-thienyl]-5-pyrrolidin-1-ylpyrazolo[1,5-a]pyrimidin-7-amine (Free form of Example 1.112);
N-(1-acetylpiperidin-4-yl)-2-(3,7-dimethylquinoxalin-2-yl)-5-pyrrolidin-1-ylpyrazolo[1,5-a]pyrimidin-7-amine (Free form of Example 1.114);
2-(3,7-dimethylquinoxalin-2-yl)-N-(1-propylpiperidin-4-yl)-5-pyrrolidin-1-ylpyrazolo[1,5-a]pyrimidin-7-amine (Free form of Example 1.123);
N'-[2-(3,7-dimethylquinoxalin-2-yl)-5-pyrrolidin-1-ylpyrazolo[1,5-a]pyrimidin-7-yl]-N,N-dimethylethane-1,2-diamine (Free form of Example 1.126);
N-(4,4-difluorocyclohexyl)-2-(3-methyl-5,6,7,8-tetrahydroquinoxalin-2-yl)-5-pyrrolidin-1-ylpyrazolo[1,5-a]pyrimidin-7-amine (Example 1.133);

N-methyl-5-pyrrolidin-1-yl-N-(tetrahydro-2H-pyran-4-yl)-2-(3,5,6-trimethylpyrazin-2-yl)pyrazolo[1,5-a]pyrimidin-7-amine (Example 1.158);

((2S)-1-{2-(3-methylquinoxalin-2-yl)-7-[(3R)-tetrahydro-2H-pyran-3-ylamino]pyrazolo[1,5-a]pyrimidin-5-yl}pyrrolidin-2-yl)methanol (Free form of Example 1.147);

{(2S)-1-[7-[cyclopropyl(tetrahydro-2H-pyran-4-yl)amino]-2-(3,7-dimethylquinoxalin-2-yl)pyrazolo[1,5-a]pyrimidin-5-yl]pyrrolidin-2-yl}methanol (Free form of Example 1.152);

1-[2-(3,7-dimethylquinoxalin-2-yl)-7-(tetrahydro-2H-pyran-4-ylamino)pyrazolo[1,5-a]pyrimidin-5-yl]azetidin-3-ol (Free form of Example 1.154);

2-methyl-3-[5-pyrrolidin-1-yl-7-(tetrahydro-2H-pyran-4-ylmethyl)pyrazolo[1,5-a]pyrimidin-2-yl]quinoxaline (Example 2.001);

trans-1-methyl-4-{[2-(3-methyl-7,8-dihydro-6H-pyrano[2,3-b]pyrazin-2-yl)-5-pyrrolidin-1-ylpyrazolo[1,5-a]pyrimidin-7-yl]amino}cyclohexanol (Free form of Example 1.173);

cis-4-({2-(7-fluoro-3-methylquinoxalin-2-yl)-5-[(3R)-3-fluoropyrrolidin-1-yl]pyrazolo[1,5-a]pyrimidin-7-yl}amino)-1-methylcyclohexanol (Free form of Example 1.175);

N-methyl-2-(3-methyl-6-propylpyrazin-2-yl)-5-pyrrolidin-1-yl-N-(tetrahydro-2H-pyran-4-yl)pyrazolo[1,5-a]pyrimidin-7-amine (Free form of Example 1.181);

2-methyl-1-[(6'-methyl-5-pyrrolidin-1-yl-2,5'-bipyrazolo[1,5-a]pyrimidin-7-yl)amino]propan-2-ol (Free form of Example 1.184);

1-{[2-(6-isobutyl-3,5-dimethylpyrazin-2-yl)-5-pyrrolidin-1-ylpyrazolo[1,5-a]pyrimidin-7-yl]amino}-2-methylpropan-2-ol (Example 1.187);

1-{[2-(6-cyclopropyl-3,5-dimethylpyrazin-2-yl)-5-pyrrolidin-1-ylpyrazolo[1,5-a]pyrimidin-7-yl]amino}-2-methylpropan-2-ol (Free form of Example 1.189);

2-(6-cyclopropyl-3,5-dimethylpyrazin-2-yl)-5-pyrrolidin-1-yl-N-(tetrahydro-2H-pyran-4-yl)pyrazolo[1,5-a]pyrimidin-7-amine (Free form of Example 1.190);

2-(3-methyl-7,8-dihydro-6H-pyrano[2,3-b]pyrazin-2-yl)-5-pyrrolidin-1-yl-N-(tetrahydro-2H-pyran-4-yl)pyrazolo[1,5-a]pyrimidin-7-amine (Free form of Example 1.197);

2-methyl-1-{[2-(3-methyl-7,8-dihydro-6H-pyrano[2,3-b]pyrazin-2-yl)-5-pyrrolidin-1-ylpyrazolo[1,5-a]pyrimidin-7-yl]amino}propan-2-ol (Free form of Example 1.198);

N-(trans-4-methoxycyclohexyl)-2-(3-methyl-7,8-dihydro-6H-pyrano[2,3-b]pyrazin-2-yl)-5-pyrrolidin-1-ylpyrazolo[1,5-a]pyrimidin-7-amine (Free form of Example 1.199);

2-(2-methylpyrido[3,4-b]pyrazin-3-yl)-5-pyrrodin-1-yl-N-(tetrahydro-2H-pyran-4-yl)pyrazolo[1,5-a]pyrimidin-7-amine (Example 5.001); and 2-(3-methylpyrido[3,4-b]pyrazin-2-yl)-5-pyrrolidin-1-yl-N-(tetrahydro-2H-pyran-4-yl)pyrazolo[1,5-a]pyrimidin-7-amine (Example 5.002);

or a pharmaceutically acceptable salt thereof.

The compounds of formula [I] of the present invention may be in a free form (free base or free acid) or in the form of a pharmaceutically acceptable salt thereof. Examples of the pharmaceutically acceptable salts include inorganic acid salts such as hydrochloride, sulfate, nitrate, phosphate or hydrobromate salts, and organic acid salts such as acetate, fumarate, oxalate, citrate, methanesulfonate, benzenesulfonate, p-toluenesulfonate or maleate salts, and the like. Further, when the compounds of the present invention contain substituent(s) such as carboxyl group, the pharmaceutically acceptable salts thereof include salts with bases (for example, alkali metal salts such as sodium salt, potassium salts and the like, or alkaline earth metal salts such as calcium salt).

The compounds of formula [I] or salts thereof of the present invention encompass any of intramolecular salts, adducts, solvates or hydrates thereof.

The compounds of formula [I] of the present invention can be prepared in accordance with the following, but shall not be limited to these.

Preparation Method 1

Compounds of formula [I], wherein $R^1$ is hydrogen, and Y is optionally substituted amino, optionally substituted cyclic amino, optionally substituted aliphatic 3 to 6-membered monocyclyloxy or optionally substituted lower alkoxy, that is, compounds represented by the following:

formula [Ia$^1$] [wherein, $B^1$ is an optionally substituted nitrogen-containing heterocyclic group, $Y^a$ is optionally substituted amino, optionally substituted cyclic amino, optionally substituted aliphatic 3 to 6-membered monocyclyloxy or optionally substituted lower alkoxy, and the other symbols have the same meaning as defined above];

formula [Ia$^2$] [wherein, $B^2$ is an optionally substituted 3 to 6-membered monocyclic group, in which the monocycle moiety is unsaturated, and the other symbols have the same meanings as defined above]; and formula [Ia$^3$] [wherein, $B^3$ is an optionally substituted 3 to 6-membered monocyclic group, in which the monocycle moiety is saturated, and the other symbols have the same meanings as defined above]

can be prepared by the following preparation method.

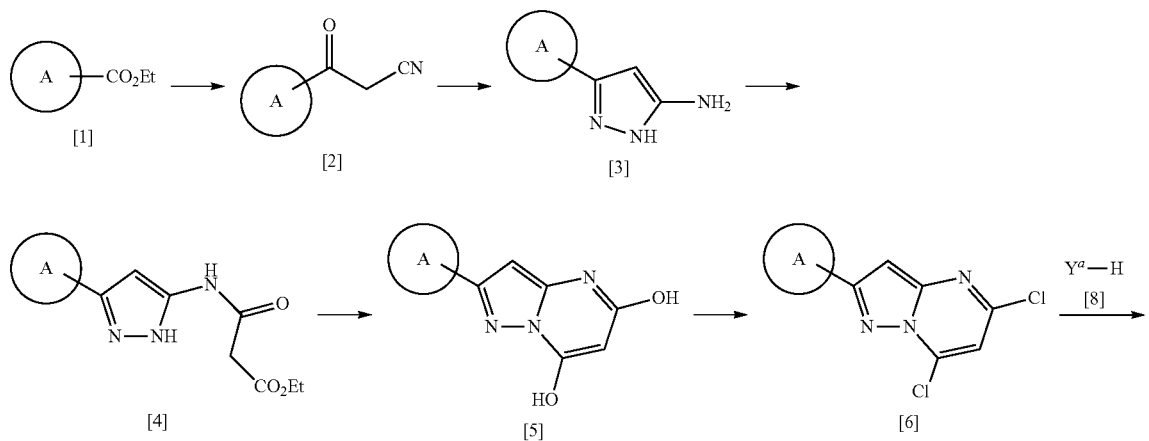

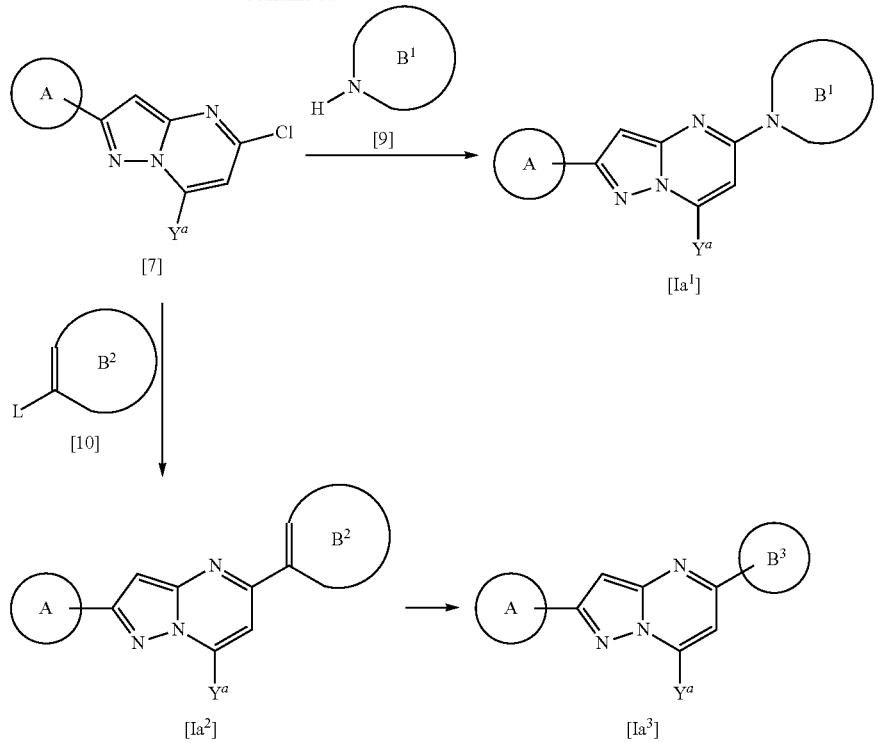

The compound of formula [1] [wherein, each symbol has the same meanings as defined above] is reacted with acetonitrile to provide the compound of formula [2] [wherein, each symbol has the same meanings as defined above].

The compound of formula [2] is reacted with hydrazine to provide the compound of formula [3] [wherein, each symbol has the same meanings as defined above].

The compound of formula [3] is reacted with ethyl malonyl chloride, followed by addition of a nucleophilic agent to provide the compound of formula [4] [wherein, each symbol has the same meanings as defined above]. Alternatively, the compound of formula [3] is reacted with ethyl hydrogen malonate to provide the compound of formula [4].

The compound of formula [4] is subjected to cyclization to provide the compound of formula [5] [wherein, each symbol has the same meanings as defined above].

The compound of formula [5] is subjected to halogenation to provide the compound of formula [6] [wherein, each symbol has the same meanings as defined above].

The compound of formula [6] is reacted with the compound of formula [8] [wherein, each symbol has the same meanings as defined above] to provide the compound of formula [7] [wherein, each symbol has the same meanings as defined above].

The compound of formula [7] is reacted with the compound of formula [9] [wherein, each symbol has the same meanings as defined above] to provide the compound of formula [Ia$^1$], which is optionally converted to a pharmaceutically acceptable salt.

The compound of formula [7] is reacted with the compound of formula [10] [wherein, L is —B(OR)$_2$, —B(OH)$_2$ or —SnR$_3$, R is lower alkyl, and the other symbols have the same meanings as defined above] to provide the compound of formula [Ia$^2$], which is optionally converted to a pharmaceutically acceptable salt.

The compound of formula [Ia$^2$] is reduced to provide the compound of formula [Ia$^3$], which is optionally converted to a pharmaceutically acceptable salt.

The reaction of the compound of formula [1] and acetonitrile suitably proceeds in the presence of a base. As such base, alkali metal alkoxides such as potassium tert-butoxide, alkali metal hydrides such as sodium hydride, alkali metal hydroxides such as sodium hydroxide, can suitably be used for example. The reaction can be carried out in a suitable solvent. As such solvent, any solvent which does not have a negative impact on the reaction can be used, and for example, toluene and the like can suitably be used. The reaction suitably proceeds at −78° C. to 100° C., particularly at 0° C. to room temperature.

The reaction of the compound of formula [2] and hydrazine suitably proceeds in the presence of an acid. As such acid, organic acids such as acetic acid, and inorganic acids such as hydrochloric acid, can suitably be used for example. The reaction can be carried out in a suitable solvent. As such solvent, any solvent which does not have a negative impact on the reaction can be used, and for example, alcohol solvents such as methanol and ethanol, organic solvents such as acetic acid, or a combination thereof can suitably be used. The reaction suitably proceeds at 0° C. to 150° C., particularly at 80° C. to 120° C.

With respect to the reaction of the compound of formula [3] and ethyl malonyl chloride, preferable examples of the nucleophilic agent include alcohols such as ethanol. The reaction suitably proceeds in the presence of a base. As such base, organic bases such as triethylamine and pyridine can suitably be used for example. The reaction can be carried out in a suitable solvent. As such solvent, any solvent which does not have a negative impact on the reaction can be used, and for example, methylene chloride, chloroform, pyridine and the like, or a combination thereof can suitably be used. The reaction suitably proceeds at −78° C. to 100° C., particularly at 0° C. to room temperature.

With respect to the reaction of the compound of formula [3] and ethyl hydrogen malonate, the reaction suitably proceeds in the presence of a condensation agent. As such condensation agent, N-ethyl-N'-(3-dimethylaminopropyl)carbodiimide hydrochloride, dicyclohexylcarbodiimide, and diisopropylcarbodiimide can suitably be used for example. The reaction can be carried out in a suitable solvent. As such solvent, any solvent which does not have a negative impact on the reaction can be used, and for example, methylene chloride, chloroform, pyridine, dimethylformamide, and N-methylpyrrolidinone and the like, or a combination thereof can suitably be used. The reaction suitably proceeds at −20° C. to 60° C., particularly at 0° C. to room temperature.

The cyclization reaction of the compound of formula [4] suitably proceeds in the presence of a base. As such base, organic bases such as dimethylaminopyridine and diisopropylethylamine, metal bases such as sodium hydride, or aqueous ammonia solution can suitably be used for example. The reaction can be carried out in a suitable solvent. As such solvent, any solvent which does not have a negative impact on the reaction can be used, and for example, alcohol solvents such as methanol and ethanol, water, dimethylformamide, dimethylacetamide, or N-methylpyrrolidone and the like, or a combination thereof can suitably be used. The reaction suitably proceeds at −78° C. to 100° C., particularly at 0° C. to room temperature.

The halogenation reaction of the compound of formula [5] can be carried out by allowing the compound to react with a halogenating agent. Examples of such halogenating agent include phosphorous oxychloride and the like. The reaction can be carried out in a suitable solvent or without a solvent. As such solvent, any solvent which does not have a negative impact on the reaction can be used, and for example, toluene, xylene and the like can preferably be used. The reaction suitably proceeds at 0° C. to 150° C., particularly at 80° C. to 120° C.

The reaction of the compound of formula [6] with the compound of formula [8] suitably proceeds in the presence of a base. In a case where the compound of formula [8] is a compound having an amino group, organic bases such as dimethylaminopyridine and diisopropylethylamine, metal bases such as sodium hydrogen carbonate and potassium carbonate, and the like can suitably be used as such base for example. In a case where the compound of formula [8] is a compound having an alcoholic hydroxyl group, metal bases such as sodium hydride, and the like can suitably be used as such base for example. In a case where the compound of formula [8] is a compound having a phenolic hydroxyl group, metal bases such as sodium hydride and cesium carbonate, and the like can suitably be used as such base for example. The reaction can be carried out in a suitable solvent. As such solvent, any solvent which does not have a negative impact on the reaction can be used, and for example, dimethylformamide, dimethylacetamide, N-methylpyrrolidone and the like, or a combination thereof can suitably be used. The reaction suitably proceeds at −78° C. to 100° C., particularly at 0° C. to room temperature.

The reaction of the compound of formula [7] with the compound of formula [9] suitably proceeds in the presence of a base. As such base, organic bases such as dimethylaminopyridine and diisopropylethylamine, metal bases such as sodium hydrogen carbonate and potassium carbonate, and the like can suitably be used as such base for example. The reaction can be carried out in a suitable solvent. As such solvent, any solvent which does not have a negative impact on the reaction can be used, and for example, dimethylformamide, dimethylacetamide, N-methylpyrrolidone and the like, or a combination thereof can suitably be used. The reaction suitably proceeds at −78° C. to 100° C., particularly at 0° C. to 100° C.

The reaction of the compound of formula [7] with the compound of formula [10] suitably proceeds in the presence of a palladium catalyst. As such palladium catalyst, palladium catalyst of 0 valent or 2 valent, such as tetrakis(triphenylphosphine)palladium (0), bis(triphenylphosphine)palladium (II) chloride, palladium (II) acetate and the like can suitably be used. In a case where L is —B(OR)$_2$ or —B(OH)$_2$, the reaction suitably proceeds in the presence of a base. As such base, metal bases such as alkali metal carbonates, alkali metal hydroxides, alkali metal phosphates and alkali metal fluorides, organic bases such as triethylamine, and the like can suitably be used for example. The reaction can be carried out in a suitable solvent or without a solvent. As such solvent, any solvent which does not have a negative impact on the reaction can be used, and for example, dimethoxyethane, tetrahydrofuran, dimethylformamide, methanol, ethanol, toluene, benzene, chloroform, water or a combination thereof can suitably be used. The reaction suitably proceeds at 60° C. to 150° C., particularly at 80° C. to 120° C.

Reduction of the compound of formula [Ia$^2$] proceeds well by a catalytic hydrogenation reaction which performs the reaction in the presence of a catalyst such as palladium, under hydrogen atmosphere. The reaction can be carried out in a suitable solvent. As such solvent, any solvent which does not have a negative impact on the reaction can be used, and for example, ester solvents such as ethyl acetate, alcohol solvents such as ethanol, ether solvents such as tetrahydrofuran, halogen solvents such as methylene chloride, or a combination thereof can be used. The reaction suitably proceeds in such solvent, under hydrogen atmosphere of 1 to 3 atm, at 0° C. to room temperature.

Preparation Method 2

Compounds of formula [I], wherein R$^1$ is hydrogen, and Y is optionally substituted alkyl, that is, compounds represented by the following:

formula [Ia$^4$] [wherein, Y$^b$ is optionally substituted alkyl, and the other symbols have the same meaning as defined above];

formula [Ia$^5$] [wherein, each symbol has the same meanings as defined above]; and formula [Ia$^6$] [wherein, each symbol has the same meanings as defined above]

can be prepared by the following preparation method.

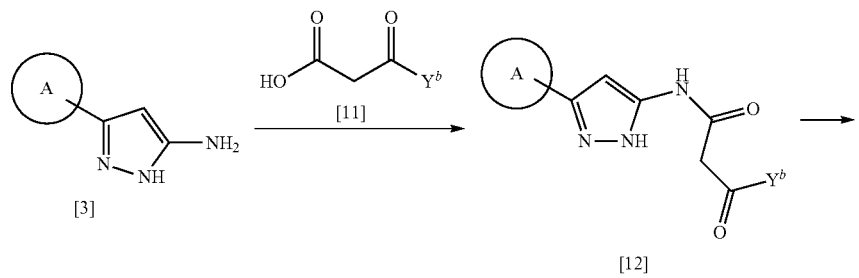

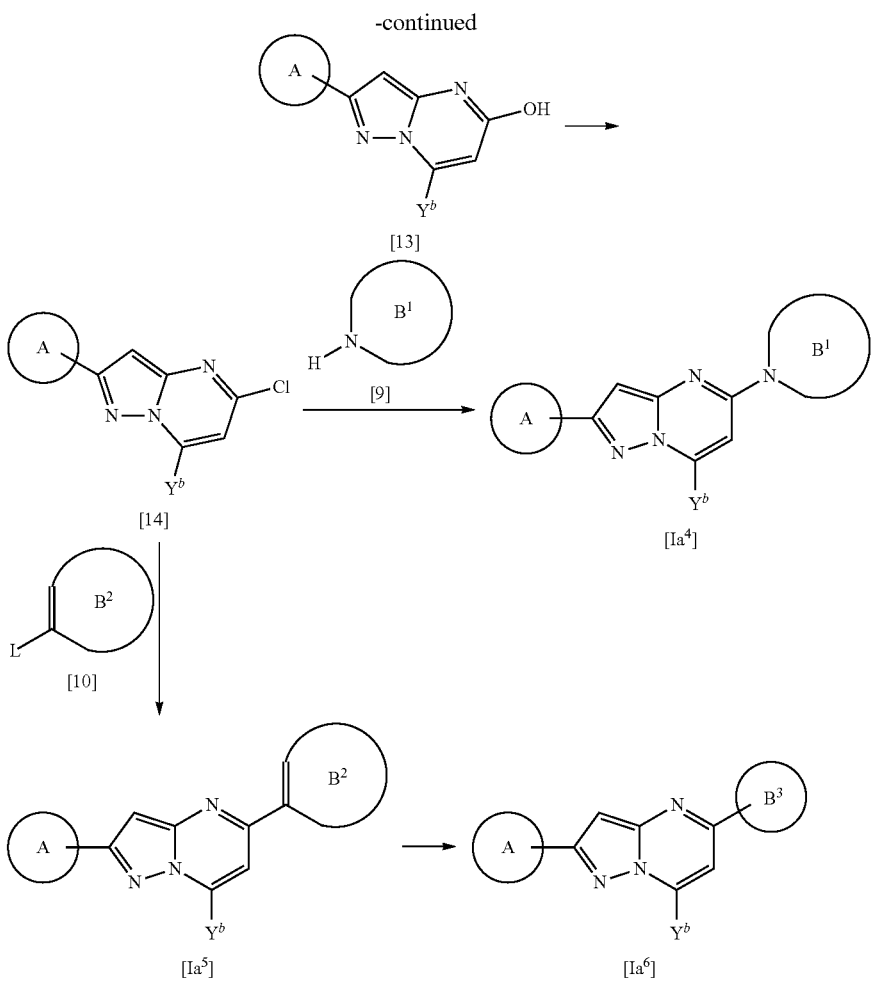

The compound of formula [3] is reacted with the compound of formula [11] [wherein, each symbol has the same meanings as defined above], followed by addition of a nucleophilic agent to provide the compound of formula [12] [wherein, each symbol has the same meanings as defined above].

The compound of formula [12] is subjected to cyclization to provide the compound of formula [13] [wherein, each symbol has the same meanings as defined above].

The compound of formula [13] is subjected to halogenation to provide the compound of formula [14] [wherein, each symbol has the same meanings as defined above].

The compound of formula [14] [wherein, each symbol has the same meanings as defined above] is reacted with the compound of formula [9] to provide the compound of formula [Ia⁴], which is optionally converted to a pharmaceutically acceptable salt.

The compound of formula [14] is reacted with the compound of formula [10] to provide the compound of formula [Ia⁵], which is optionally converted to a pharmaceutically acceptable salt.

The compound of formula [Ia⁵] is reduced to provide the compound of formula [Ia⁶], which is optionally converted to a pharmaceutically acceptable salt.

The reaction of the compound of formula [11] with the compound of formula [3] can be conducted by reacting the compound of formula [11] with a halogenating agent such as oxalyl chloride to form an acid chloride, followed by a reaction similar to the reaction of the compound of formula [3] with ethyl malonyl chloride as described in preparation method 1. The compound of formula [11] can be prepared by a usual synthetic method for a β-keto ester.

Cyclization of the compound of formula [12] suitably proceeds in the presence of a base. As such base, organic bases such as dimethylaminopyridine and diisopropylethylamine, metal bases such as sodium hydride, or an aqueous ammonia solution can suitably be used for example. The reaction can be carried out in a suitable solvent. As such solvent, any solvent which does not have a negative impact on the reaction can be used, and for example, alcohol solvents such as methanol and ethanol, water, dimethylformamide, diemthylacetamide, N-methylpyrrolidone and the like, or a combination thereof can suitably be used. The reaction suitably proceeds at −78° C. to 100° C., particularly at 0° C. to room temperature.

Halogenation of the compound of formula [13] can be conducted in a similar manner as the halogenation reaction of the compound of formula [5] described in preparation method 1.

The reaction of the compound of formula [14] with the compound of formula [9] can be conducted in a similar manner as the reaction of the compound of formula [7] with the compound of formula [9] described in preparation method 1.

The reaction of the compound of formula [14] with the compound of formula [10] can be conducted in a similar manner as the reaction of the compound of formula [7] with the compound of formula [10] described in preparation method 1.

Reduction of the compound of formula [Ia$^5$] can be conducted in a similar manner as the reduction of the compound of formula [Ia$^2$] described in preparation method 1.

Preparation Method 3

Compounds of formula [Ia$^3$] can be prepared also by the following method.

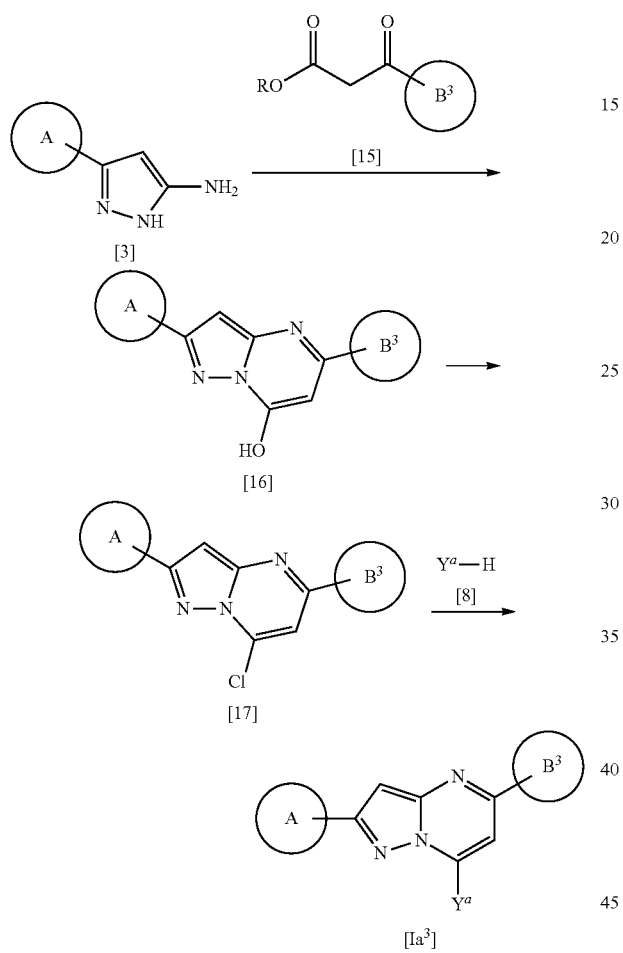

The compound of formula [3] is reacted with the compound of formula [15] [wherein, R is lower alkyl, and the other symbols have the same meaning as defined above] to provide the compound of formula [16] [wherein, each symbol has the same meanings as defined above].

The compound of formula [16] is subjected to halogenation to the compound of formula [17] [wherein, each symbol has the same meanings as defined above].

The compound of formula [17] is reacted with the compound of formula [8] to provide the compound of formula [Ia$^3$], which is optionally converted to a pharmaceutically acceptable salt.

The reaction of the compound of formula [3] with the compound of formula [15] suitably proceeds in the presence of a base. As such base, sodium alkoxide and the like can suitably be used for example. The reaction can be carried out in a suitable solvent. As such solvent, any solvent which does not have a negative impact on the reaction can be used, and for example, alcohol solvents such as methanol, ethanol and methoxyethanol, or a combination thereof can suitably be used. The reaction suitably proceeds at 60° C. to 160° C., particularly at 80° C. to 130° C.

The halogenation of the compound of formula [16] can be conducted in a similar manner as the halogenation reaction of the compound of formula [5] described in preparation method 1.

The reaction of the compound of formula [17] with the compound of formula [8] can be conducted in a similar manner as the reaction of the compound of formula [6] with the compound of formula [8] described in preparation method 1.

Preparation Method 4

Compounds of formula [I], wherein R$^1$ is other than hydrogen, that is, compounds represented by formula [Ib$^1$] [wherein, R$^{1a}$ is halogen, and the other symbols have the same meaning as defined above]; and formula [Ib$^2$] [wherein, R$^{1b}$ is lower alkyl or cyano, and the other symbols have the same meanings as defined above] can be prepared by the following preparation method.

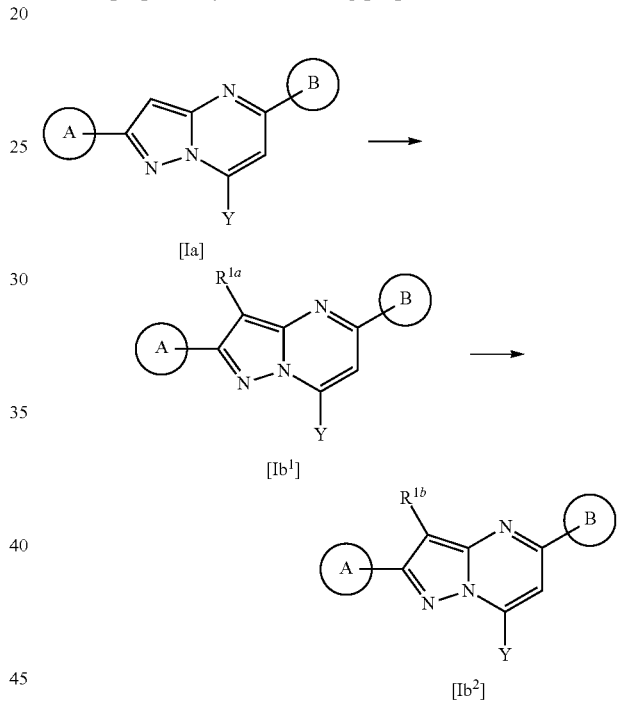

The compound of formula [Ia] is reacted with a halogenating agent to provide the compound of formula [Ib$^1$], which is optionally converted to a pharmaceutically acceptable salt.

The compound of formula [Ib$^1$] is reacted with an alkylating agent or a cyanizing agent to provide the compound of formula [Ib$^2$], which is optionally converted to a pharmaceutically acceptable salt.

Examples of the halogenating agent used in the above process to obtain the compound of formula [Ib$^1$] include N-halosuccinimide for example. The process can be carried out in a suitable solvent. As such solvent, any solvent which does not have a negative impact on the reaction can be used, and for example, halogen solvents such as chloroform and methylene chloride can suitably be used. The process suitably proceeds at 0° C. to room temperature.

The above process to obtain the compound of formula [Ib$^2$] suitably proceeds in the presence of a palladium catalyst. As such palladium catalyst, palladium catalyst of 0 valent or 2 valent, such as tetrakis(triphenylphosphine)palladium (0), bis (triphenylphosphine)palladium (II) chloride, diphenylphosphino(dppf)palladium (II) chloride, palladium (II) acetate and the like can suitably be used. As such alkylating agent used in the process, boron agents such as trimethylboroxine, and zinc agents such as dialkylzinc and alkylzinc halide can suitably be used. As such cyanizing agent used in the process, zinc cyanide and the like can suitably be used. In a case where the boron agent is used as the alkylating agent, the reaction suitably proceeds in the presence of a base. As such base, metal bases such as alkali metal carbonates, alkali metal hydroxides, alkali metal phosphates and alkali metal fluorides, organic bases such as triethylamine, and the like can suitably be used for example. The process can be carried out in a suitable solvent. As such solvent, any solvent which does not have a negative impact on the reaction can be used, and for example, dimethoxyethane, tetrahydrofuran, dimethylformamide, methanol, ethanol, toluene, benzene, chloroform, water or a combination thereof can suitably be used. The process suitably proceeds at 60° C. to 150° C., particularly at 80° C. to 120° C.

Preparation Method 5

Compounds of formula [Ia⁷] [wherein, each symbol has the same meanings as defined above] can be prepared also by the following method.

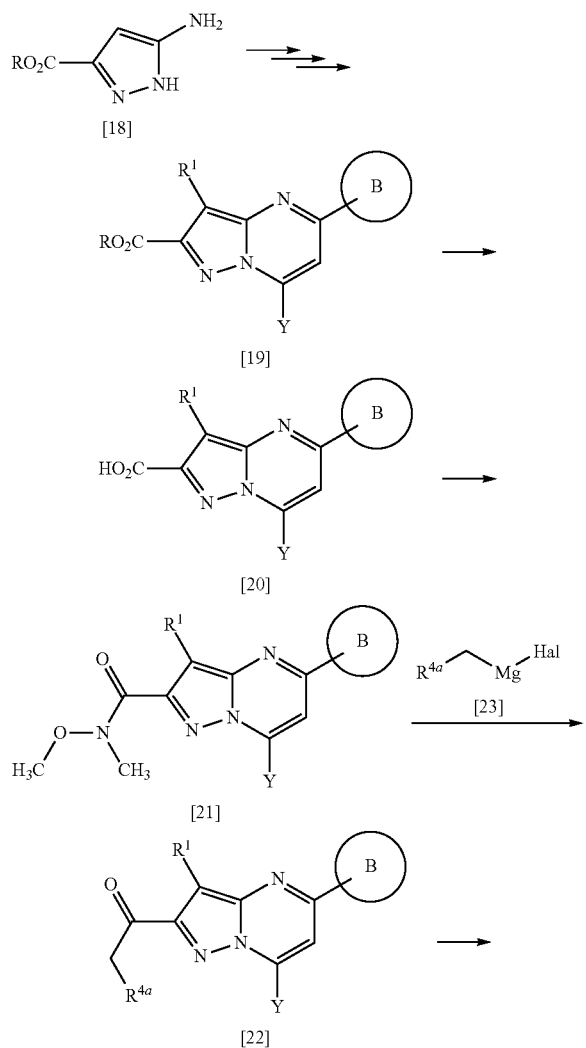

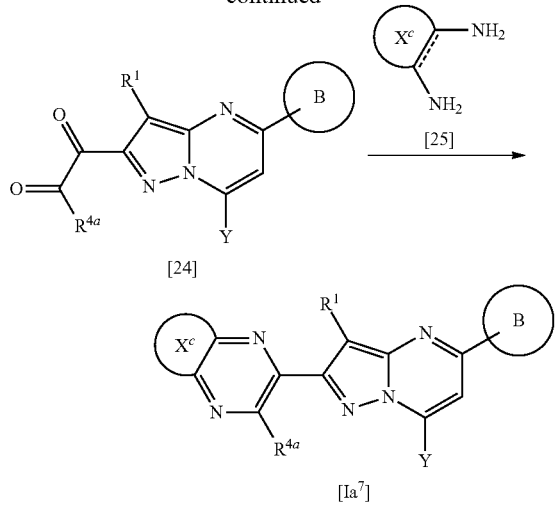

The compound of formula [19] [wherein, each symbol has the same meanings as defined above] can be obtained in a similar manner as aforementioned Preparation Method 1 to 4 from the compound of formula [18] [wherein, each symbol has the same meanings as defined above] alternative to the compound of formula [3].

The compound of formula [19] is subjected to hydrolysis to provide the compound of formula [20] [wherein, each symbol has the same meanings as defined above].

The compound of formula [20] is reacted with N,O-dimethylhydroxylamine hydrochloride to provide the compound of formula [21] [wherein, each symbol has the same meanings as defined above].

The compound of formula [21] is reacted with the compound of formula [23] [wherein, Hal is a halogen, and each symbol has the same meanings as defined above] to provide the compound of formula [22] [wherein, each symbol has the same meanings as defined above].

The compound of formula [22] is subjected to oxidation to provide the compound of formula [24] [wherein, each symbol has the same meanings as defined above].

The compound of formula [24] is reacted with the compound of formula [25] [wherein ═══ is single bond or double bound, and each symbol has the same meanings as defined above] to provide the compound of formula [Ia⁷] [wherein, each symbol has the same meanings as defined above].

The hydrolysis of the compound of formula [19] suitably proceeds in the presence of a base. As such base include alkali metal hydroxide, and for example sodium hydroxide, potassium hydroxide, and the like. The process can be carried out in a suitable solvent. As such solvent, any solvent which does not have a negative impact on the reaction can be used, and for example, water; alcohol such as methanol, ethanol and the like; ether such as tetrahydrofuran, dioxane, and the like or the mixture thereof can suitably be used. The process suitably proceeds at 0° C. to room temperature.

The reaction of compound of formula [20] with N,O-dimethylhydroxylamine hydrochloride suitably proceeds in presence of condensation agent such as carbodiimide reagent (as such the carbodiimide reagent includes dicyclohexylcarbodiimide, 1-ethyl-3-(3-dimethylaminopropyl)carbodiimide and the like), phosphoric reagent (as such the phosphoric reagent includes diethyl cyanophosphate and the like), or acid halide regent (as such acid halide reagent includes alkyl chlorocarobonete and the like). The process can be carried out in presense of base such as triethylamine. The process can be carried out in a suitable solvent. As such solvent, any solvent which does not have a negative impact on the reaction can be used, and for example, halogen solvents such as chloroform and methylene chloride can suitably be used. The process suitably proceeds at 0° C. to room temperature.

The reaction of compound of formula [21] with compound of formula [23] suitably proceeds in a suitable solvent. As such solvent, any solvent which does not have a negative impact on the reaction can be used, and for example, ether such as tetrahydrofuran, dioxane and the like can suitably be used. The process suitably proceeds at −78° C. to room temperature. The process can be carried out in a suitable solvent. As such solvent, any solvent which does not have a negative impact on the reaction can be used, and for example, tetrahydrofuran, dioxane and the like can suitably be used. can suitably be used. The process suitably proceeds at 0° C. to room temperature.

The oxidation of compound of formula [22] suitably proceeds in presense of oxidizing reagent. As such oxidizing reagent, sodium nitrite can suitably be used. The process can be carried out in presense of acid such as conc hydrochloric acid. The process can be carried out in a suitable solvent. As such solvent, any solvent which does not have a negative impact on the reaction can be used, and for example, tetrahydrofuran, dioxane and the like can suitably be used. The process suitably proceeds at 0° C. to room temperature.

The reaction of compound of formula [24] with compound of formula [25] suitably proceeds in a suitable solvent. As such solvent, any solvent which does not have a negative impact on the reaction can be used, and for example, water; alcohol such as methanol, ethanol and the like or the mixture thereof can suitably be used. The process suitably proceeds at 0° C. to room temperature. When ==== of formula [25] is single bond, the compound of formula [Ia$^7$] can be obtained by the oxidation reaction in a convention manner after the aforementioned reaction of compound of formula [24] with compound of formula [25].

Raw material compounds in the above preparation schemes (Preparation Methods 1 to 4) can be prepared by procedures known in the art and/or recited in Reference Examples described hereinafter.

Also, compounds of formula [I] prepared by the above preparation schemes (Preparation Methods 1 to 4) can be allowed to structural conversion into the other compounds of formula [I] by the procedures recited in Examples described hereinafter and/or known in the art, or a combination thereof.

In a case where the compound of the present invention, synthetic intermediates, or raw material compounds have a functional group (hydroxyl group, amino, carboxy), the reaction can be carried out by protecting the functional group with a protecting group usually used in organic synthetic chemistry, such as those described in Greene's Protecting Group in Organic Synthesis, and then the protecting group can be removed to give the target compound.

The compounds of the present invention or raw material compounds thereof can be isolated and purified as the free form (free base or free acid) or as the salt thereof. The salt can be prepared by salt formation treatments usually employed. For instance, the salt formation treatment can be carried out by adding an acid or a base or the solution thereof to the solution or suspension of the compound of the present invention. Preferable acid is a pharmaceutically acceptable salt, which includes hydrochloric acid, sulfuric acid, nitric acid, phosphoric acid, hydrobromic acid, acetic acid, fumaric acid, oxalic acid, citric acid, methanesulfonic acid, benzenesulfonic acid, p-toluenesulfonic acid and maleic acid. Preferable base is a pharmaceutically acceptable salt, which includes alkali metal salts such as sodium salts and potassium salts; and alkaline earth metal salts such as calcium salts. A solvent of the solution or suspension of the compound of the present invention may be any solvent which does not have a negative impact on the salt formation treatment. Examples include water; alcohol such as methanol, ethanol, and propanol; ester such as ethyl acetate; ether such as diethyl ether, dioxane, and tetrahydrofuran; dichrormethane; and chloroform, or a combination thereof.

The isolation and purification can be carried out by usual chemical procedures such as extraction, concentration, crystallization, filtration, recrystallization and various chromatography.

The compounds of formula [I] or a pharmaceutically acceptable salt thereof according to the present invention possess excellent PDE10 inhibitory activity, that is, inhibitory activity on the enzyme activity of phosphodiesterase 10 (PDE10, more specifically PDE10A), in mammals. The compounds of formula [I] or a pharmaceutically acceptable salt thereof according to the present invention are also highly selective for PDE10.

Also, the compounds of formula [I] or a pharmaceutically acceptable salt thereof in the present invention exhibit various pharmacological efficacies through their PDE10 inhibitory activity. Accordingly, a pharmaceutical composition comprising the compounds of formula [I] or a pharmaceutically acceptable salt thereof as an active ingredient can be used to inhibit PDE10 activity. Further, said pharmaceutical composition can be used for the treatment or prophylaxis of diseases or conditions which are expected to be ameliorated by inhibition of PDE10 activity.

As a disease or condition which is expected to be ameliorated by inhibition of PDE10 activity, there may be mentioned, for example:

Psychotic Disorder Such as Schizophrenia:
for example, schizophrenia, schizophreniform disorder, delusional disorder, schizoaffective disorder, substance-induced psychotic disorder, paranoid or schizoid personality disorder, etc;

Anxiety Disorder:
for example, panic disorder, agoraphobia, specific phobia, social phobia, obsessive-compulsive disorder, post-traumatic stress disorder, acute stress disorder, generalized anxiety disorder, etc;

Drug Addiction:
for example, addiction to alcohol, amphetamine, cocaine, or opiate, etc;

Disorders Comprising Deficient Cognition as a Symptom:
for example, dementia (including Alzheimer's disease, multi-infarct dementia, etc.), delirium, amnestic disorder, post-traumatic stress disorder, mental retardation, a learning disorder, attention deficit hyperactivity disorder (ADHD), age-related cognitive decline, etc; and Mood Disorder:
for example major depressive disorder, dysthymic disorder, minor depressive disorder, bipolar disorder (including bipolar I disorder, bipolar II disorder), cyclothymic disorder, etc; or Mood Episode:
for example, major depressive episode, manic or mixed episode, hypomanic episode, etc.

Of these diseases and conditions, one may wish to focus on treating the following diseases by using the compounds of the invention:

Schizophrenia:

Anxiety Disorder:
for example, panic disorder, social phobia, obsessive-compulsive disorder, post-traumatic stress disorder, generalized anxiety disorder;

Drug Addiction:

Disorders comprising deficient cognition as a symptom:
for example, dementia (including Alzheimer's disease, etc.), learning disorder, attention deficit hyperactivity disorder (ADHD) and age-related cognitive decline; and Mood Disorder:
for example, major depressive disorder, dysthymic disorder, minor depressive disorder, bipolar disorder.

Of these diseases and conditions, one may wish to focus particularly on treating the following diseases by using the compounds of the invention:

Schizophrenia:

Anxiety Disorder:
for example, panic disorder, social phobia, obsessive-compulsive disorder, post-traumatic stress disorder, generalized anxiety disorder; and Mood Disorder:
for example, major depressive disorder, dysthymic disorder, minor depressive disorder, bipolar disorder.

One may wish to focus more particularly on treating schizophrenia by using the compounds of the invention.

In addition, the compounds of the invention may be used to treat a disease or condition which is expected to be ameliorated by inhibition of PDE10 activity, including for example;
movement disorder or neurodegenerative disorder including dyskinesia associated with dopamine agonist therapy;
Huntington's disease;
Parkinson's disease; and
restless leg syndrome.

In addition, the compounds of the invention may be used to treat a disease or condition which is expected to be ameliorated by inhibition of PDE10 activity, including for example, cancer.

In addition, the compounds of the invention may be used to treat a disease or condition which is expected to be ameliorated by inhibition of PDE10 activity, including for example;
type 1 or type 2 diabetes (or non-insulin dependent diabetes (NIDDM));
impaired glucose tolerance (IGT);
impaired fasting glucose (IGF);
metabolic syndrome; and
metabolism related disorders including excess of body weight or excess of body fat in obese patient.

Also within the scope of this invention is a method for treating or preventing a disease or condition by administering to a patient (or a subject) in need thereof an effective amount of a compound of formula [I] or a pharmaceutically acceptable salt thereof.

Also, use of a compound of formula [I] or a pharmaceutically acceptable salt thereof for the manufacture of a medicament are also encompassed within a scope of the present invention.

Inhibitory action on PDE10 and pharmacological effects of the compounds of the present invention can be confirmed by known methods and equivalent methods thereto.

For example, measurements of PDE10 inhibitory activities can be carried out by the method described below in Experimental Example 1 or by methods disclosed in literature. See for example, Fujishige et al., Eur. J. Biochem., vol. 266, pp. 1118-1127, 1999, and Mukai et al., Br. J. Pharmacol., vol. 111, pp. 389-390, 1994.

Further, selectivity of the compounds described herein for PDE10 may be evaluated by using the methods disclosed in the literature. See for example, Kotera et al., Biochem. Pharmacol., vol. 60, pp. 1333-1341, 2000; Sasaki et al., Biochem. Biophys. Res. Commun., vol. 271, pp. 575-583, 2000; Yuasa et al., Journal of Biological Chemistry, vol. 275, pp. 31469-31479, 2000; Gamanuma et al., Cellular Signaling, vol. 15, pp. 565-574, 2003.

Pharmacological effects on the symptoms of schizophrenia can be detected by the following in vivo test systems using mouse or rat.

MK-801-induced locomotor activity:
[O'Neil and Shaw, Psychopharmacology, 1999, 145:237-250].

Apomorphine-induced locomotor activity:
[Geyer et al., Pharmacol. Biochem. Behav., 1987, 28:393-399; Ellenbroek, Pharmacol. Ther., 1993, 57:1-78].

Conditioned avoidance response:
[Moor et al., J. Pharmacol. Exp. Ther., 1992, 262:545-551].

Pharmacological effects to improve the deficient cognition in schizophrenia etc can be detected by the following in vivo test systems using mouse or rat.

MK-801-induced Isolation rearing Prepulse inhibition (PPI) deficit:
[Mansbach and Geyer, Neuropsychopharmacology, 1989, 2:299-308; Bakshi et al., J. Pharmacol. Exp. Ther., 1994, 271:787-794; Bubenikova et al., Pharmacol. Biochem. Behav., 2005, 80:591-596].

Isolation rearing-induced Prepulse inhibition (PPI) deficit:
[Cilia et al., Psychopharmacology, 2001, 156:327-337].

MK-801-induced deficit in Novel object recognition task (NOR):
[Karasawa et al., Behav. Brain. Res., 2008, 186:78-83].

The compounds of formula [I] or a pharmaceutically acceptable salt thereof can be formulated into a conventional pharmaceutical preparation such as a tablet, granule, capsule, powder, solution, suspension, emulsion, inhalent, injectibles and drops, etc, by mixing the compound(s) with an inert pharmaceutically acceptable carrier suitable for each administration route.

Examples of such carriers include any conventional pharmaceutically acceptable materials, such as binders (gum Alabicum, gelatin, sorbitol, polyvinylpyrrolidone, etc.), excipients (lactose, sucrose, corn starch, sorbitol, etc.), lubricants (magnesium stearate, talc, polyethyleneglycol, etc.), disintegrators (potato starch, etc.) and the like.

In case of injectibles and drops, the compounds of the present invention can be mixed with distilled water for injection, physiological saline, aqueous glucose solution and the like.

The administration route of the compounds of formula [I] or a pharmaceutically acceptable salt thereof is not limited to particular route. They can be administered orally or parenterally (for example, through intravenous, intramuscular, subcutaneous, transdermal, transnasal, transmucosal or enteral route).

Further, in case of treating a central nervous system (CNS) disease, the drug can be directly or indirectly introduced into the brain, by bypassing the blood-brain barrier (BBB). Examples of those methods include intracerebroventricular (i.c.v.) administration, and an administration method accompanying intravenous injection of hypertonic solution which enables temporary opening of the BBB (osmotic opening).

When a compound of formula [I] or a pharmaceutically acceptable salt thereof is used for medical use, the dosage of the compound may be determined in accordance with the potency or property of that compound, to establish a dosage range which is effective enough for achieving the desired pharmacological efficacy. The dosage may vary depending on the administration route, age, bodyweight, and condition of the patient. A usual dosage range will be, for example, a range of 0.001 to 300 mg/kg per day, preferably a range of 0.001 to 30 mg/kg per day.

The method of treatment or prophylaxis using a compound of the present invention is applied to a human. However, it may also be applied to mammals other than a human.

Hereinafter, the present invention is illustrated in more detail by the following Examples. The examples are given to illustrate the invention, but should not be construed to limit it. Reference is made to the claims for determining what is reserved to the inventors.

EXAMPLES

Experimental Example 1

Measurement of PDE10 Inhibitory Activity (1) Bovine PDE10A (bPDE10A) was isolated and prepared from bovine corpus striatum, according to the methods described in the reference Fujishige et al., Eur. J. Biochem., vol. 266, pp. 1118-1127, 1999. Human PDE10A (hPDE10A) was isolated from COS-7 cells transfected with plasmids coding for human PDE10A2, according to the methods described in the reference Kotera et al., Biochem. Biophys. Res. Commun., vol. 261, pp. 551-557, 1999. The enzyme solutions obtained were used for a PDE assay.

The PDE assay was performed according to a modified method referred to a report of Kotera et al. (Kotera et al., Biochem. Pharmacol., vol. 60, pp. 1333-1341, 2000), by the radiolabeled nucleotide method.

Specifically, the measurements of the inhibitory activities were carried out in the following method.

(Method) The test compounds were dissolved in dimethyl sulfoxide (DMSO). 2 μL of the compound solution was added to 96 well plate, and the reaction mixture (20 μL of PDE enzyme solution in 50 mM Tris-HCl, pH 8.0, 40 μL of the assay buffer (50 mM Tris-HCl, pH 8.0, 2 mM $MgCl_2$, 0.07% 2-mercaptoethanol, and 0.825 mg/mL bovine serum albumin), and 20 μL of 1 mg/mL snake venom in 50 mM Tris-HCl, pH8.0) was added to the 96 well plate. The enzyme reaction was started by adding and mixing with substrate solution of 20 μL containing approximate 35 nM $^3$H-cAMP in 50 mM Tris-HCl, pH 8.0. The final concentration of cAMP in the reaction mixtures was 7 nM. The reaction mixtures were incubated at room temperature for 90 min. After incubation, the reaction was stopped by adding 100 μL of methanol and resultant solutions were applied to filter plate containing Dowex (1×8 200-400) and centrifuged. 50 μL of the eluate together with wash eluate with additional 100 μL methanol was collected in another plate and the radioactivity was measured.

(2) The compounds in the Examples below were tested for PDE inhibition using the Method described above.

They showed an $IC_{50}$ value of 30 nM or less. The $IC_{50}$ values of some preferred compounds are given in the following table I and II.

TABLE I

| Example No | $IC_{50}$ (nM) |
| --- | --- |
| 1.001 (HCl) | 0.11 |
| 1.002 (3/2 HCl) | 0.0045 |
| 1.003 (HCl) | 0.83 |
| 1.006 | 0.090 |
| 1.009 | 0.20 |
| 1.010 (HCl) | 0.38 |
| 1.011 | 0.22 |
| 1.013 | 0.090 |

TABLE I-continued

| Example No | $IC_{50}$ (nM) |
| --- | --- |
| 1.019 | 0.57 |
| 1.027 | 0.13 |
| 1.031 | 0.052 |
| 1.047 | 0.045 |
| 1.050 | 0.019 |
| 1.058 | 0.65 |
| 1.059 | 0.32 |
| 1.062 | 0.87 |
| 1.081 | 0.39 |
| 1.085 | 0.18 |
| 1.097 | 0.035 |
| 1.109 | 0.78 |
| 1.111 | 0.46 |
| 1.112 | 0.0085 |
| 1.114 | 0.044 |
| 1.123 | 0.15 |
| 1.126 | 0.17 |
| 1.133 | 0.23 |
| 1.144 (Free) | 0.48 |
| 1.147 | 0.39 |
| 1.152 | 0.0068 |
| 1.154 | 1.08 |
| 2.001 | 0.36 |

* These results were obtained by using PDE10A of bovine.

TABLE II

| Example No | $IC_{50}$ (nM) |
| --- | --- |
| 1.173 | 0.27 |
| 1.175 | 0.12 |
| 1.181 | 0.64 |
| 1.184 | 2.5 |
| 1.187 | 0.60 |
| 1.189 | 0.18 |
| 1.190 | 0.69 |
| 1.197 | 2.5 |
| 1.198 | 0.82 |
| 1.199 | 0.89 |
| 5.001 | 0.15 |
| 5.002 | 0.28 |

* These results were obtained by using PDE10A of human

Example 1.001

(a)

Method A: Preparation was performed in a similar manner as described in *Helv. Chim. Acta.* 2001, 84, 2379).

Method B: A suspension of 3-chloroquinoxaline-2-carboxylate (86.0 g, 363 mmol), trimethylboroxine (22.8 g, 0.182 mmol), [1,1'-bis(diphenylphosphino)ferrocene]dichloropalladium(II) (8.90 g, 11.0 mmol), and potassium carbonate (100 g, 727 mmol) in 1,4-dioxane (726 mL) was heated at 115° C. for 4 h. And then trimethylboroxine (22.8 g, 0.182 mmol) was added again and heated at same temperature for 2 h. After being cooled to ambient temperature, the reaction mixture was diluted with ethyl acetate (700 mL) and filtrated through celite with ethyl acetate (1000 mL). The filtrate was combined and concentrated in vacuo. The residue was purified by silica gel column chromatography (silica gel 900 g, hexane:ethyl acetate=9:1 to 17:3) followed by recrystallization from cold hexane to give ethyl 3-methylquinoxaline-2-carboxylate. MS (APCI): m/z 217 (M+H).

(b)

To a suspension of potassium tert-butoxide (72.7 g, 647 mmol) in toluene (810 mL) was added a solution of ethyl 3-methylquinoxaline-2-carboxylate (70.0 g, 324 mmol) and acetonitrile (38.3 mL, 809 mmol) in toluene (270 mL) dropwise over 50 min at 5° C. After being stirred for 5 min at 0° C., water (585 mL) was added. The organic layer was extracted with water (100 mL) and the aqueous layer was combined and acidified to pH 3-4 with 10% aqueous hydrochloric acid. The resulting precipitate was collected and dissolved to tetrahydrofuran. And then the organic layer was dried over sodium sulfate, filtrated and concentrated in vacuo. The crude solid was purified by silica gel column chromatography (silica gel 2.2 kg, chloroform to chloroform:ethyl acetate=19:1) to give 3-(3-methylquinoxalin-2-yl)-3-oxopropanenitrile. MS (APCI): m/z 212 (M+H).

(c)

A suspension of 3-(3-methylquinoxalin-2-yl)-3-oxopropanenitrile (45.8 g, 217 mmol) and hydrazine monohydrate (15.8 mL, 325 mmol) in acetic acid (109 mL) and ethanol (1083 mL) was refluxed for 17 h. After being cooled to ambient temperature, the reaction mixture was diluted with water (360 mL) and basified to pH 8 with sodium bicarbonate. The resulting precipitate was collected and washed with diisopropyl ether. The crude was diluted with methanol (1077 mL) and potassium carbonate (29.9 g), and then heated at 60° C. for 2 h. The precipitate was collected and washed with diisopropyl ether to give 3-(3-methylquinoxalin-2-yl)-1H-pyrazol-5-amine. MS (APCI): m/z 226 (M+H).

(d)

Method A: To a solution of 3-(3-methylquinoxalin-2-yl)-1H-pyrazol-5-amine (5.00 g, 22.2 mmol) in N,N-dimethylacetamide (111 mL) was added ethyl malonyl chloride (5.68 mL, 44.4 mmol) and pyridine (37.2 mL, 45.9 mmol) at 0° C. After being stirred for 3 h, the reaction mixture was diluted with ethanol (118 mL), and stirred at room temperature for 18 h. After adding water (260 mL), the resulting precipitate was collected and washed with water to give ethyl 3-{[3-(3-methylquinoxalin-2-yl)-1H-pyrazol-5-yl]amino}-3-oxopropanoate. MS (APCI): m/z 340 (M+H).

Method B: To a suspension of 3-(3-methylquinoxalin-2-yl)-1H-pyrazol-5-amine (5.00 g, 22.2 mmol) and ethyl hydrogen malonate (2.88 mL, 24.4 mmol) in pyridine (89 mL) was added N-ethyl-N'-(3-dimethylaminopropyl)carbodiimide hydrochloride (6.38 g, 33.3 mmol) at 0° C. and stirred for 30 min. The reaction mixture was stirred for 1 h at room temperature and then concentrated in vacuo. The residue was diluted with water (100 mL) and the resulting precipitate was collected and washed with water followed by diethyl ether to give ethyl 3-{[3-(3-methylquinoxalin-2-yl)-1H-pyrazol-5-yl]amino}-3-oxopropanoate. MS (APCI): m/z 340 (M+H).

(e)

Method A (free form): A suspension of ethyl 3-{[3-(3-methylquinoxalin-2-yl)-1H-pyrazol-5-yl]amino}-3-oxopropanoate (20.0 g, 58.9 mmol) in 28% aqueous ammonia (295 mL) and methanol (1176 mL) was stirred overnight at room temperature, and then concentrated in vacuo. The residue was diluted with water (1500 mL) and ethyl acetate (1000 mL). The aqueous layer was concentrated in vacuo, and water (40 mL) was added. The mixture was acidified to pH 5-6 with 10% aqueous hydrochloric acid, and then ethanol (360 mL) was added. The resulting precipitate was collected and washed with 95% aqueous ethanol and ethanol to give 2-(3-methylquinoxalin-2-yl)pyrazolo[1,5-a]pyrimidine-5,7-diol. MS (ESI): m/z 292 (M−H).

Method B (DMAP salt): A suspension of ethyl 3-{[3-(3-methylquinoxalin-2-yl)-1H-pyrazol-5-yl]amino}-3-oxopropanoate (1.00 g, 2.95 mmol) and 4-dimethylaminopyridine (DMAP) (1.08 g, 8.84 mmol) in water (7 mL), tetrahydrofuan (7 mL), and methanol (7 mL) was heated at 65° C. for 4 h. After being cooled to ambient temperature, the reaction mixture was diluted with water and ethyl acetate. The aqueous layer was collected and concentrated in vacuo. The residue was triturated with ether acetate to give 2-(3-methylquinoxalin-2-yl)pyrazolo[1,5-a]pyrimidine-5,7-diol DMAP salt. MS (APCI): m/z 294 (M+H).

(f)

A suspension of 2-(3-methylquinoxalin-2-yl)pyrazolo[1,5-a]pyrimidine-5,7-diol (2.98 g, 6.95 mmol) in phosphorous oxychloride (10.7 mL) was heated at 100° C. for 1 h. After being cooled to ambient temperature, the reaction mixture was concentrated in vacuo. The residue was poured into aqueous potassium carbonate solution, and then precipitate was collected and washed with water to give 3-(5,7-dichloropyrazolo[1,5-a]pyrimidin-2-yl)-2-methylquinoxaline. MS (APCI): m/z 330/332 (M+H).

(g)

To a suspension of 3-(5,7-dichloropyrazolo[1,5-a]pyrimidin-2-yl)-2-methylquinoxaline (991 mg, 3.00 mmol), 4-aminotetrahydropyran (364 mg, 3.60 mmol), and triethylamine (1.25 mL, 9.00 mmol) in N,N-dimethylformamide (30 mL) was stirred for 2 h at room temperature. After being cooled to 0° C., the reaction mixture was diluted with water. The resulting precipitate was collected and purified by silica gel column chromatography (silica gel 200 g, chloroform to chloroform: ethyl acetate=1:1) to give 5-chloro-2-(3-methylquinoxalin-2-yl)-N-(tetrahydro-2H-pyran-4-yl)pyrazolo[1,5-a]pyrimidin-7-amine. MS (APCI): m/z 395/397 (M+H).

(h)

A suspension of 5-chloro-2-(3-methylquinoxalin-2-yl)-N-(tetrahydro-2H-pyran-4-yl)pyrazolo[1,5-a]pyrimidin-7-amine (620 mg, 1.57 mmol) in pyrrolidine (12 mL) was heated at 80° C. for 3 h. Then the reaction mixture was poured into cold water. The resulting precipitate was collected and washed with water to give 2-(3-methylquinoxalin-2-yl)-5-pyrrolidin-1-yl-N-(tetrahydro-2H-pyran-4-yl)pyrazolo[1,5-c]pyrimidin-7-amine. MS (APCI): m/z 430 (M+H).

(i)

To a suspension of 2-(3-methylquinoxalin-2-yl)-5-pyrrolidin-1-yl-N-(tetrahydro-2H-pyran-4-yl)pyrazolo[1,5-a]pyrimidin-7-amine (655 mg, 1.52 mmol) in ethanol (15 mL) was added 2N aqueous hydrochloric acid solution (0.915 mL). The mixture was heated at 80° C. for 3 h, and then water (3.1 mL) and ethanol (5.0 mL) was added. The mixture was clear solution and then cooled to ambient temperature to give 2-(3-methylquinoxalin-2-yl)-5-pyrrolidin-1-yl-N-(tetrahydro-2H-pyran-4-yl)pyrazolo[1,5-a]pyrimidin-7-amine hydrochloride (the compound of Example 1.001 listed in the Table of Examples as described hereinafter). $^1$H-NMR (500 MHz, DMSO-d$_6$): δ 1.86-1.91 (4H, m), 2.04-2.06 (4H, m), 3.08 (3H, s), 3.46-3.53 (2H, m), 3.63 (4H, m), 3.94 (2H, m), 4.09

(1H, m), 5.62 (1H, s), 6.87 (1H, s), 7.83-7.90 (2H, m), 8.08 (1H, dd, J=8.2, 1.4 Hz), 8.14 (1H, dd, J=8.0, 1.3 Hz), 8.20 (1H, br).

The preparation of the dihydrochloride salt was also performed in the similar manner by using excess amount of aqueous hydrochloric acid solution.

Example 1.002

(a)

The preparation was performed in a similar manner as Example 1.001 (g) from 3-(5,7-dichloropyrazolo[1,5-a]pyrimidin-2-yl)-2-methylquinoxaline (200 mg, 0.606 mmol) and N-methyl-4-aminotetrahydropyran (84 mg, 0.729 mmol) to give 5-chloro-N-methyl-2-(3-methylquinoxalin-2-yl)-N-(tetrahydro-2H-pyran-4-yl)pyrazolo[1,5-c]pyrimidin-7-amine. MS (APCI): m/z 409/411 (M+H).

(b)

The preparation was performed in a similar manner as Example 1.001(h) from 5-chloro-N-methyl-2-(3-methylquinoxalin-2-yl)-N-(tetrahydro-2H-pyran-4-yl)pyrazolo[1,5-a]pyrimidin-7-amine (100 mg, 0.245 mmol) to give N-methyl-2-(3-methylquinoxalin-2-yl)-5-pyrrolidin-1-yl-N-(tetrahydro-2H-pyran-4-yl)pyrazolo[1,5-c]pyrimidin-7-amine. MS (APCI): m/z 444 (M+H).

(c)

The preparation was performed in a similar manner as Example 1.001 (i) from N-methyl-2-(3-methylquinoxalin-2-yl)-5-pyrrolidin-1-yl-N-(tetrahydro-2H-pyran-4-yl)pyrazolo[1,5-a]pyrimidin-7-amine (692 mg, 1.53 mmol) to give N-methyl-2-(3-methylquinoxalin-2-yl)-5-pyrrolidin-1-yl-N-(tetrahydro-2H-pyran-4-yl)pyrazolo[1,5-c]pyrimidin-7-amine hydrochloride (the compound of Example 1.002 listed in the Table of Examples as described hereinafter). $^1$H-NMR (500 MHz, DMSO-$d_6$): δ 1.78-1.81 (2H, m), 1.98-2.07 (6H, m), 3.10 (3H, s), 3.13 (3H, s), 3.63 (4H, br), 3.39-3.44 (2H, m), 3.99 (2H, dd, J=11.2, 4.5 Hz), 5.24 (1H, m), 5.46 (1H, s), 7.02 (1H, s), 7.85-7.89 (2H, m), 8.05-8.07 (1H, m), 8.13-8.15 (1H, m).

The preparation of the 3/2 hydrochloride salt was also performed in the similar manner by using excess amount of aqueous hydrochloric acid solution.

Example 1.003

(a)

To a suspension of 5-chloro-2-(3-methylquinoxalin-2-yl)-N-(tetrahydro-2H-pyran-4-yl)pyrazolo[1,5-a]pyrimidin-7-amine (Example 1.001 (g)) (4.26 g, 10.8 mmol), (R)-3-fluoropyrrolidine hydrochloride (13.7 g, 108 mmol), and diisopropylethylamine (20.7 g, 160 mmol) in N-methyl-2-pyrrolidinone (108 mL) was heated 80° C. for 3 days. After being cooled to ambient temperature, the reaction mixture was poured into water. The mixture was extracted with ethyl acetate, and the organic layer was washed with water and saturated brine, dried over sodium sulfate, filtrate, and concentrated in vacuo. The residue was purified by silica gel column chromatography (silica gel 800 g, hexane:ethyl acetate=1:1 to ethyl acetate) to give 5-[(3R)-3-fluoropyrrolidin-1-yl]-2-(3-methylquinoxalin-2-yl)-N-(tetrahydro-2H-pyran-4-yl)pyrazolo[1,5-a]pyrimidin-7-amine. MS (APCI): m/z 448 (M+H).

(b)

The preparation was performed in a similar manner as Example 1.001 (i) from 5-[(3R)-3-fluoropyrrolidin-1-yl]-2-(3-methylquinoxalin-2-yl)-N-(tetrahydro-2H-pyran-4-yl) pyrazolo[1,5-a]pyrimidin-7-amine (4.15 g, 9.27 mmol) to give 5-[(3R)-3-fluoropyrrolidin-1-yl]-2-(3-methylquinoxalin-2-yl)-N-(tetrahydro-2H-pyran-4-yl)pyrazolo[1,5-a]pyrimidin-7-amine hydrochloride (the compound of Example 1.003 listed in the Table of Examples as described hereinafter). $^1$H-NMR (500 MHz, DMSO-$d_6$): δ 1.83-1.94 (4H, m), 2.21-2.45 (2H, m), 3.08 (3H, s), 3.47-3.52 (1H, m), 3.66-3.72 (1H, m), 3.80-4.14 (4H, m), 5.58 (1H, m), 5.66 (1H, s), 6.88 (1H, s), 7.83-7.90 (2H, m), 8.07 (1H, m), 8.14 (1H, m), 8.19 (1H, br).

The preparation of the dihydrochloride salt was also performed in the similar manner by using excess amount of aqueous hydrochloric acid solution.

Example 1.004

(a)

Preparation was performed in a similar manner as Example 1.001 (a). To a solution of tert-butyl (E)-[(1E)-1-ethyl-3-methoxy-3-oxoprop-1-en-1-yl]diazenecarboxylate (see *Synlett*. 2003, 8, 1183; 1.50 g, 6.19 mmol) in tetrahydrofuran (30 mL) was added 1,2-phenylenediamine (683 mg, 6.19 mmol) at room temperature. After being stirred for 22 hour, the reaction mixture was poured into water and extracted with ethyl acetate. The organic layer was combined and dried over magnesium sulfate, filtrated and concentrated in vacuo. The residue was purified by silica gel column chromatography (hexane to hexane:ethyl acetate=6:1) to give ethyl 3-ethylquinoxaline-2-carboxylate. MS (APCI): m/z 217 (M+H).

(b)

The preparation was performed in a similar manner as Example 1.001 (b) from ethyl 3-ethylquinoxaline-2-carboxylate (2.37 g, 10.3 mmol) to give 3-(3-ethylquinoxalin-2-yl)-3-oxopropanenitrile. MS (APCI): m/z 226 (M+H).

(c)

The preparation was performed in a similar manner as Example 1.001 (c) from 3-(3-ethylquinoxalin-2-yl)-3-oxopropanenitrile (1.00 g, 9.01 mmol) to give 3-(3-ethylquinoxalin-2-yl)-1H-pyrazol-5-amine. MS (APCI): m/z 240 (M+H).

(d)

The preparation was performed in a similar manner as Example 1.001 (d) method A from 3-(3-ethylquinoxalin-2-yl)-1H-pyrazol-5-amine (1.41 g, 5.89 mmol) to give ethyl 3-{[3-(3-ethylquinoxalin-2-yl)-1H-pyrazol-5-yl]amino}-3-oxopropanoate. MS (APCI): m/z 354 (M+H).

(e)

The preparation was performed in a similar manner as Example 1.001 (e) method A from ethyl 3-{[3-(3-ethylquinoxalin-2-yl)-1H-pyrazol-5-yl]amino}-3-oxopropanoate (1.70 g, 4.81 mmol) to give 2-(3-ethylquinoxalin-2-yl)pyrazolo[1,5-a]pyrimidine-5,7-diol. MS (ESI): m/z 306 (M−H).

(f)

The preparation was performed in a similar manner as Example 1.001 (f) from 2-(3-ethylquinoxalin-2-yl)pyrazolo[1,5-a]pyrimidine-5,7-diol (1.03 g, 2.41 mmol) to give 3-(5,7-dichloropyrazolo[1,5-a]pyrimidin-2-yl)-2-ethylquinoxaline. MS (APCI): m/z 344/346 (M+H).

(g)

The preparation was performed in a similar manner as Example 1.001 (g) from 3-(5,7-Dichloropyrazolo[1,5-a]pyrimidin-2-yl)-2-ethylquinoxaline (734 mg, 2.13 mmol) to give 5-chloro-2-(3-ethylquinoxalin-2-yl)-N-(tetrahydro-2H-pyran-4-yl)pyrazolo[1,5-a]pyrimidin-7-amine. MS (APCI): m/z 409/411 (M+H).

(h)

The preparation was performed in a similar manner as Example 1.001 (h) from 5-chloro-2-(3-ethylquinoxalin-2-yl)-N-(tetrahydro-2H-pyran-4-yl)pyrazolo[1,5-a]pyrimidin-7-amine (204 mg, 0.500 mmol) to give 2-(3-ethylquinoxalin-2-yl)-5-pyrrolidin-1-yl-N-(tetrahydro-2H-pyran-4-yl)pyrazolo[1,5-a]pyrimidin-7-amine. MS (APCI): m/z 444 (M+H).

(i)

To a solution of 2-(3-ethylquinoxalin-2-yl)-5-pyrrolidin-1-yl-N-(tetrahydro-2H-pyran-4-yl)pyrazolo[1,5-a]pyrimidin-7-amine (132 mg, 2.00 mmol) in chloroform (2.0 mL) was added 4N hydrogen chloride solution in 1,4-dioxane (0.5 mL). The resulting precipitate was collected and washed with diethyl ether to give 2-(3-ethylquinoxalin-2-yl)-5-pyrrolidin-1-yl-N-(tetrahydro-2H-pyran-4-yl)pyrazolo[1,5-a]pyrimidin-7-amine dihydrochloride (the compound of Example 1.004 listed in the Table of Examples as described hereinafter). $^1$H-NMR (400 MHz, DMSO-$d_6$): δ 1.31 (3H, t, J=7.4 Hz), 1.85-1.91 (4H, m), 2.04-2.06 (4H, m), 3.45 (2H, q, J=7.4 Hz), 3.65 (4H, m), 3.94 (2H, m), 4.12 (1H, m), 5.64 (1H, s), 6.86 (1H, s), 7.84-7.92 (2H, m), 8.10-8.15 (2H, m), 8.34 (1H, br-d, J=8.8 Hz).

Example 1.005

(a)

The preparation was performed in a similar manner as Example 1.001 (b) from ethyl 3-trifluoromethylquinoxaline (10.4 g, 38.5 mmol) to give 3-(3-trifluoromethylquinoxalin-2-yl)-3-oxopropanenitrile. MS (ESI): m/z 264 (M−H).

(b)

The preparation was performed in a similar manner as Example 1.001 (c) from 3-(3-trifluoromethylquinoxalin-2-yl)-3-oxopropanenitrile (8.33 g, 31.4 mmol) to give 3-(3-trifluoromethylquinoxalin-2-yl)-1H-pyrazol-5-amine. MS (ESI): m/z 280 (M+H).

(c)

The preparation was performed in a similar manner as Example 1.001 (d) Method A from 3-(3-trifluoromethylquinoxalin-2-yl)-1H-pyrazol-5-amine (6.34 g, 22.7 mmol) to give ethyl 3-{[3-(3-trifluoromethylquinoxalin-2-yl)-1H-pyrazol-5-yl]amino}-3-oxopropanoate. MS (ESI): m/z 394 (M+H).

(d)

The preparation was performed in a similar manner as Example 1.001 (e) Method A from ethyl 3-{[3-(3-trifluoromethylquinoxalin-2-yl)-1H-pyrazol-5-yl]amino}-3-oxopropanoate (6.87 g, 17.5 mmol) to give 2-(3-trifluoromethylquinoxalin-2-yl)pyrazolo[1,5-a]pyrimidine-5,7-diol. MS (ESI): m/z 346 (M−H).

(e)

The preparation was performed in a similar manner as Example 1.001 (f) from 2-(3-trifluoromethylquinoxalin-2-yl)pyrazolo[1,5-a]pyrimidine-5,7-diol (4.94 g, 14.2 mmol) to give 3-(5,7-dichloropyrazolo[1,5-a]pyrimidin-2-yl)-2-trifluoromethylquinoxaline. MS (APCI): m/z 384/386 (M+H).

(f)

The preparation was performed in a similar manner as Example 1.001 (g) from 3-(5,7-dichloropyrazolo[1,5-a]pyrimidin-2-yl)-2-trifluoromethylquinoxaline (300 mg, 0.781 mmol) to give 5-chloro-N-(tetrahydro-2H-pyran-4-yl)-2-(3-trifluoromethylquinoxalin-2-yl)pyrazolo[1,5-a]pyrimidin-7-amine. MS (APCI): m/z 449/451 (M+H).

(g)

The preparation was performed in a similar manner as Example 1.001 (h) from 5-chloro-N-(tetrahydro-2H-pyran-4-yl)-2-(3-trifluoromethylquinoxalin-2-yl)pyrazolo[1,5-a]pyrimidin-7-amine (172 mg, 0.384 mmol) to give 5-pyrrolidin-1-yl-N-(tetrahydro-2H-pyran-4-yl)-2-[3-(trifluoromethyl)quinoxalin-2-yl]pyrazolo[1,5-c]pyrimidin-7-amine. MS (APCI): m/z 484 (M+H).

(h)

The preparation was performed in a similar manner as Example 1.001 (i) from 5-pyrrolidin-1-yl-N-(tetrahydro-2H-pyran-4-yl)-2-[3-(trifluoromethyl)quinoxalin-2-yl]pyrazolo[1,5-a]pyrimidin-7-amine (177 mg, 0.367 mmol) to give 5-pyrrolidin-1-yl-N-(tetrahydro-2H-pyran-4-yl)-2-[3-(trifluoromethyl)quinoxalin-2-yl]pyrazolo[1,5-a]pyrimidin-7-amine hydrochloride (the compound of Example 1.005 listed in the Table of Examples as described hereinafter). $^1$H-NMR (400 MHz, DMSO-$d_6$): δ 1.78-1.86 (4H, m), 2.03-2.07 (4H, m), 3.45-3.51 (2H, m), 3.63 (4H, m), 3.91 (2H, m), 4.09 (1H, m), 5.65 (1H, s), 6.69 (1H, s), 8.11-8.19 (2H, m), 8.31-8.39 (2H, m).

Example 1.006

(a)

To a suspension of sodium hydride (60% dispersion in mineral oil, 12.0 g, 300 mmol) in toluene (450 mL) was added a solution of ethyl 7-fluoro-3-methylquinoxaline 2-carboxylate (35.1 g, 150 mmol) and acetonitrile (19.6 mL, 375 mmol) in toluene (40 mL) dropwise over 35 min at 85° C. After being stirred for 5 min at the same temperature, the reaction mixture was cooled to 0° C., and then added water (175 mL). The aqueous layer was separated and the organic layer was extracted with 1N aqueous sodium hydroxide (200 mL). The combined aqueous layer was acidified to pH 2 with conc. Hydrochloric acid (45.0 mL) at 0° C., and the resulting precipitate was collected and washed with water (150 mL). The solid was dissolved with chloroform (1000 mL) and water (500 mL). The aqueous layer was extracted with chloroform (300 mL). The combined organic layer was washed with brine, dried over sodium sulfate, filtered and the filtrate was concentrated in vacuo. The residue was triturated with ethanol to give 3-(7-fluoro-3-methylquinoxalin-2-yl)-3-oxopropanenitrile. MS (APCI): m/z 230 (M+H).

(b)

To a suspension of 3-(7-fluoro-3-methylquinoxalin-2-yl)-3-oxopropanenitrile (48.6 g, 212 mmol) in ethanol (530 mL) and acetic acid (53 mL) was added hydrazine hydrate (79%, 19.6 mL, 318 mmol). The reaction mixture was reflux for 5 h, and then concentrated in vacuo. The residue was triturated with water and diisopropyl ether subsequently to give 3-(7-fluoro-3-methylquinoxalin-2-yl)-1H-pyrazol-5-amine. MS (APCI): m/z 244 (M+H).

(c)

To a suspension of 3-(7-fluoro-3-methylquinoxalin-2-yl)-1H-pyrazol-5-amine (45.7 g, 188 mmol) in pyridine (750 mL) was added ethyl hydrogen malonate (5.35 mL, 62.5 mmol) and N-ethyl-N'-(3-dimethylaminopropyl)carbodiimide hydrochloride (54.0 g, 282 mmol) at 0° C. The reaction mixture was stirred at ambient temperature for 3 h, and then concentrated in vacuo. The residue was triturated with water, ethanol and acetone subsequently to give ethyl 3-{[3-(7-fluoro-3-methylquinoxalin-2-yl)-1H-pyrazol-5-yl]amino}-3-oxopropanoate. MS (APCI): m/z 358 (M+H).

(d)

To a suspension of ethyl 3-{[3-(7-fluoro-3-methylquinoxalin-2-yl)-1H-pyrazol-5-yl]amino}-3-oxopropanoate (30.0 g, 84.0 mmol) in methanol (210 mL), tetrahydrofuran (210 mL) and water (210 mL) was added 4-dimethylaminopyridine (51.3 g, 420 mmol) at ambient temperature. After being stirred at 85° C. for 5 h, the reaction mixture was diluted with ethyl acetate (750 mL) and water (750 mL) at ambient temperature. And the insoluble material was filtered off. The filtrate was washed with water (450 mL). The combined aqueous layer was washed with ethyl acetate (500 mL×2), and acidified to pH 2 with conc. Hydrochloric acid (17.0 mL) at ambient temperature, and then stirred for overnight. The resulting precipitate was collected and washed with water to give 2-(7-fluoro-3-methylquinoxalin-2-yl)pyrazolo[1,5-a]pyrimidine-5,7-diol. MS (APCI): m/z 312 (M+H).

(e)

A suspension of 2-(7-fluoro-3-methylquinoxalin-2-yl)pyrazolo[1,5-a]pyrimidine-5,7-diol (8.30 g, 26.7 mmol) in phosphorous oxychloride (81.1 g, 534 mmol) was heated at 100° C. for 3 h. After being cooled to ambient temperature, the reaction mixture was concentrated in vacuo. The residue was poured into 10% aqueous potassium carbonate (700 mL) at 0° C. The resulting precipitate was collected and washed with water to give 3-(5,7-dichloropyrazolo[1,5-a]pyrimidin-2-yl)-6-fluoro-2-methylquinoxaline. MS (APCI): m/z 348/350 (M+H).

(f)

A suspension of 3-(5,7-dichloropyrazolo[1,5-a]pyrimidin-2-yl)-6-fluoro-2-methylquinoxaline (157 mg, 0.451 mmol) in N,N-dimethylformamide (4.0 mL), 1-amino-2-methyl-propan-2-ol (48 mg, 0.541 mmol), and potassium carbonate (187 mg, 1.35 mmol) was stirred at room temperature for 2 h. The reaction mixture was poured into ice-cooled water, and the resulting precipitate was collected and washed with water to give 1-{[5-chloro-2-(7-fluoro-3-methylquinoxalin-2-yl)pyrazolo[1,5-a]pyrimidin-7-yl]amino}-2-methylpropan-2-ol. MS (APCI): m/z 401/403 (M+H).

(g)

A suspension of 1-{[5-chloro-2-(7-fluoro-3-methylquinoxalin-2-yl)pyrazolo[1,5-c]pyrimidin-7-yl]amino}-2-methylpropan-2-ol (170 mg, 0.424 mmol), (R)-3-fluoropyrrolidine hydrochloride (268 mg, 2.12 mmol), and 1,8-diazabicyclo[5.4.0]undec-7-ene (387 mg, 2.54 mmol) in N-methylpyrrolidinone (5.0 mL) was heated at 70° C. overnight. After being cooled to ambient temperature, the reaction mixture was diluted with ice-cooled water. The resulting precipitate was collected and washed with water to give 1-({2-(7-fluoro-3-methylquinoxalin-2-yl)-5-[(3R)-3-fluoropyrrolidin-1-yl]pyrazolo[1,5-a]pyrimidin-7-yl}amino)-2-methylpropan-2-ol. MS (APCI): m/z 454 (M+H).

(h)

To a suspension of 1-({2-(7-fluoro-3-methylquinoxalin-2-yl)-5-[(3R)-3-fluoropyrrolidin-1-yl]pyrazolo[1,5-a]pyrimidin-7-yl}amino)-2-methylpropan-2-ol (213 mg, 0.470 mmol) in ethanol (3.0 mL) was added 2N aqueous hydrochloric acid (0.282 mL), and the mixture was heated at 80° C., and then ethanol (2.0 mL) and water (0.2 mL) was added. The mixture was slowly cooled to ambient temperature and then ethanol (2.0 mL) was added. The resulting precipitate was collected, and washed with diethyl ether to give 1-({2-(7-fluoro-3-methylquinoxalin-2-yl)-5-[(3R)-3-fluoropyrrolidin-1-yl]pyrazolo[1,5-a]pyrimidin-7-yl}amino)-2-methylpropan-2-ol hydrochloride (the compound of Example 1.006 listed in the Table of Examples as described hereinafter). $^1$H-NMR (400 MHz, DMSO-$d_6$): δ 1.24 (6H, s), 2.25-2.43 (2H, m), 3.10 (3H, s), 3.62-3.70 (2H, m), 3.80-4.01 (4H, m), 5.52-5.63 (1H, m), 5.71 (1H, s), 6.94 (1H, s), 7.81 (1H, ddd, J=9.1, 8.8, 2.7 Hz), 7.95 (1H, dd, J=9.6, 2.9 Hz), 7.99 (1H, br), 8.14 (1H, dd, J=9.1, 5.9 Hz).

Example 1.007

A suspension of 5-chloro-2-(3-methylquinoxalin-2-yl)-N-(tetrahydro-2H-pyran-4-yl)pyrazolo[1,5-a]pyrimidin-7-amine (Example 1.001 (g)) (398 mg, 1.01 mmol) and (s)-3-hydroxypyrrolidine (351 mg, 4.03 mmol) in N-methyl-2-pyrrolidinone (5.0 mL) was heated at 80° C. for 6 h. Then the reaction mixture was poured into cold water. The resulting precipitate was collected and purified by silica gel column chromatography (ethyl acetate to ethyl acetate:methanol=7:3) to give 1-[2-(3-methylquinoxalin-2-yl)-7-(tetrahydro-2H-pyran-4-ylamino)pyrazolo[1,5-a]pyrimidin-5-yl]pyrrolidin-3-ol (the compound of Example 1.007 listed in the Table of Examples as described hereinafter). $^1$H-NMR (500 MHz, CDCl$_3$): δ 1.74-1.81 (2H, m), 2.12-2.22 (4H, m), 3.03 (3H, s), 3.58 (2H, dt, J=2.3, 11.9 Hz), 3.65-3.76 (5H, m), 4.08 (2H, dt, J=11.6, 3.2 Hz), 4.64-4.67 (1H, m), 5.16 (1H, s), 6.16 (1H, d, J=8.0 Hz), 6.66 (1H, s), 7.70-7.76 (2H, m), 8.03-8.05 (1H, m), 8.17-8.19 (1H, m).

Example 1.008

To a solution of 1-[2-(3-methylquinoxalin-2-yl)-7-(tetrahydro-2H-pyran-4-ylamino)pyrazolo[1,5-a]pyrimidin-5-yl]pyrrolidin-3-ol (200 mg, 0.449 mmol) and methanesulfonyl chloride (77 mg, 0.673 mmol) in dichloromethane (5.0 mL) was added triethylamine (0.125 mL, 0.898 mmol) at 0° C. After being stirred for 2 h, the reaction mixture was poured into water. The mixture was extracted with chloroform, and the organic layer was washed with saturated brine, dried over sodium sulfate, filtrated and concentrated in vacuo. The crude was purified by silica gel column chromatography (chloroform to chloroform:methanol=97:3) to give (3S)-1-[2-(3-methylquinoxalin-2-yl)-7-(tetrahydro-2H-pyran-4-ylamino)pyrazolo[1,5-a]pyrimidin-5-yl]pyrrolidin-3-yl methanesulfonate (the compound of Example 1.008 listed in the Table of Examples as described hereinafter). $^1$H-NMR (400 MHz, CDCl$_3$): δ 1.73-1.83 (2H, m), 2.12-2.15 (2H, m), 2.30-2.39 (1H, m), 2.47-2.52 (1H, m), 3.04 (3H, s), 3.08 (3H, s), 3.56-3.63 (2H, m), 3.68-3.89 (4H, m), 3.99-4.02 (1H, m), 4.07-4.10 (2H, m), 5.19 (1H, s), 5.44-5.46 (1H, m), 6.20 (1H, d, J=8.2 Hz), 6.67 (1H, s), 7.70-7.77 (2H, m), 8.03-8.06 (1H, m), 8.16-8.19 (1H, m).

Example 1.009

A solution of (35)-1-[2-(3-methylquinoxalin-2-yl)-7-(tetrahydro-2H-pyran-4-ylamino)pyrazolo[1,5-a]pyrimidin-5-yl]pyrrolidin-3-yl methanesulfonate (50 mg, 0.0955 mmol) 4,7,13,16,21,24-hexaoxa-1,10-diazabicyclo[8.8.8]hexacosane (108 mg, 0.286 mmol), and potassium fluoride (17 mg, 0.286 mmol) in acetonitrile (2.0 mL) was refluxed for 15 min. After being cooled to ambient temperature, the reaction mixture was concentrated in vacuo. The crude was purified by silica gel column chromatography (chloroform to chloroform:methanol=97:3) to give 5-(2,5-dihydro-1H-pyrrol-1-yl)-2-(3-methylquinoxalin-2-yl)-N-(tetrahydro-2H-pyran-4-yl)pyrazolo[1,5-a]pyrimidin-7-amine (the compound of Example 1.009 listed in the Table of Examples as described hereinafter). $^1$H-NMR (400 MHz, CDCl$_3$): δ 1.73-1.82 (2H, m), 2.13-2.16 (2H, m), 3.04 (3H, s), 3.59 (2H, dt, J=11.8, 2.1 Hz), 3.68-3.78 (1H, m), 4.09 (2H, dt, J=11.8, 3.6 Hz), 3.48 (4H, br), 5.17 (1H, s), 5.98 (2H, s), 6.17 (1H, d, J=7.9 Hz), 6.67 (1H, s), 7.69-7.77 (2H, m), 8.03-8.06 (1H, m), 8.17-8.19 (1H, m).

Example 1.010

(a)

To a suspension of sodium hydride (60% dispersion in mineral oil, 12 mg, 0.303 mmol) in 1,4-dioxane (3.0 mL) was added 4-hydroxytertahydropyran (31 mg, 0.303 mmol) at 0° C. After being stirred at room temperature for 10 min, 5-chloro-2-(3-methylquinoxalin-2-yl)-N-(tetrahydro-2H-pyran-4-yl)pyrazolo[1,5-a]pyrimidin-7-amine (Example 1.001 (g)) (100 mg, 0.303 mmol) was added. The reaction mixture was stirred at same temperature overnight, and then poured into water, and the mixture was extracted with chloroform. The organic layer was washed with saturated brine, dried over sodium sulfate, filtrated and concentrated in vacuo. The crude was purified by silica gel column chromatography (hexane:ethyl acetate=9:1 to 1:1) to give 2-[5-chloro-7-(tetrahydro-2H-pyran-4-yloxy)pyrazolo[1,5-a]pyrimidin-2-yl]-3-methylquinoxaline. MS (APCI): m/z 396/398 (M+H).

(b)

A mixture of 2-[5-chloro-7-(tetrahydro-2H-pyran-4-yloxy)pyrazolo[1,5-a]pyrimidin-2-yl]-3-methylquinoxaline (90 mg, 0.227 mmol), pyrrolidine (49 mg, 0.682 mmol), sodium tert-butoxide (33 mg, 0.341 mmol), palladium(II) acetate (52 mg, 0.227 mmol), and 2-dicyclohexylphosphino-2'-(N,N-dimethylamino)biphenyl (179 mg, 0.454 mmol) in 1,4-dioxane (4.0 mL) was heated at 100° C. for 40 min. After being cooled to ambient temperature, the reaction mixture was poured into water, and the mixture was extracted with chloroform. The organic layer was washed with saturated brine, dried over sodium sulfate, filtrated and concentrated in vacuo. The residue was purified by silica gel column chromatography (hexane:ethyl acetate=1:1 to 1:9) to give 2-methyl-3-[5-pyrrolidin-1-yl-7-(tetrahydro-2H-pyran-4-yloxy)pyrazolo[1,5-a]pyrimidin-2-yl]quinoxaline. MS (APCI): m/z 431 (M+H).

(c)

The preparation was performed in a similar manner as Example 1.001 (i) to give 2-methyl-3-[5-pyrrolidin-1-yl-7-(tetrahydro-2H-pyran-4-yloxy)pyrazolo[1,5-c]pyrimidin-2-yl]quinoxaline hydrochloride (the compound of Example 1.010 listed in the Table of Examples as described hereinafter). $^1$H-NMR (400 MHz, DMSO-d$_6$): δ 1.82-1.90 (2H, m), 2.04-2.07 (4H, m), 2.14-2.18 (2H, m), 3.09 (3H, s), 3.62-3.68 (6H, m), 3.90-3.95 (2H, m), 5.35-5.41 (1H, m), 6.12 (1H, s), 6.99 (1H, s), 7.82-7.89 (2H, m), 8.03-8.08 (1H, m), 8.13-8.15 (1H, m).

The preparation of the dihydrochloride salt was also performed in the similar manner by using excess amount of aqueous hydrochloric acid solution.

Example 1.011

A suspension of 5-chloro-2-(3-methylquinoxalin-2-yl)-N-(tetrahydro-2H-pyran-4-yl)pyrazolo[1,5-a]pyrimidin-7-amine (Example 1.001 (g)) (97 mg, 0.246 mmol), cyclopenten-1-ylboronic acid (55 mg, 0.491 mmol), tetrakis(triphenylphosphine)palladium(0) (57 mg, 0.0493 mmol), and cesium fluoride (112 mg, 0.737 mmol) in 1,2-dimethoxyethane (2.0 mL) was heated at 80° C. for 3 h. After being cooled to ambient temperature, the reaction mixture was poured into water, and the mixture was extracted with ethyl acetate. The organic layer was washed with water and saturated brine, dried over sodium sulfate, filtrated and concentrated in vacuo. The crude was purified by silica gel column chromatography (hexane:ethyl acetate=9:1 to 2:3) to give 5-cyclopent-1-en-1-yl-2-(3-methylquinoxalin-2-yl)-N-(tetrahydro-2H-pyran-4-yl)pyrazolo[1,5-a]pyrimidin-7-amine (the compound of Example 1.011 listed in the Table of Examples as described hereinafter). $^1$H-NMR (400 MHz, CDCl$_3$): δ 1.73-1.86 (2H, m), 2.03-2.21 (4H, m), 2.60-2.66 (2H, m), 2.86-2.93 (2H, m), 3.05 (3H, s), 3.61 (2H, ddd, J=11.8, 11.8, 2.4 Hz), 3.77-3.87 (1H, m), 4.10 (2H, ddd, J=11.8, 3.3, 3.3 Hz), 6.19 (1H, s), 6.33 (1H, d, J=8.2 Hz), 6.68 (1H, s), 7.08 (1H, s), 7.72-7.79 (2H, m), 8.04-8.08 (1H, m), 8.17-8.21 (1H, m).

Example 1.012

A suspension of 5-cyclopent-1-en-1-yl-2-(3-methylquinoxalin-2-yl)-N-(tetrahydro-2H-pyran-4-yl)pyrazolo[1,5-a]

pyrimidin-7-amine (30 mg, 0.0703 mmol) and palladium on carbon (5%, 30 mg) in dichloromethane (2.0 mL) and methanol (2.0 mL) was stirred for 3 h under hydrogen atmosphere. Then reaction mixture was filtrated with chloroform, and the filtrate was concentrated in vacuo. The crude was purified by silica gel column chromatography (hexane:ethyl acetate=19:1 to 1:1) to give 5-cyclopentyl-2-(3-methylquinoxalin-2-yl)-N-(tetrahydro-2H-pyran-4-yl)pyrazolo[1,5-a]pyrimidin-7-amine (the compound of Example 1.012 listed in the Table of Examples as described hereinafter). $^1$H-NMR (400 MHz, CDCl$_3$): δ 1.67-1.95 (8H, m), 2.08-2.20 (4H, m), 3.05 (3H, s), 3.11-3.23 (1H, m), 3.60 (2H, ddd, J=11.8, 11.8, 2.4 Hz), 3.74-3.85 (1H, m), 4.10 (2H, ddd, J=11.5, 3.3, 3.3 Hz), 5.94 (1H, s), 6.32 (1H, d, J=7.9 Hz), 7.02 (1H, s), 7.71-7.79 (2H, m), 8.04-8.08 (1H, m), 8.16-8.20 (1H, m).

Example 1.013

(a)

The preparation was performed in a similar manner as Example 1.006 (f) from 3-(5,7-dichloropyrazolo[1,5-a]pyrimidin-2-yl)-6-fluoro-2-methylquinoxaline (1.90 g, 5.46 mmol) and trans-4-amino-1-methylcyclohexanol (846 mg, 6.55 mmol) to give trans-4-{[5-chloro-2-(7-fluoro-3-methylquinoxalin-2-yl)pyrazolo[1,5-a]pyrimidin-7-yl]amino}-1-methylcyclohexanol. MS (APCI): m/z 441/443 (M+H).

(b)

The preparation was performed in a similar manner as Example 1.006 (g) from trans-4-{[5-chloro-2-(7-fluoro-3-methylquinoxalin-2-yl)pyrazolo[1,5-a]pyrimidin-7-yl]amino}-methylcyclohexanol (1.32 g, 3.00 mmol) to give trans-4-({2-(7-Fluoro-3-methylquinoxalin-2-yl)-5-[(3R)-3-fluoropyrrolidin-1-yl]pyrazolo[1,5-a]pyrimidin-7-yl}amino)-1-methylcyclohexanol). MS (APCI): m/z 494 (M+H).

(c)

The preparation was performed in a similar manner as Example 1.006 (h) from trans-4-({2-(7-fluoro-3-methylquinoxalin-2-yl)-5-[(3R)-3-fluoropyrrolidin-1-yl]pyrazolo[1,5-a]pyrimidin-7-yl}amino)-1-methylcyclohexanol (1.18 g, 2.39 mmol) to give trans-4-({2-(7-Fluoro-3-methylquinoxalin-2-yl)-5-[(3R)-3-fluoropyrrolidin-1-yl]pyrazolo[1,5-a]pyrimidin-7-yl}amino)-1-methylcyclohexanol hydrochloride (the compound of Example 1.013 listed in the Table of Examples as described hereinafter). $^1$H-NMR (500 MHz, DMSO-d$_6$): δ 1.22 (3H, s), 1.55-1.65 (4H, m), 1.70-1.81 (2H, m), 1.83-1.92 (2H, m), 2.19-2.44 (2H, m), 3.06 (3H, s), 3.63-4.01 (5H, m), 5.55 (1H, m), 5.61 (1H, s), 6.82 (1H, s), 7.79-7.83 (1H, m), 7.91-7.94 (2H, m), 8.14-8.17 (1H, m).

Examples 1.014 to 1.171

The compounds of Examples 1.014 to 1.171 listed in the Table of Examples as described hereinafter were obtained in the similar manner as described in the above Example 1.001.

Example 1.172

(a)

(S)-2-(tert-butoxycarbonylamino-5-benzyloxypentanoic acid dicyclohexylamine salt (10.0 g, 19.8 mmol) was purified by silica gel column chromatography (ethyl acetate to ethyl acetate:methanol=19:1) in order to remove dicyclohexylamine. The resulting oil, ethyl 2-amino-3-oxobutanoate (3.60 g, 19.8 mmol), ethyl-3-(3-dimethylaminopropyl)carbodiimide hydrochloride (5.69 g, 29.7 mmol), 1-hydroxybenzotriazole (4.01 g, 29.7 mmol), triethylamine (6.87 mL, 49.5 mmol), in chloroform (40 mL) was stirred for 6 h at room temperature, and then reaction mixture was poured into water. The organic layer was separated, washed with saturated brine, dried over sodium sulfate, filtrated and concentrated in vacuo. The crude was purified by silica gel column chromatography (hexane:ethyl acetate=9:1 to 3:2) to give ethyl 2-{[5-(benzyloxy)-N-(tert-butoxycarbonyl)-L-norvalyl]amino}-3-oxobutanoate. MS (APCI): m/z 468 (M+NH$_4$).

(b)

To a solution of ethyl 2-{[5-(benzyloxy)-N-(tert-butoxycarbonyl)-L-norvalyl]amino}-3-oxobutanoate (5.31 g, 11.8 mmol) in ethanol (20 mL) was added 4N hydrochloric acid in 1,4-dioxane (20 mL) at room temperature. After being stirred for 16 h at same temperature, the reaction mixture was concentrated in vacuo. A solution of the residue in pyridine (40 mL) was heated at 60° C. for 23 h. After being cooled to ambient temperature, the mixture was concentrated in vacuo. The residue was poured into water, and the mixture was extracted with chloroform. The organic layer was washed with water and saturated brine, dried over sodium sulfate, filtrated and concentrated in vacuo. To a solution of the residue in dichloromethane (20 mL) was added manganes dioxide (1.03 g) at room temperature. After being stirred for 1.5 h at same temperature, the reaction mixture was filtrated through celite with chloroform. The filtrate was combined and concentrated in vacuo. The crude was purified by silica gel column chromatography (chloroform to chloroform:methanol=19:1) to give ethyl 5-[3-(benzyloxy)propyl]-6-hydroxy-3-methylpyrazine-2-carboxylate. MS (APCI): m/z 331 (M+H).

(c)

A suspension of ethyl 5-[3-(benzyloxy)propyl]-6-hydroxy-3-methylpyrazine-2-carboxylate (2.91 g, 8.80 mmol) and palladium hydroxide (1.06 g) in ethanol (60 mL) was refluxed for 7 h. After being cooled to ambient temperature, the reaction mixture was filtrated through celite with ethanol. The filtrate was combined and concentrated in vacuo. The crude was purified by silica gel column chromatography (chloroform to chloroform:methanol=19:1) to give ethyl 6-hydroxy-5-(3-hydroxypropyl)-3-methylpyrazine-2-carboxylate. MS (APCI): m/z 241 (M+H).

(d)

To a solution of ethyl 6-hydroxy-5-(3-hydroxypropyl)-3-methylpyrazine-2-carboxylate (1.03 g, 4.29 mmol) and triphenylphosphine (1.69 g, 6.43 mmol) in tetrahydrofuran (86 mL) was added diethyl azodicarboxylate solution (40% wt. % in toluene, 2.92 mL, 6.43 mmol) at room temperature. After being stirred for 50 min, the reaction mixture was concentrated in vacuo. The crude was purified by silica gel column chromatography (hexane:ethyl acetate=9:1 to 7:3), triturated with diisopropyl ether, and silica gel column chromatography (chloroform to chloroform:methanol=19:1) to give ethyl 2-methyl-7,8-dihydro-6H-pyrano[2,3-b]pyrazine-3-carboxylate. MS (APCI): m/z 223 (M+H).

(e)

The preparation was performed in a similar manner as Example 1.006 (a) method B from ethyl 2-methyl-7,8-dihydro-6H-pyrano[2,3-b]pyrazine-3-carboxylate (725 mg, 3.26 mmol) to 3-(2-methyl-7,8-dihydro-6H-pyrano[2,3-b]pyrazin-3-yl)-3-oxopropanenitrile. MS (APCI): m/z 218 (M+H).

(f)

The preparation was performed in a similar manner as Example 1.001(c) from 3-(2-methyl-7,8-dihydro-6H-pyrano[2,3-b]pyrazin-3-yl)-3-oxopropanenitrile (505 mg, 2.32 mmol) to give 3-(2-methyl-7,8-dihydro-6H-pyrano[2,3-b]pyrazin-3-yl)-1H-pyrazol-5-amine. MS (APCI): m/z 232 (M+H).

(g)

The preparation was performed in a similar manner as Example 1.006 (c) Method B from 3-(2-methyl-7,8-dihydro-6H-pyrano[2,3-b]pyrazin-3-yl)-1H-pyrazol-5-amine (550 mg, 2.38 mmol) to give ethyl 3-{[3-(2-methyl-7,8-dihydro-6H-pyrano[2,3-b]pyrazin-3-yl)-1H-pyrazol-5-yl]amino}-3-oxopropanoate. MS (APCI): m/z 346 (M+H).

(h)

A suspension of ethyl 3-{[3-(2-methyl-7,8-dihydro-6H-pyrano[2,3-b]pyrazin-3-yl)-1H-pyrazol-5-yl]amino}-3-oxopropanoate (535 mg, 1.55 mmol) and N,N-dimethylaminopyridine (946 mg, 7.75 mmol) in methanol (15 mL), tetrahydrofuran (15 mL), and water (15 mL) was refluxed for 25 h. After being cooled to ambient temperature, the reaction mixture was concentrated in vacuo. The residue was acidified to pH 2 with 6N aqueous hydrochloric acid at 0° C., and then concentrated in vacuo. The residue was triturated with ethyl acetate.

The crude and phosphorous oxychloride (11.9 g, 77.5 mmol) was treated in similar manner as Example 1.001(f) to give 3-(5,7-dichloropyrazolo[1,5-a]pyrimidin-2-yl)-2-methyl-7,8-dihydro-6H-pyrano[2,3-b]pyrazine. MS (APCI): m/z 336/338 (M+H).

(i)

The preparation was performed in a similar manner as Example 1.001(g) from 3-(5,7-dichloropyrazolo[1,5-a]pyrimidin-2-yl)-2-methyl-7,8-dihydro-6H-pyrano[2,3-b]pyrazine (150 mg, 0.466 mmol) to give trans-4-{[5-chloro-2-(2-methyl-7,8-dihydro-6H-pyrano[2,3-b]pyrazin-3-yl)pyrazolo[1,5-a]pyrimidin-7-yl]amino}-1-methylcyclohexanol. MS (APCI): m/z 429/431 (M+H).

(j)

The preparation was performed in a similar manner as Example 1.001 (f) from trans-4-{[5-chloro-2-(2-methyl-7,8-dihydro-6H-pyrano[2,3-b]pyrazin-3-yl)pyrazolo[1,5-a]pyrimidin-7-yl]amino}-1-methylcyclohexanol (183 mg, 0.427 mmol) to give trans-1-Methyl-4-{[2-(2-methyl-7,8-dihydro-6H-pyrano[2,3-b]pyrazin-3-yl)-5-pyrrolidin-1-ylpyrazolo[1,5-a]pyrimidin-7-yl]amino}cyclohexanol. MS (APCI): m/z 464 (M+H).

(k)

The preparation was performed in a similar manner as Example 1.004 (i) from trans-1-Methyl-4-{[2-(2-methyl-7,8-dihydro-6H-pyrano[2,3-b]pyrazin-3-yl)-5-pyrrolidin-1-ylpyrazolo[1,5-a]pyrimidin-7-yl]amino}cyclohexanol (140 mg, 0.302 mmol) to give trans-1-Methyl-4-{[2-(2-methyl-7,8-dihydro-6H-pyrano[2,3-b]pyrazin-3-yl)-5-pyrrolidin-1-ylpyrazolo[1,5-a]pyrimidin-7-yl]amino}cyclohexanol hydrochloride (the compound of Example 1.172 listed in the Table of Examples as described hereinafter). MS (APCI): m/z 464 (M+H), $^1$H NMR (500 MHz, DMSO-$d_6$) δ: 12.75 (1H, br), 7.92 (1H, br-d), 6.67 (1H, s), 5.55 (1H, s), 4.36 (2H, t, J=4.8 Hz), 3.88 (1H, br), 3.62 (4H, br), 2.96 (2H, t, J=6.4 Hz), 2.80 (3H, s), 2.04-2.11 (6H, m), 1.82-1.86 (2H, m), 1.72-1.80 (2H, m), 1.58-1.60 (4H, m), 1.22 (3H, s).

Example 1.173

(a)

To a solution of 2-methoxy-6,7-dihydro-8H-pyrano[2,3-b]pyrazine (*J. Chem. Soc. Perkin Trans. I* 1988, 2585-2593; 3.16 g, 19.0 mmol) in N,N-dimethylformamide (95 mL) was added N-bromosuccinimide (5.08 g, 28.5 mmol) at room temperature, and then heated at 60° C. for 5 h. After being cooled to ambient temperature, the reaction mixture was diluted ethyl acetate, washed with 2% aqueous sodium sulfite, water, and saturated brine. The organic layer was dried over sodium sulfate, filtrated and concentrated in vacuo. The crude was purified by silica gel column chromatography (hexane:ethyl acetate=9:1 to 7:3) to give 3-bromo-2-methoxy-7,8-dihydro-6H-pyrano[2,3-b]pyrazine. MS (APCI): m/z 247 (M+H).

(b)

The preparation was performed in a similar manner as Example 1.001 (a) Method B from 3-bromo-2-methoxy-7,8-dihydro-6H-pyrano[2,3-b]pyrazine (2.50 mg, 10.2 mmol) to give 2-methoxy-3-methyl-7,8-dihydro-6H-pyrano[2,3-b]pyrazine. MS (APCI): m/z 181 (M+H).

(c)

To a suspension of 2-methoxy-3-methyl-7,8-dihydro-6H-pyrano[2,3-b]pyrazine (1.95 g, 10.8 mmol) in sulfolane (25 mL) was added iodotrimethylsilane (15.0 g, 75.0 mmol) at 30° C. The reaction mixture was heated at 40-45° C. for 8 h, and then cooled to ambient temperature and stirred for 2 days. And the reaction mixture was diluted with ethyl acetate and washed with 2% aqueous sodium sulfite. The aqueous layer was extracted with ethyl acetate and chloroform. The organic layer was combined, dried over sodium sulfate, filtrated and concentrated in vacuo. The crude was purified by silica gel column chromatography (ethyl acetate to ethyl acetate:methanol=93:7) to give 3-methyl-7,8-dihydro-6H-pyrano[2,3-b]pyrazin-2-ol and recovered starting material. MS (APCI): m/z 177 (M+H).

(d)

To a suspension of 3-methyl-7,8-dihydro-6H-pyrano[2,3-b]pyrazin-2-ol (735 mg, 6.33 mmol) and N,N-diisopropylethylamine (2.45 g, 19.0 mmol) in dichloromethane (37 mL) was added trifluoromethanesulfonic anhydride (2.14 g, 7.59 mmol) dropwise over 5 min at 0° C. After being stirred for 30 min at same temperature, the reaction mixture was poured into saturated aqueous sodium bicarbonate. The mixture was extracted with chloroform, and the organic layer was washed with saturated brine, dried over sodium sulfate, filtrated and concentrated in vacuo. The crude was purified by silica gel column chromatography (hexane:ethyl acetate=9:1 to 7:3) to give 3-methyl-7,8-dihydro-6H-pyrano[2,3-b]pyrazin-2-yl trifluoromethanesulfonate. MS (APCI): m/z 299 (M+H).

(e)

A solution of 3-methyl-7,8-dihydro-6H-pyrano[2,3-b]pyrazin-2-yl trifluoromethanesulfonate (298 mg, 1.00 mmol), palladium(II) acetate (11 mg, 0.0490 mmol), bis(diphenylphosphino)ferrocene (55 mg, 0.0992 mmol), and triethylamine (202 mg, 2.00 mmol) in N,N-dimethylacetamide (3.0 mL) was heated at 80° C. for 24 h under carbon monoxide. After being cooled to ambient temperature, the reaction mixture was diluted ethyl acetate. The organic layer was washed with water, dried over sodium sulfate, filtrated and concentrated in vacuo. The crude was purified by silica gel column chromatography (hexane:ethyl acetate=3:1 to ethyl acetate) to give ethyl 3-methyl-7,8-dihydro-6H-pyrano[2,3-b]pyrazine-2-carboxylate. MS (APCI): m/z 223 (M+H).

(f)

The preparation was performed in a similar manner as Example 1.006 (a) method B from ethyl 3-methyl-7,8-dihydro-6H-pyrano[2,3-b]pyrazine-2-carboxylate (337 mg, 1.52 mmol) to give 3-(3-methyl-7,8-dihydro-6H-pyrano[2,3-b]pyrazin-2-yl)-3-oxopropanenitrile. MS (APCI): m/z 218 (M+H).

(g)

The preparation was performed in a similar manner as Example 1.001 (c) from 3-(3-methyl-7,8-dihydro-6H-pyrano[2,3-b]pyrazin-2-yl)-3-oxopropanenitrile (236 mg, 1.09 mmol) to give 3-(3-methyl-7,8-dihydro-6H-pyrano[2,3-b]pyrazin-2-yl)-1H-pyrazol-5-amine. MS (APCI): m/z 232 (M+H).

(h)

The preparation was performed in a similar manner as Example 1.006 (c) Method A from 3-(3-methyl-7,8-dihydro-6H-pyrano[2,3-b]pyrazin-2-yl)-1H-pyrazol-5-amine (253 mg, 1.09 mmol) to give ethyl 3-{[3-(3-methyl-7,8-dihydro-6H-pyrano[2,3-b]pyrazin-2-yl)-1H-pyrazol-5-yl]amino}-3-oxopropanoate. MS (APCI): m/z 346 (M+H).

(i)

A suspension of ethyl 3-{[3-(3-methyl-7,8-dihydro-6H-pyrano[2,3-b]pyrazin-2-yl)-1H-pyrazol-5-yl]amino}-3-oxopropanoate (293 mg, 0.848 mmol) and N,N-dimethylaminopyridine (518 mg, 4.24 mmol) in methanol (3 mL), tetrahydrofuran (3 mL), and water (3 mL) was heated for 8 h. After being cooled to ambient temperature, the reaction mixture was concentrated in vacuo. The residue was triturated with ethyl acetate to give 2-(3-methyl-7,8-dihydro-6H-pyrano[2,3-b]pyrazin-2-yl)pyrazolo[1,5-a]pyrimidine-5,7-diol. MS (APCI): m/z 300 (M+H).

(j)

The preparation was performed in a similar manner as Example 1.001 (f) from 2-(3-methyl-7,8-dihydro-6H-pyrano[2,3-b]pyrazin-2-yl)pyrazolo[1,5-a]pyrimidine-5,7-diol (376 mg, 0.843 mmol) to give 2-(5,7-dichloropyrazolo[1,5-a]pyrimidin-2-yl)-3-methyl-7,8-dihydro-6H-pyrano[2,3-b]pyrazine. MS (APCI): m/z 336/338 (M+H).

(k)

The preparation was performed in a similar manner as Example 1.001 (g) from 2-(5,7-dichloropyrazolo[1,5-a]pyrimidin-2-yl)-3-methyl-7,8-dihydro-6H-pyrano[2,3-b]pyrazine (98 mg, 0.241 mmol) to give trans-4-{[5-chloro-2-(3-methyl-7,8-dihydro-6H-pyrano[2,3-b]pyrazin-2-yl)pyrazolo[1,5-a]pyrimidin-7-yl]amino}-1-methylcyclohexanol. MS (APCI): m/z 429/431 (M+H).

(l)

The preparation was performed in a similar manner as Example 1.001 (f) from trans-4-{[5-chloro-2-(3-methyl-7,8-dihydro-6H-pyrano[2,3-b]pyrazin-2-yl)pyrazolo[1,5-a]pyrimidin-7-yl]amino}-1-methylcyclohexanol (46 mg, 0.107 mmol) to give trans-1-methyl-4-{[2-(3-methyl-7,8-dihydro-6H-pyrano[2,3-b]pyrazin-2-yl)-5-pyrrolidin-1-ylpyrazolo[1,5-a]pyrimidin-7-yl]amino}cyclohexanol. MS (APCI): m/z 464 (M+H).

(m)

The preparation was performed in a similar manner as Example 1.004 (i) from trans-1-methyl-4-{[2-(3-methyl-7,8-dihydro-6H-pyrano[2,3-b]pyrazin-2-yl)-5-pyrrolidin-1-ylpyrazolo[1,5-a]pyrimidin-7-yl]amino}cyclohexanol (44 mg, 0.0949 mmol) to give trans-1-Methyl-4-[2-(3-methyl-7,8-dihydro-6H-pyrano[2,3-b]pyrazin-2-yl)-5-pyrrolidin-1-ylpyrazolo[1,5-a]pyrimidin-7-yl]amino cyclohexanol hydrochloride (the compound of Example 1.173 listed in the Table of Examples as described hereinafter). MS (APCI): m/z 464 (M+H), $^1$H NMR (500 MHz, DMSO-$d_6$) δ: 7.95 (1H, d, J=8.7 Hz), 6.65 (1H, s), 5.52 (1H, s), 4.39 (2H, t, J=5.1 Hz), 3.80-3.94 (1H, m), 3.57-3.67 (4H, m), 2.96 (2H, dd, J=6.4, 6.1 Hz), 2.74 (3H, s), 2.09 (2H, ddt, J=6.4, 6.1, 5.1 Hz), 2.00-2.07 (4H, m), 1.70-1.87 (4H, m), 1.55-1.63 (4H, m), 1.21 (3H, s).

Examples 1.174 to 1.200

The compounds of Examples 1.174 to 1.200 listed in the Table of Examples as described hereinafter were obtained in the similar manner as described in the above Example 1.001.

Example 2.001

(a)

The preparation was performed in a similar manner as described in *Chem. Pharm. Bull.* 1980, 28, 2494 from ethyl hydrogen malonate (2.65 g, 19.3 mmol) and (tetrahydro-2H-pyran-4-yl)acetyl chloride (1.50 g, 8.76 mmol) to give the ethyl 3-oxo-4-(tetrahydro-2H-pyran-4-yl)butanoate. MS (APCI): m/z 215 (M+H).

(b)

A suspension of ethyl 3-oxo-4-(tetrahydro-2H-pyran-4-yl)butanoate (960 mg, 4.48 mmol) and 1N aqueous sodium hydroxide (9.00 mL, 9.00 mmol) was stirred at room temperature for 48 h. The reaction mixture was washed with diethyl ether and then acidified to pH 3 with 0.5N sulfuric acid. The mixture was extracted with ethyl acetate, and the organic layer was dried over sodium sulfate, filtrated and concentrated in vacuo to give 3-oxo-4-(tetrahydro-2H-pyran-4-yl)butanoic acid. MS (ESI): m/z 185 (M–H).

(c)

To a solution of 3-oxo-4-(tetrahydro-2H-pyran-4-yl)butanoic acid (186 mg, 1.00 mmol) in toluene (2.5 mL) and tetrahydrofuan (2.5 mL) was added oxalyl chloride (190 mg, 1.50 mmol) at room temperature. After being stirred for 1 h, the reaction mixture was concentrated in vacuo to give the crude acid chloride thereof (3-oxo-4-(tetrahydro-2H-pyran-4-yl)butanoyl chloride).

To a solution of 3-(3-methylquinoxalin-2-yl)-1H-pyrazol-5-amine (Example 1.001 (c)) (68 mg, 0.300 mmol) and diisopropylethylamine (194 mg, 1.50 mmol) in dichloromethane (2.0 mL) was added a solution of the crude acid chloride in dichloromethane (1.0 mL) at 0° C. After being stirred at room temperature for 3 h, the reaction mixture was concentrated in vacuo. The residue was diluted with ethanol (6.0 mL) and heated at 60° C. for 3 h. After being cooled to ambient temperature, the mixture was concentrated in vacuo. The residue was purified by silica gel column chromatography (chloroform to chloroform:methanol=9:1) to give N-[3-(3-methylquinoxalin-2-yl)-1H-pyrazol-5-yl]-3-oxo-4-(tetrahydro-2H-pyran-4-yl)butanamide. MS (APCI): m/z 394 (M+H).

(d)

The preparation was performed in a similar manner as Example 1.001 (e) Method A from N-[3-(3-methylquinoxalin-2-yl)-1H-pyrazol-5-yl]-3-oxo-4-(tetrahydro-2H-pyran-4-yl)butanamide (41 mg, 0.104 mmol) to give 2-(3-methylquinoxalin-2-yl)-7-(tetrahydro-2H-pyran-4-ylmethyl)pyrazolo[1,5-a]pyrimidin-5-ol. MS (ESI): m/z 374 (M–H).

(e)

The preparation was performed in a similar manner as Example 1.001 (f) from 2-(3-methylquinoxalin-2-yl)-7-(tetrahydro-2H-pyran-4-ylmethyl)pyrazolo[1,5-a]pyrimidin-5-ol (18 mg, 0.047 mmol) to give 2-[5-chloro-7-(tetrahydro-2H-pyran-4-ylmethyl)pyrazolo[1,5-a]pyrimidin-2-yl]-3-methylquinoxaline. MS (APCI): m/z 394/396 (M+H).

(f)

The preparation was performed in a similar manner as Example 1.001 (h) from 2-[5-chloro-7-(tetrahydro-2H-pyran-4-ylmethyl)pyrazolo[1,5-a]pyrimidin-2-yl]-3-methylquinoxaline (16 mg, 0.041 mmol) to give 2-methyl-3-[5-pyrrolidin-1-yl-7-(tetrahydro-2H-pyran-4-ylmethyl)pyrazolo[1,5-a]pyrimidin-2-yl]quinoxaline (the compound of Example 2.001 listed in the Table of Examples as described hereinafter). $^1$H-NMR (400 MHz, CDCl$_3$): δ 1.43-1.53 (2H, m), 1.67-1.71 (2H, m), 2.01-2.08 (5H, m), 2.36-2.41 (1H, m), 3.03 (2H, d, J=7.0 Hz), 3.12 (3H, s), 3.28-3.40 (3H, m), 3.97 (2H, dd, J=11.3, 3.2 Hz), 6.00 (1H, s), 6.86 (1H, s), 7.68-7.75 (2H, m), 8.01-8.06 (1H, m), 8.12-8.16 (1H, m).

Example 3.001

(a)

A mixture of 3-(3-methylquinoxalin-2-yl)-1H-pyrazol-5-amine (Example 1.001 (c)) (200 mg, 0.888 mmol), ethyl 3-cyclopropyl-3-oxopropanoate (416 mg, 2.66 mmol), and sodium methoxide (28% in methanol, 1.03 g, 5.34 mmol) in 2-methoxyethanol (2.0 mL) was refluxed for 10 h. After being cooled to ambient temperature, the reaction mixture was acidified to pH 3-4 with acetic acid. The mixture was diluted with water and the resulting precipitate was collected and washed with diisopropyl ether to give 5-cyclopropyl-2-(3-methylquinoxalin-2-yl)pyrazolo[1,5-a]pyrimidin-7-ol. MS (APCI): m/z 318 (M+H).

(b)

The preparation was performed in a similar manner as Example 1.001 (f) from 5-cyclopropyl-2-(3-methylquinoxalin-2-yl)pyrazolo[1,5-a]pyrimidin-7-ol (153 mg, 0.481 mmol) to give 2-(7-chloro-5-cyclopropylpyrazolo[1,5-a]pyrimidin-2-yl)-3-methylquinoxaline. MS (APCI): m/z 336/338 (M+H).

(c)

The preparation was performed in a similar manner as Example 1.001 (g) from 2-(7-chloro-5-cyclopropylpyrazolo[1,5-a]pyrimidin-2-yl)-3-methylquinoxaline (140 mg, 0.418 mmol) to give 5-cyclopropyl-2-(3-methylquinoxalin-2-yl)-N-(tetrahydro-2H-pyran-4-yl)pyrazolo[1,5-a]pyrimidin-7-amine (the compound of Example 3.001 listed in the Table of Examples as described hereinafter). $^1$H-NMR (400 MHz, DMSO-d$_6$): δ 1.31-1.42 (4H, m), 1.80-2.02 (4H, m), 2.26-2.37 (1H, m), 3.08 (3H, s), 3.49 (2H, ddd, J=11.8, 11.8, 1.8 Hz), 3.96 (2H, dd, J=10.6, 3.3 Hz), 4.18-4.37 (1H, m), 6.50 (1H, s), 7.09 (1H, s), 7.83-7.94 (2H, m), 8.09 (1H, dd, J=7.9, 1.8 Hz), 8.17 (1H, dd, J=7.9, 1.8 Hz), 9.18-9.36 (1H, m).

Example 4.001

5-Pyrrolidin-1-yl-N-(tetrahydro-2H-pyran-4-yl)-2-[3-(trifluoromethyl)quinoxalin-2-yl]pyrazolo[1,5-a]pyrimidin-7-amine (50 mg, 0.0962 mmol) was neutralized by saturated sodium bicarbonate, and the mixture was extracted with chloroform. The organic layer was dried over sodium sulfate, filtrated and concentrated in vacuo. The crude material and N-bromosuccinimide (17 mg, 0.0962 mmol) in chloroform (1.0 mL) was stirred at 0° C. for 50 min. Then the reaction mixture was poured into saturated sodium bicarbonate, and the mixture was extracted with chloroform. The organic layer was dried over sodium sulfate, filtrated and concentrated in vacuo. The crude was purified by silica gel column chromatography (hexane:ethyl acetate=3:1 to 1:1) to 3-bromo-5-pyrrolidin-1-yl-N-(tetrahydro-2H-pyran-4-yl)-2-[3-(trifluoromethyl)quinoxalin-2-yl]pyrazolo[1,5-a]pyrimidin-7-amine (the compound of Example 4.001 listed in the Table of Examples as described hereinafter). $^1$H-NMR (500 MHz, DMSO-d$_6$): δ 1.67-1.75 (2H, m), 1.86-1.89 (2H, m), 1.97 (4H, br), 3.44-3.48 (2H, m), 3.53 (4H, br), 3.87-3.89 (3H, m), 5.56 (1H, s), 7.13 (1H, d, J=8.7 Hz), 8.14-8.20 (2H, m), 8.33-8.35 (1H, m), 8.39-8.41 (1H, m).

Example 4.002

The preparation was performed in a similar manner as Example 1.001 (a) Method A from 3-bromo-5-pyrrolidin-1-yl-N-(tetrahydro-2H-pyran-4-yl)-2-[3-(trifluoromethyl)quinoxalin-2-yl]pyrazolo[1,5-a]pyrimidin-7-amine (30 mg, 0.0533 mmol) to give 3-methyl-5-pyrrolidin-1-yl-N-(tetrahydro-2H-pyran-4-yl)-2-[3-(trifluoromethyl)quinoxalin-2-yl]pyrazolo[1,5-a]pyrimidin-7-amine (the compound of Example 4.002 listed in the Table of Examples as described hereinafter). $^1$H-NMR (400 MHz, DMSO-d$_6$): δ 1.62-1.72

(2H, m), 1.89-1.93 (2H, m), 1.94-1.97 (4H, m), 2.05 (3H, s), 3.45-3.53 (6H, m), 3.86-3.89 (3H, m), 5.49 (1H, s), 6.70 (1H, d, J=8.8 Hz), 8.07-8.15 (2H, m), 8.28-8.30 (1H, m), 8.34-8.36 (1H, m).

Examples 4.003 to 4.005

The compounds of Examples 4.003 to 4.005 listed in the Table of Examples as described hereinafter were obtained in the similar manner as described in the above Example 4.001.

Example 5.001 and 5.002

(a)

To a solution of ethyl 5-aminopyrazole-3-carboxylate (5.00 g, 26.1 mmol) and ethyl hydrogen malonate (3.62 g, 27.4 mmol) in pyridine (130 mL) was added N,N'-diisopropylcarbodiimide (4.28 g, 33.9 mmol) at 0° C. After being stirred at same temperature, the reaction mixture was poured into water. The mixture was extracted with ethyl acetate and the organic layer was washed with saturated brine, dried over sodium sulfate, filtrated and concentrated in vacuo. The crude was purified by silica gel column chromatography (chloroform to chloroform:methanol=19:1) and triturated with diisopropyl ether to give ethyl 5-[(3-ethoxy-3-oxopropanoyl) amino]-1H-pyrazole-3-carboxylate. MS (APCI): m/z 270 (M+H).

(b)

To a suspension of ethyl 5-[(3-ethoxy-3-oxopropanoyl) amino]-1H-pyrazole-3-carboxylate (2.60 g, 9.66 mmol) in ethanol (50 mL) and water (50 mL) was added N,N-dimethylaminopyridine (3.54 g, 29.0 mmol) at room temperature. After being stirred for 22 h, the reaction mixture was concentrated in vacuo. The residue was triturated with ethyl acetate/ethanol to give ethyl 5,7-dihydroxypyrazolo[1,5-a]pyrimidine-2-carboxylate. MS (APCI): m/z 224 (M+H), 123 (M+H, DMAP).

(c)

A suspension of ethyl 5,7-dihydroxypyrazolo[1,5-a]pyrimidine-2-carboxylate (9.59 g, 43.0 mmol) and phosphorous oxychloride (20.0 mL, 215 mmol) was refluxed for 1 hr. After being cooled to ambient temperature, the reaction mixture was poured into saturated sodium bicarbonate and chloroform. The organic layer was separated and aqueous layer was extracted with chloroform. The organic layer was combined and concentrated in vacuo to give ethyl 5,7-dichloropyrazolo [1,5-a]pyrimidine-2-carboxylate. MS (APCI): m/z 260/262 (M+H).

(d)

To a solution of ethyl 5,7-dichloropyrazolo[1,5-a]pyrimidine-2-carboxylate (7.82 g, 30.1 mmol) in N,N-dimethylformamide (100 mL) was added 4-amino-tetrahydropyran (3.65 g, 36.1 mmol) and triethylamine (9.12 g, 90.2 mmol) at 0° C. The reaction mixture was stirred for 70 min at room temperature, and then pored into water. The resulting precipitate was collected to give ethyl 5-chloro-7-(tetrahydro-2H-pyran-4-ylamino)pyrazolo[1,5-a]pyrimidine-2-carboxylate. MS (APCI): m/z 325 (M+H).

(e)

To a solution of ethyl 5-chloro-7-(tetrahydro-2H-pyran-4-ylamino)pyrazolo[1,5-a]pyrimidine-2-carboxylate (5.88 g, 18.1 mmol) in N,N-dimethylacetamide (50 mL) was added triethylamine (5.50 g, 54.3 mmol) and pyrrolidine (1.59 mL, 19.0 mmol) at 0° C. The mixture was heated at 60° C. for 20 h. And then pyrrolidine (1.59 mL, 19.0 mmol) was added and heated at 60° C. for 24 h. After being cooled to ambient temperature, the reaction mixture was poured into water. The resulting precipitate was collected to give ethyl 5-pyrrolidin-1-yl-7-(tetrahydro-2H-pyran-4-ylamino)pyrazolo[1,5-a]pyrimidine-2-carboxylate. MS (APCI): m/z 360 (M+H).

(f)

To a solution of ethyl 5-pyrrolidin-1-yl-7-(tetrahydro-2H-pyran-4-ylamino)pyrazolo[1,5-a]pyrimidine-2-carboxylate (1.89 g, 5.26 mmol) in ethanol (25 mL) and tetrahydrofuran (25 mL) was added 1N aqueous sodium hydroxide (10.5 mL, 10.5 mmol) at room temperature. After being stirred for 23 h at same temperature, 6N aqueous hydrochloric acid (1.75 mL, 3.50 mmol), and then the reaction mixture was concentrated in vacuo. The residue was triturated with diisopropyl ether to give 5-pyrrolidin-1-yl-7-(tetrahydro-2H-pyran-4-ylamino) pyrazolo[1,5-a]pyrimidine-2-carboxylic acid. MS (APCI): m/z 330 (M−H).

(g)

To a suspension of 5-pyrrolidin-1-yl-7-(tetrahydro-2H-pyran-4-ylamino)pyrazolo[1,5-a]pyrimidine-2-carboxylic acid (2.15 g, 5.26 mmol) in dichloromethane (60 mL) was added 1-ethyl-3-(3-dimethylaminopropyl)carbodiimide hydrochloride (1.27 g, 13.0 mmol), N,O-dimethylhydroxylamine hydrochloride (2.49 g, 13.0 mmol), and triethylamine (2.30 g, 22.7 mmol) at 0° C. After being stirred for 17 h at room temperature, the reaction mixture was poured into saturated sodium bicarbonate. The mixture was extracted with chloroform. The organic layer was washed with brine, dried over sodium sulfate, filtrated and concentrated in vacuo. The crude was purified by silica gel column chromatography (chloroform to chloroform:methanol=19:1) to give N-methoxy-N-methyl-5-pyrrolidin-1-yl-7-(tetrahydro-2H-pyran-4-ylamino)pyrazolo[1,5-a]pyrimidine-2-carboxamide. MS (APCI): m/z 375 (M+H).

(h)

To a suspension of N-methoxy-N-methyl-5-pyrrolidin-1-yl-7-(tetrahydro-2H-pyran-4-ylamino)pyrazolo[1,5-a]pyrimidine-2-carboxamide (4.34 g, 11.6 mmol), di-tert-butyl dicarbonate (15.2 g, 69.6 mmol), and N,N-dimethylaminopyridine (1.49 g, 12.1 mmol) in tetrahydrofuran (100 mL) was stirred at room temperature for 3 days, and then heated at 50° C. for 10 h. After being cooled to ambient temperature, the reaction mixture was poured into water. The mixture was extracted with chloroform. The organic layer was washed with brine, dried over sodium sulfate, filtrated and concentrated in vacuo. The crude was purified by silica gel column chromatography (chloroform:ethyl acetate=13:7 to ethyl acetate to ethyl acetate:methanol 4:1) to give tert-butyl (2-{[methoxy(methyl)amino]carbonyl}-5-pyrrolidin-1-ylpyrazolo[1,5-a]pyrimidin-7-yl)tetrahydro-2H-pyran-4-ylcarbamate. MS (APCI): m/z 475 (M+H).

(i)

To a solution of tert-butyl (2-{[methoxy(methyl)amino] carbonyl}-5-pyrrolidin-1-ylpyrazolo[1,5-a]pyrimidin-7-yl) tetrahydro-2H-pyran-4-ylcarbamate (2.22 g, 4.68 mmol) in tetrahydrofuran (50 mL) was added ethylmagnesium bromide solution (1M in tetrahydrofuran, 14.0 mL, 14.0 mmol) at 0° C. After being stirred for 20 min at same temperature, the reaction mixture was poured into saturated ammonium chloride. The mixture was extracted with chloroform. The organic layer was dried over sodium sulfate, filtrated and concentrated in vacuo. The crude was purified by silica gel column chromatography (chloroform to chloroform:ethyl acetate=3: 2) to give tert-butyl (2-propionyl-5-pyrrolidin-1-ylpyrazolo [1,5-a]pyrimidin-7-yl)tetrahydro-2H-pyran-4-ylcarbamate. MS (APCI): m/z 444 (M+H).

(j)

To a suspension of tert-butyl (2-propionyl-5-pyrrolidin-1-ylpyrazolo[1,5-a]pyrimidin-7-yl)tetrahydro-2H-pyran-4-yl-carbamate (500 mg, 1.13 mmol) and sodium nitrite (233 mg, 3.38 mmol) in tetrahydrofuran (10 mL) was added conc. hydrochloric acid solution (36%, 5.0 mL) at 0° C. After being stirred for 20 h at room temperature, the reaction mixture was poured into saturated sodium bicarbonate. The mixture was extracted with chloroform. The organic layer was dried over sodium sulfate, filtrated and concentrated in vacuo. The crude was purified by silica gel column chromatography (chloroform:ethyl acetate=1:1 to 1:9) to give 1-[5-pyrrolidin-1-yl-7-(tetrahydro-2H-pyran-4-ylamino)-pyrazolo[1,5-a]pyrimidin-2-yl]propane-1,2-dione. MS (APCI): m/z 358 (M+H).

(k)

To a solution of 1-[5-pyrrolidin-1-yl-7-(tetrahydro-2H-pyran-4-ylamino)-pyrazolo[1,5-a]pyrimidin-2-yl]propane-1,2-dione (87 mg, 0.243 mmol) in methanol (3 mL) and water (0.3 mL) was added 3,4-diaminopyridine (29 mg, 0.268 mmol) at room temperature. After being stirred for 24 h at same temperature, the reaction mixture was concentrated in vacuo. The crude was purified by silica gel column chromatography (chloroform:methanol=99:1 to 19:1) and HPLC(CHIRAL-PAK IC, 20Φ×250 mm, hexane:ethanol:diethylamine=30:70: 0.1, frow rate 5.0 mL/min) to give 2-(3-methylpyrido[3,4-b] pyrazin-3-yl)-5-pyrrolidin-1-yl-N-(tetrahydro-2H-pyran-4-yl)pyrazolo[1,5-a]pyrimidin-7-amine (the compound of Example 5.001 listed in the Table of Examples as described hereinafter) as a more polar compound and 2-(2-methylpyrido[3,4-b]pyrazin-2-yl)-5-pyrrolidin-1-yl-N-(tetrahydro-2H-pyran-4-yl)pyrazolo[1,5-a]pyrimidin-7-amine (the compound of Example 5.002 listed in the Table of Examples as described hereinafter) as a less polar compound. The absolute configuration was determined by X-ray analysis of 2-(2-methylpyrido[3,4-b]pyrazin-2-yl)-5-pyrrolidin-1-yl-N-(tetrahydro-2H-pyran-4-yl)pyrazolo[1,5-a]pyrimidin-7-amine.

more polar compound, MS (APCI): m/z 358 (M+H), $^1$H NMR (400 MHz, CDCl$_3$) δ: 9.58 (1H, s), 8.79 (1H, d, J=5.7 Hz), 7.87 (1H, d, J=5.7 Hz), 6.70 (1H, s), 6.07 (1H, d, J=8.2 Hz), 5.21 (1H, s), 4.08 (2H, dt, J=11.9, 3.4 Hz), 3.68-3.75 (1H, m), 3.57-3.62 (6H, m), 3.10 (3H, s), 2.13-2.16 (2H, m), 2.03-2.07 (4H, m), 1.72-1.82 (2H, m). less polar compound, MS (APCI): m/z 358 (M+H), $^1$H NMR (400 MHz, CDCl$_3$) δ: 9.48 (1H, s), 8.78 (1H, d, J=5.7 Hz), 7.99 (1H, d, J=5.7 Hz), 6.73 (1H, s), 6.07 (1H, d, J=8.2 Hz), 5.21 (1H, s), 4.08 (2H, dt, J=11.9, 3.6 Hz), 3.68-3.75 (1H, m), 3.57-3.62 (6H, m), 3.11 (3H, s), 2.13-2.16 (2H, m), 2.03-2.07 (4H, m), 1.72-1.82 (2H, m).

Reference Example 1.01

(a)

The preparation was performed in a similar manner as Example 1.001 (b) from ethyl 3,5-dimethylquinoxaline 2-carboxylate (1.03 g, 4.47 mmol) to give 3-(3,5-dimethylquinoxalin-2-yl)-3-oxopropanenitrile. MS (APCI): m/z 226 (M+H).

(b)

The preparation was performed in a similar manner as Example 1.001 (c) from 3-(3,5-dimethylquinoxalin-2-yl)-3-oxopropanenitrile (797 mg, 3.54 mmol) to give 3-(3,5-dimethylquinoxalin-2-yl)-1H-pyrazol-5-amine. MS (APCI): m/z 240 (M+H).

(c)

The preparation was performed in a similar manner as Example 1.001 (d) Method A from 3-(3,5-dimethylquinoxalin-2-yl)-1H-pyrazol-5-amine (783 mg, 3.27 mmol) to give ethyl 3-{[3-(3,5-dimethylquinoxalin-2-yl)-1H-pyrazol-5-yl] amino}-3-oxopropanoate. MS (APCI): m/z 354 (M+H).

(d)

The preparation was performed in a similar manner as Example 1.001 (e) Method A from ethyl 3-{[3-(3,5-dimethylquinoxalin-2-yl)-1H-pyrazol-5-yl]amino}-3-oxopropanoate (1.17 g, 3.31 mmol) to give 2-(3,5-dimethylquinoxalin-2-yl)pyrazolo[1,5-a]pyrimidine-5,7-diol. MS (ESI): m/z 306 (M−H).

(e)

The preparation was performed in a similar manner as Example 1.001 (f) from 2-(3,5-dimethylquinoxalin-2-yl) pyrazolo[1,5-a]pyrimidine-5,7-diol (997 mg, 3.24 mmol) to give 2-(5,7-dichloropyrazolo[1,5-a]pyrimidin-2-yl)-3,5-dimethylquinoxaline (the compound of Reference Example 1.01 listed in the Table of Reference Examples as described hereinafter).

Reference Example 1.02

(a)

The preparation was performed in a similar manner as Example 1.001 (b) from ethyl 3,6-dimethylquinoxaline 2-carboxylate (555 mg, 2.41 mmol) to give 3-(3,6-dimethylquinoxalin-2-yl)-3-oxopropanenitrile. MS (APCI): m/z 226 (M+H).

(b)

The preparation was performed in a similar manner as Example 1.001 (c) from 3-(3,6-dimethylquinoxalin-2-yl)-3-oxopropanenitrile (385 mg, 1.71 mmol) to give 3-(3,6-dimethylquinoxalin-2-yl)-1H-pyrazol-5-amine. MS (APCI): m/z 240 (M+H).

(c)

The preparation was performed in a similar manner as Example 1.001 (d) Method A from 3-(3,6-dimethylquinoxalin-2-yl)-1H-pyrazol-5-amine (347 mg, 1.45 mmol) to give ethyl 3-{[3-(3,6-dimethylquinoxalin-2-yl)-1H-pyrazol-5-yl] amino}-3-oxopropanoate. MS (APCI): m/z 354 (M+H).

(d)

The preparation was performed in a similar manner as Example 1.001 (e) Method A from ethyl 3-{[3-(3,6-dimethylquinoxalin-2-yl)-1H-pyrazol-5-yl]amino}-3-oxopropanoate (452 mg, 1.28 mmol) to give 2-(3,6-dimethylquinoxalin-2-yl)pyrazolo[1,5-a]pyrimidine-5,7-diol. MS (ESI): m/z 306 (M−H).

(e)

The preparation was performed in a similar manner as Example 1.001 (f) from 2-(3,6-dimethylquinoxalin-2-yl)pyrazolo[1,5-a]pyrimidine-5,7-diol (383 mg, 1.25 mmol) to give 2-(5,7-dichloropyrazolo[1,5-a]pyrimidin-2-yl)-3,6-dimethylquinoxaline (the compound of Reference Example 1.02 listed in the Table of Reference Examples as described hereinafter). MS (APCI): m/z 344/346 (M+H).

Reference Example 1.03

(a)

The preparation was performed in a similar manner as Example 1.001 (b) from ethyl 3,7-dimethylquinoxaline 2-carboxylate (10.0 g, 43.4 mmol) to give 3-(3,7-dimethylquinoxalin-2-yl)-3-oxopropanenitrile. MS (APCI): m/z 226 (M+H).

(b)

The preparation was performed in a similar manner as Example 1.001 (c) from 3-(3,7-dimethylquinoxalin-2-yl)-3-oxopropanenitrile (8.11 g, 36.0 mmol) to give 3-(3,7-dimethylquinoxalin-2-yl)-1H-pyrazol-5-amine. MS (APCI): m/z 240 (M+H).

(c)

The preparation was performed in a similar manner as Example 1.001 (d) Method A from 3-(3,7-dimethylquinoxalin-2-yl)-1H-pyrazol-5-amine (300 mg, 1.25 mmol) to give ethyl 3-{[3-(3,7-dimethylquinoxalin-2-yl)-1H-pyrazol-5-yl]amino}-3-oxopropanoate. MS (APCI): m/z 354 (M+H).

(d)

The preparation was performed in a similar manner as Example 1.001 (e) Method A from ethyl 3-{[3-(3,7-dimethylquinoxalin-2-yl)-1H-pyrazol-5-yl]amino}-3-oxopropanoate (700 mg, 1.98 mmol) to give 2-(3,7-dimethylquinoxalin-2-yl)pyrazolo[1,5-a]pyrimidine-5,7-diol. MS (ESI): m/z 306 (M−H).

(e)

The preparation was performed in a similar manner as Example 1.001 (f) from 2-(3,7-dimethylquinoxalin-2-yl)pyrazolo[1,5-a]pyrimidine-5,7-diol (1.39 g, 4.52 mmol) to give 3-(5,7-dichloropyrazolo[1,5-a]pyrimidin-2-yl)-2,6-dimethylquinoxaline (the compound of Reference Example 1.03 listed in the Table of Reference Examples as described hereinafter).

Reference Example 1.04

(a)

The preparation was performed in a similar manner as Example 1.001 (b) from ethyl 3,8-dimethylquinoxaline 2-carboxylate (1.50 g, 6.51 mmol) to give 3-(3,8-dimethylquinoxalin-2-yl)-3-oxopropanenitrile. MS (APCI): m/z 226 (M+H).

(b)

The preparation was performed in a similar manner as Example 1.001 (c) from 3-(3,8-dimethylquinoxalin-2-yl)-3-oxopropanenitrile (400 mg, 1.78 mmol) to give 3-(3,8-dimethylquinoxalin-2-yl)-1H-pyrazol-5-amine. MS (APCI): m/z 240 (M+H).

(c)

The preparation was performed in a similar manner as Example 1.001 (d) Method A from 3-(3,8-dimethylquinoxalin-2-yl)-1H-pyrazol-5-amine (250 mg, 1.04 mmol) to give ethyl 3-{[3-(3,8-dimethylquinoxalin-2-yl)-1H-pyrazol-5-yl]amino}-3-oxopropanoate. MS (APCI): m/z 354 (M+H).

(d)

The preparation was performed in a similar manner as Example 1.001 (e) Method A from ethyl 3-{[3-(3,8-dimethylquinoxalin-2-yl)-1H-pyrazol-5-yl]amino}-3-oxopropanoate (158 mg, 0.447 mmol) to give 2-(3,8-dimethylquinoxalin-2-yl)pyrazolo[1,5-a]pyrimidine-5,7-diol. MS (APCI): m/z 308 (M+H).

(e)

The preparation was performed in a similar manner as Example 1.001 (f) from 2-(3,8-dimethylquinoxalin-2-yl)pyrazolo[1,5-a]pyrimidine-5,7-diol (316 mg, 1.01 mmol) to give 3-(5,7-dichloropyrazolo[1,5-a]pyrimidin-2-yl)-2,5-dimethylquinoxaline (the compound of Reference Example 1.04 listed in the Table of Reference Examples as described hereinafter).

Reference Example 1.05

(a)

The preparation was performed in a similar manner as Example 1.001 (b) from ethyl 3-methyl-7-trifluoromethylquinoxaline 2-carboxylate (15.0 g, 52.8 mmol) to give methyl 3-methyl-7-(trifluoromethyl)quinoxaline-2-carboxylate. MS (APCI): m/z 280 (M+H).

(b)

The preparation was performed in a similar manner as Example 1.001 (c) from methyl 3-methyl-7-(trifluoromethyl)quinoxaline-2-carboxylate (2.11 g, 7.56 mmol) to give 3-[3-methyl-7-(trifluoromethyl)quinoxalin-2-yl]-1H-pyrazol-5-amine. MS (APCI): m/z 294 (M+H).

(c)

The preparation was performed in a similar manner as Example 1.001 (d) Method A from 3-[3-methyl-7-(trifluoromethyl)quinoxalin-2-yl]-1H-pyrazol-5-amine (2.13 g, 7.25 mmol) to give ethyl 3-({3-[3-methyl-7-(trifluoromethyl)quinoxalin-2-yl]-1H-pyrazol-5-yl}amino)-3-oxopropanoate. MS (APCI): m/z 408 (M+H).

(d)

The preparation was performed in a similar manner as Example 1.001 (e) Method A from ethyl 3-({3-[3-methyl-7-

(trifluoromethyl)quinoxalin-2-yl]-1H-pyrazol-5-yl}amino)-3-oxopropanoate (2.29 g, 5.63 mmol) to give 2-[3-methyl-7-(trifluoromethyl)quinoxalin-2-yl]pyrazolo[1,5-a]pyrimidine-5,7-diol. MS (ESI): m/z 360 (M−H).

(e)

The preparation was performed in a similar manner as Example 1.001 (f) from 2-[3-methyl-7-(trifluoromethyl)quinoxalin-2-yl]pyrazolo[1,5-a]pyrimidine-5,7-diol (2.00 g, 5.54 mmol) to give 3-(5,7-dichloropyrazolo[1,5-a]pyrimidin-2-yl)-2-methyl-6-(trifluoromethyl)quinoxaline (the compound of Reference Example 1.05 listed in the Table of Reference Examples as described hereinafter).

Reference Example 1.06

(a)

The preparation was performed in a similar manner as Example 1.001 (b) from ethyl 5-fluoro-3,7-dimethylquinoxaline 2-carboxylate (970 mg, 3.91 mmol) to give 3-(5-fluoro-3,7-dimethylquinoxalin-2-yl)-3-oxopropanenitrile. MS (APCI): m/z 244 (M+H).

(b)

The preparation was performed in a similar manner as Example 1.001 (c) from 3-(5-fluoro-3,7-dimethylquinoxalin-2-yl)-3-oxopropanenitrile (250 mg, 1.03 mmol) to give 3-(5-fluoro-3,7-dimethylquinoxalin-2-yl)-1H-pyrazol-5-amine. MS (APCI): m/z 258 (M+H).

(c)

The preparation was performed in a similar manner as Example 1.001 (d) Method A from 3-(5-fluoro-3,7-dimethylquinoxalin-2-yl)-1H-pyrazol-5-amine (262 mg, 1.02 mmol) to give ethyl 3-{[3-(5-fluoro-3,7-dimethylquinoxalin-2-yl)-1H-pyrazol-5-yl]amino}-3-oxopropanoate. MS (APCI): m/z 372 (M+H).

(d)

The preparation was performed in a similar manner as Example 1.001 (e) Method A from ethyl 3-{[3-(5-fluoro-3,7-dimethylquinoxalin-2-yl)-1H-pyrazol-5-yl]amino}-3-oxopropanoate (224 mg, 0.605 mmol) to give 2-(5-fluoro-3,7-dimethylquinoxalin-2-yl)pyrazolo[1,5-a]pyrimidine-5,7-diol. MS (ESI): m/z 324 (M−H).

(e)

The preparation was performed in a similar manner as Example 1.001 (f) from 2-(5-fluoro-3,7-dimethylquinoxalin-2-yl)pyrazolo[1,5-a]pyrimidine-5,7-diol (198 mg, 0.605 mmol) to give 2-(5,7-dichloropyrazolo[1,5-a]pyrimidin-2-yl)-5-fluoro-3,7-dimethylquinoxaline (the compound of Reference Example 1.06 listed in the Table of Reference Examples as described hereinafter).

Reference Example 1.07

(a)

To a solution of D-alanamide hydrochloride (18.5 g, 149 mmol) in methanol (230 mL) and water (23 mL) was added 50% aqueous sodium hydroxide (13.5 g, 338 mmol) at −10° C., and then 1,2-cyclohexanedione (15.1 g, 135 mmol) was added subsequently at same temperature. After being stirred overnight, the reaction mixture was neutralized with 2N aqueous hydrochloric acid and saturated aqueous sodium bicarbonate. The resulting precipitate was collected and washed with water and diisopropyl ether to give 2-hydroxy-3-methyl-4,5,6,7-tetrahydroquinoxaline. MS (APCI): m/z 165 (M+H).

(b)

A mixture of 2-hydroxy-3-methyl-4,5,6,7-tetrahydroquinoxaline (1.61 g, 9.78 mmol) and phosphorous(V) oxychloride (7.50 g, 48.9 mmol) was refluxed for 6 h. After being cooled to ambient temperature, the reaction mixture was concentrated in vacuo. The residue was poured into saturated sodium bicarbonate at 0° C., and the mixture was extracted with chloroform. The organic layer was washed with saturated brine, dried over sodium sulfate, filtrated and concentrated in vacuo. The residue was purified by silica gel column chromatography (hexane to hexane:ethyl acetate=17:3) to give 2-chloro-3-methyl-4,5,6,7-tetrahydroquinoxaline. MS (APCI): m/z 183/185 (M+H).

(c)

A mixture of 2-chloro-3-methyl-4,5,6,7-tetrahydroquinoxaline (1.16 g, 6.36 mmol), molybdeniumhexacarbonyl (2.35 g, 9.35 mmol), palladium(II) acetate (142 mg, 0.636 mmol), 2,2'-bis(diphenylphosphino)-1,1'-binaphtalene (396 mg, 0.636 mmol), cesium carbonate (2.07 g, 6.36 mmol), and ethanol (0.482 mL, 8.26 mmol) in toluene (19 mL) and acetonitrile (12 mL) was heated at 80° C. overnight. After being cooled to ambient temperature, the reaction mixture was filtrated with chloroform. The filtrate was combined and washed with water and brine. The organic layer was dried over sodium sulfate, filtrated and concentrated in vacuo. The residue was purified by silica gel column chromatography (hexane:ethyl acetate=97:3 to 3:2) to give ethyl 3-methyl-4,5,6,7-tetrahydroquinoxaline. MS (APCI): m/z 221 (M+H).

(d)

The preparation was performed in a similar manner as Example 1.001 (b) from ethyl 3-methyl-4,5,6,7-tetrahydroquinoxaline (2.39 g, 10.9 mmol) to give 3-(3-methyl-5,6,7,8-tetrahydroquinoxalin-2-yl)-3-oxopropanenitrile. MS (APCI): m/z 216 (M+H).

(e)

The preparation was performed in a similar manner as Example 1.001 (c) from 3-(3-methyl-5,6,7,8-tetrahydroquinoxalin-2-yl)-3-oxopropanenitrile (1.82 g, 8.46 mmol) to give 3-(3-methyl-5,6,7,8-tetrahydroquinoxalin-2-yl)-1H-pyrazol-5-amine. MS (APCI): m/z 230 (M+H).

(f)

The preparation was performed in a similar manner as Example 1.001 (d) Method A from 3-(3-methyl-5,6,7,8-tetrahydroquinoxalin-2-yl)-1H-pyrazol-5-amine (2.08 g, 8.46 mmol) and Example 1.001 (e) to give 2-(3-methyl-5,6,7,8-tetrahydroquinoxalin-2-yl)pyrazolo[1,5-a]pyrimidine-5,7-diol. MS (ESI): m/z 296 (M−H).

(g)

The preparation was performed in a similar manner as Example 1.001 (f) from 2-(3-methyl-5,6,7,8-tetrahydroquinoxalin-2-yl)pyrazolo[1,5-a]pyrimidine-5,7-diol (2.16 g, 6.93 mmol) to give 2-(5,7-dichloropyrazolo[1,5-a]pyrimidin-2-yl)-3-methyl-5,6,7,8-tetrahydroquinoxaline (the compound of Reference Example 1.07 listed in the Table of Reference Examples as described hereinafter).

Reference Example 1.08

(a)

A suspension of 3,5,6-trimethylpyrazine-2-yl)methanol (see *Bioorg. Med. Chem.* 2007, 15, 3315; 14.8 g, 97.2 mmol) and manganes(IV) oxide (30.0 g) in dichloromethane was stirred at room temperature for 3 days. The reaction mixture was filtered through Celite with dichloromethane. The filtrate was combined and concentrated in vacuo to give 3,5,6-trimethylpyrazine-2-carbardehyde. MS (APCI): m/z 151 (M+H).

(b)

To a solution of 3,5,6-trimethylpyrazine-2-carbardehyde (4.51 g, 30.0 mmol), 2-methyl-2-butene (12.8 mL, 120 mmol), and sodium dihydrogen phosphate dihydrate (4.68 g, 30.0 mmol) in tert-butanol (90 mL) and water (30 mL) was added 80% sodium chlorite (10.2 g, 90.0 mmol) portionwise at 0° C. After being stirred at room temperature for 50 min, the reaction mixture was poured into 2N aqueous hydrochloric acid. The mixture was extracted with chloroform and the organic layer was dried over sodium sulfate, filtrated and concentrated in vacuo to give 3,5,6-trimethylpyrazine-2-carboxylate. MS (ESI): m/z 165 (M–H).

(c)

To a solution of 3,5,6-trimethylpyrazine-2-carboxylate (5.38 g, 30.0 mmol) in methanol (90 mL) was added thionyl chloride (3.70 mL, 51.0 mmol) was added at 0° C. After being stirred at room temperature overnight, the reaction mixture was poured into saturated aqueous sodium bicarbonate. The mixture was extracted with ethyl acetate and the organic layer was washed with water and saturated brine, dried over sodium sulfate, filtrated and concentrated in vacuo to give methyl 3,5,6-trimethylpyrazine-2-carboxylate. MS (APCI): m/z 181 (M+H).

(d)

The preparation was performed in a similar manner as Example 1.001 (b) from methyl 3,5,6-trimethylpyrazine-2-carboxylate (2.91 g, 16.1 mmol) to give 3-oxo-3-(3,5,6-trimethylpyrazin-2-yl)propanenitrile. MS (APCI): m/z 190 (M+H).

(e)

The preparation was performed in a similar manner as Example 1.001 (c) from 3-oxo-3-(3,5,6-trimethylpyrazin-2-yl)propanenitrile (2.58 g, 13.6 mmol) to give 3-(3,5,6-trimethylpyrazin-2-yl)-1H-pyrazol-5-amine. MS (APCI): m/z 204 (M+H).

(f)

The preparation was performed in a similar manner as Example 1.001 (d) Method B from 3-(3,5,6-trimethylpyrazin-2-yl)-1H-pyrazol-5-amine (1.00 g, 4.92 mmol) to give ethyl 3-oxo-3-{[3-(3,5,6-trimethylpyrazin-2-yl)-1H-pyrazol-5-yl]amino}propanoate. MS (APCI): m/z 318 (M+H).

(g)

The preparation was performed in a similar manner as Example 1.001 (e) Method A from ethyl 3-oxo-3-{[3-(3,5,6-trimethylpyrazin-2-yl)-1H-pyrazol-5-yl]amino}propanoate (1.25 g, 3.94 mmol) to give 2-(3,5,6-trimethylpyrazin-2-yl)pyrazolo[1,5-a]pyrimidine-5,7-diol. MS (APCI): m/z 272 (M+H).

(h)

The preparation was performed in a similar manner as Example 1.001 (f) from 2-(3,5,6-trimethylpyrazin-2-yl)pyrazolo[1,5-a]pyrimidine-5,7-diol (1.16 g, 4.28 mmol) to give 2-(5,7-dichloropyrazolo[1,5-a]pyrimidin-2-yl)-3-methyl-5,6,7,8-tetrahydroquinoxaline (the compound of Reference Example 1.08 listed in the Table of Reference Examples as described hereinafter).

Reference Example 1.09

(a)

A mixture of 2-nitrobenzaldehyde (10.0 g, 66.2 mmol) and iron(II) sulfate heptahydrate (129 g, 464 mmol) in ethanol (150 mL) and water (150 mL) was heated at 100° C. for 5 min, and then 28% aqueous ammonia (173 mL) was added dropwise carefully at same temperature. The reaction mixture was filtrated through Celite with diethyl ether. The organic layer was washed with water and saturated brine, dried over sodium sulfate, filtrated and concentrated in vacuo to give the crude 2-aminobenzaldehyde.

A solution of 2-aminobenzaldehyde, 2-oxobutyric acid (13.5 g, 132 mmol), and sodium ethoxide (13.5 g, 198 mmol) in ethanol (331 mL) was refluxed for 20 h. After being cooled to 0° C., 96% sulfuric acid (10.6 mL, 97.9 mmol) was added. The reaction mixture was refluxed for 20 h. After being cooled to 0° C., the reaction mixture was basified to pH 8-9 with saturated sodium bicarbonate, and the mixture was extracted with chloroform. The organic layer was washed with water and saturated brine, dried over sodium sulfate, filtrated and concentrated in vacuo. The crude was purified by silica gel column chromatography (hexane:ethyl acetate=19:1 to 2:1) to give ethyl 3-methylquinoline-2-carboxylate. MS (APCI): m/z 218 (M+H).

(b)

The preparation was performed in a similar manner as Example 1.001 (b) from ethyl 3-methylquinoline-2-carboxylate (500 mg, 2.32 mmol) to give 3-(3-methylquinolin-2-yl)-3-oxopropanenitrile. MS (APCI): m/z 211 (M+H).

(c)

The preparation was performed in a similar manner as Example 1.001 (c) from 3-(3-methylquinolin-2-yl)-3-oxopropanenitrile (243 mg, 1.16 mmol) to give 3-(3-methylquinolin-2-yl)-1H-pyrazol-5-amine. MS (APCI): m/z 225 (M+H).

(d)

The preparation was performed in a similar manner as Example 1.001 (d) Method A from 3-(3-methylquinolin-2- yl)-1H-pyrazol-5-amine (250 mg, 1.11 mmol) to give ethyl 3-{[3-(3-methylquinolin-2-yl)-1H-pyrazol-5-yl]amino}-3-oxopropanoate. MS (APCI): m/z 339 (M+H).

(e)

The preparation was performed in a similar manner as Example 1.001 (e) Method A from ethyl 3-{[3-(3-methylquinolin-2-yl)-1H-pyrazol-5-yl]amino}-3-oxopropanoate (369 mg, 1.09 mmol) to give 2-(3-methylquinolin-2-yl)pyrazolo[1,5-a]pyrimidine-5,7-diol. MS (ESI): m/z 293 (M−H).

(f)

The preparation was performed in a similar manner as Example 1.001 (f) from 2-(3-methylquinolin-2-yl)pyrazolo[1,5-a]pyrimidine-5,7-diol (295 mg, 1.01 mmol) to give 2-(5,7-dichloropyrazolo[1,5-a]pyrimidin-2-yl)-3-methylquinoline (the compound of Reference Example 1.09 listed in the Table of Reference Examples as described hereinafter).

Reference Example 1.10

(a)

The preparation was performed in a similar manner as Example 1.001 (b) from methyl 4-methylqunoline-2-carboxylate (see *Chem. Pharm. Bull.* 1981, 29, 2485; 1.00 g, 4.97 mmol) to give 3-(4-methylquinolin-2-yl)-3-oxopropanenitrile. MS (APCI): m/z 211 (M+H).

(b)

The preparation was performed in a similar manner as Example 1.001 (c) from 3-(4-methylquinolin-2-yl)-3-oxopropanenitrile (674 mg, 3.35 mmol) to give 3-(4-methylquinolin-2-yl)-1H-pyrazol-5-amine. MS (APCI): m/z 225 (M+H).

(c)

The preparation was performed in a similar manner as Example 1.001 (d) Method A from 3-(4-methylquinolin-2-yl)-1H-pyrazol-5-amine (985 mg, 3.35 mmol) to give ethyl 3-{[3-(4-methylquinolin-2-yl)-1H-pyrazol-5-yl]amino}-3-oxopropanoate. MS (APCI): m/z 339 (M+H).

(d)

The preparation was performed in a similar manner as Example 1.001 (e) Method A from ethyl 3-{[3-(4-methylquinolin-2-yl)-1H-pyrazol-5-yl]amino}-3-oxopropanoate (1.32 g, 3.35 mmol) to give 2-(4-methylquinolin-2-yl)pyrazolo[1,5-a]pyrimidine-5,7-diol. MS (ESI): m/z 291 (M−H).

(e)

The preparation was performed in a similar manner as Example 1.001 (f) from 2-(4-methylquinolin-2-yl)pyrazolo[1,5-a]pyrimidine-5,7-diol (1.08 g, 3.32 mmol) to give 2-(5,7-dichloropyrazolo[1,5-a]pyrimidin-2-yl)-4-methylquinoline (the compound of Reference Example 1.10 listed in the Table of Reference Examples as described hereinafter).

Reference Example 1.11

(a)

To a solution of 3,6-dimethyl2-iodopyrazine (see *J. Org. Chem.* 1961, 26, 1907; 1.00 g, 4.27 mmol), in diethyl ether (13 mL) was added n-butyllithium (2.6 M in hexane, 1.64 mL, 4.27 mmol) dropwise at −35° C. After being stirred at same temperature for 10 min, the reaction mixture was poured into dry ice. The mixture was extracted with 4N aqueous sodium hydroxide, and then the aqueous layer was acidified with conc. Hydrochloric acid. The mixture was extracted with chloroform, and the organic layer was dried over sodium sulfate, filtrated and concentrated in vacuo The crude was triturated with diethyl ether to give 3,6-dimethylpyrazine-2-carboxylate. MS (ESI): m/z 151 (M−H).

(b)

The preparation was performed in a similar manner as Reference Example 1.08 (c) from 3,6-dimethylpyrazine-2-carboxylate (161 mg, 1.06 mmol) to give methyl 3,5,6-trimethylpyrazine-2-carboxylate.
MS (APCI): m/z 181 (M+H).

(c)

The preparation was performed in a similar manner as Example 1.001 (b) from methyl 3,6-dimethylpyrazine-2-carboxylate (2.38 g, 14.3 mmol) to give 3-(3,6-dimethylpyrazin-2-yl)-3-oxopropanenitrile. MS (APCI): m/z 176 (M+H).

(d)

The preparation was performed in a similar manner as Example 1.001 (c) from 3-(3,6-dimethylpyrazin-2-yl)-3-oxopropanenitrile (2.47 g, 14.1 mmol) to give 3-(3,6-dimethylpyrazin-2-yl)-1H-pyrazol-5-amine. MS (APCI): m/z 190 (M+H).

(e)

The preparation was performed in a similar manner as Example 1.001 (d) Method A from 3-(3,6-dimethylpyrazin-2-yl)-1H-pyrazol-5-amine (1.81 g, 9.56 mmol) to give ethyl 3-{[3-(3,6-dimethylpyrazin-2-yl)-1H-pyrazol-5-yl]amino}-3-oxopropanoate). MS (APCI): m/z 304 (M+H).

(f)

The preparation was performed in a similar manner as Example 1.001 (e) Method A from ethyl 3-{[3-(3,6-dimethylpyrazin-2-yl)-1H-pyrazol-5-yl]amino}-3-oxopropanoate (1.78 g, 5.87 mmol) to give 2-(3,6-dimethylpyrazin-2-yl)pyrazolo[1,5-c]pyrimidine-5,7-diol. MS (APCI): m/z 258 (M+H).

(g)

The preparation was performed in a similar manner as Example 1.001 (f) from 2-(3,6-dimethylpyrazin-2-yl)pyrazolo[1,5-a]pyrimidine-5,7-diol (750 mg, 2.92 mmol) to give 5,7-dichloro-2-(3,6-dimethylpyrazin-2-yl)pyrazolo[1,5-a]pyrimidine (the compound of Reference Example 1.11 listed in the Table of Reference Examples as described hereinafter).

Reference Example 1.12

(a)

The preparation was performed in a similar manner as described in *Helv. Chim. Acta.* 2001, 84, 2379 from 3,4- dimethyl-1,2-phenylenediamine (12.0 g, 52.6 mmol) to give ethyl 3,6,7-trimethylquinoxaline-2-carboxylate. MS (APCI): m/z 231 (M+H).

(b)

The preparation was performed in a similar manner as Example 1.001 (b) from ethyl 3,6,7-Trimethylquinoxaline-2-carboxylate (7.90 g, 34.3 mmol) to give 3-oxo-3-(3,6,7-trimethylquinoxalin-2-yl)propanenitrile. MS (APCI): m/z 240 (M+H).

(c)

The preparation was performed in a similar manner as Example 1.001 (c) from 3-oxo-3-(3,6,7-trimethylquinoxalin-2-yl)propanenitrile (5.18 g, 21.6 mmol) to give 3-(3,6,7-trimethylquinoxalin-2-yl)-1H-pyrazol-5-amine. MS (APCI): m/z 254 (M+H).

(d)

The preparation was performed in a similar manner as Example 1.001 (d) Method A from 3-(3,6,7-trimethylquinoxalin-2-yl)-1H-pyrazol-5-amine (3.90 g, 15.4 mmol) to give ethyl 3-oxo-3-{[3-(3,6,7-trimethylquinoxalin-2-yl)-1H-pyrazol-5-yl]amino}propanoate. MS (APCI): m/z 368 (M+H).

(e)

The preparation was performed in a similar manner as Example 1.001 (e) Method A from ethyl 3-oxo-3-{[3-(3,6,7-trimethylquinoxalin-2-yl)-1H-pyrazol-5-yl]amino}propanoate (1.06 g, 2.89 mmol) to give 2-(3,6,7-trimethylquinoxalin-2-yl)pyrazolo[1,5-a]pyrimidine-5,7-diol. MS (ESI): m/z 320 (M−H).

(f)

The preparation was performed in a similar manner as Example 1.001 (f) from 2-(3,6,7-trimethylquinoxalin-2-yl)pyrazolo[1,5-a]pyrimidine-5,7-diol (1.44 g, 2.89 mmol) to give 2-(5,7-dichloropyrazolo[1,5-a]pyrimidin-2-yl)-3,6,7-trimethylquinoxaline (the compound of Reference Example 1.12 listed in the Table of Reference Examples as described hereinafter).

Reference Example 1.13

(a)

N-(tert-butoxycarbonyl)glycine (22.4 g, 128 mmol), ethyl 2-amino-3-oxobutanoate (21.1 g, 116 mmol), ethyl-3-(3-dimethylaminopropyl)carbodiimide hydrochloride (28.9 g, 151 mmol), 1-hydroxybenzotriazole (23.1 g, 151 mmol), triethylamine (16.2 mL, 116 mmol), in chloroform (350 mL) was stirred for 13 h at room temperature, and then triethylamine (20.0 mL, 143 mmol) was added. After being stirred for 4 h at same temperature, the reaction mixture was poured into saturated aqueous sodium bicarbonate. The organic layer was separated and the aqueous layer was extracted with chloroform. The organic layer was combined, washed with saturated brine, dried over sodium sulfate, filtrated and concentrated in vacuo. The crude was purified by silica gel column chromatography (hexane:ethyl acetate=2:1 to 1:1) to give ethyl 2-{[N-(tert-butoxycarbonyl)glycyl]amino}-3-oxobutanoate. MS (APCI): m/z 320 (M+NH$_4$), 303 (M+H).

(b)

The preparation was performed in a similar manner as Example 1.172 (b) from ethyl 2-{[N-(tert-butoxycarbonyl)glycyl]amino}-3-oxobutanoate (22.1 g, 73.1 mmol) to give ethyl 6-hydroxy-3-methylpyrazine-2-carboxylate. MS (APCI): m/z 183 (M+H).

(c)

The preparation was performed in a similar manner as Reference Example 1.07 (b) from ethyl 6-hydroxy-3-methylpyrazine-2-carboxylate (6.73 g, 36.9 mmol) to give ethyl 6-chloro-3-methylpyrazine-2-carboxylate. MS (APCI): m/z 201/203 (M+H).

(d)

A suspension of ethyl 6-chloro-3-methylpyrazine-2-carboxylate (1.94 g, 9.67 mmol), isobutylboronic acid (1.97 g, 19.3 mmol), [1,1'-bis(diphenylphosphino)ferrocene]dichloropalladium(II)(212 mg, 0.290 mmol), and potassium carbonate (2.67 g, 19.3 mmol) in 1,4-dioxane (30 mL) was heated at 100° C. for 4.5 h. After being cooled to ambient temperature, the reaction mixture was diluted with ethyl acetate and filtrated through celite with ethyl acetate. The filtrate was combined and concentrated in vacuo. The residue was diluted ethyl acetate, and washed with saturated aqueous sodium bicarbonate and saturated brine, dried over sodium bicarbonate, filtrated and concentrated in vacuo. The residue was dissolved to dichloromethane, and the insoluble materials were filtered off. The filtrate was concentrated in vacuo. The residue was purified by silica gel column chromatography (hexane:ethyl acetate=9:1 to 3:1) to give ethyl 6-isobutyl-3-methylpyrazine-2-carboxylate. MS (APCI): m/z 223 (M+H).

(e)

The preparation was performed in a similar manner as Example 1.006 (a) method A from ethyl 6-isobutyl-3-methylpyrazine-2-carboxylate (1.76 g, 7.92 mmol) to give 3-(6-isobutyl-3-methylpyrazin-2-yl)-3-oxopropanenitrile. MS (APCI): m/z 218 (M+H).

(f)

The preparation was performed in a similar manner as Example 1.001 (c) from 3-(6-isobutyl-3-methylpyrazin-2-yl)-3-oxopropanenitrile (1.61 g, 7.41 mmol) to give 3-(6-isobutyl-3-methylpyrazin-2-yl)-1H-pyrazol-5-amine MS (APCI): m/z 232 (M+H).

(g)

The preparation was performed in a similar manner as Example 1.006 (c) Method A from 3-(6-isobutyl-3-methylpyrazin-2-yl)-1H-pyrazol-5-amine (1.25 g, 5.40 mmol) to give ethyl 3-{[3-(6-isobutyl-3-methylpyrazin-2-yl)-1H-pyrazol-5-yl]amino}-3-oxopropanoate. MS (APCI): m/z 346 (M+H).

(h)

A suspension of ethyl 3-{[3-(6-isobutyl-3-methylpyrazin-2-yl)-1H-pyrazol-5-yl]amino}-3-oxopropanoate (1.13 g, 3.29 mmol) and triethylamine (1.38 mL, 9.88 mmol) in methanol (9 mL), tetrahydrofuran (9 mL), and water (9 mL) was refluxed for 2 h. After being cooled to ambient temperature, the reaction mixture was acidified to pH 2 with 2N aqueous hydrochloric acid and concentrated in vacuo. The residue was triturated with water to give 2-(6-isobutyl-3-methylpyrazin-2-yl)pyrazolo[1,5-a]pyrimidine-5,7-diol. MS (APCI): m/z 300 (M+H).

(i)

The preparation was performed in a similar manner as Example 1.001 (f) from 2-(6-isobutyl-3-methylpyrazin-2-yl)pyrazolo[1,5-a]pyrimidine-5,7-diol (663 mg, 2.22 mmol) to give 5,7-dichloro-2-(6-isobutyl-3-methylpyrazin-2-yl)pyrazolo[1,5-a]pyrimidine (the compound of Reference Example 1.13 listed in the Table of Reference Examples as described hereinafter).

Reference Example 1.14

(a)

The preparation was performed in a similar manner as Example 1.001 (d) Method B from N-(tert-butoxycarbonyl)-L-alanine (5.62 g, 29.7 mmol) and L-threonine ethyl ester hydrochloride (4.58 g, 27.0 mmol) to give methyl N-(tert-butoxycarbonyl)-L-alanyl-L-threoninate. MS (APCI): m/z 305 (M+H).

(b)

To a solution of methyl N-(tert-butoxycarbonyl)-L-alanyl-L-threoninate (9.00 g, 29.6 mmol) in dichloromethane (90 mL) was added Dess-Martin periodinane (15.1 g, 35.5 mmol) at room temperature. After being stirred for 70 min, saturated aqueous sodium thiosulfate solution was added, then the reaction mixture was stirred for 15 min. The mixture was poured into saturated aqueous sodium bicarbonate, and the mixture was extracted with ethyl acetate. The organic layer was washed with saturated brine, dried over sodium sulfate, filtrated and concentrated in vacuo. The residue was purified by silica gel column chromatography (hexane:ethyl acetate=3:1 to 1:1) to give methyl (2S)-2-{[N-(tert-butoxycarbonyl)-L-alanyl]amino}-3-oxobutanoate. MS (APCI): m/z 303 (M+H).

(c)

A solution of methyl (2S)-2-{[N-(tert-butoxycarbonyl)-L-alanyl]amino}-3-oxobutanoate (3.05 g, 10.1 mmol) and 4N hydrochloric acid in 1,4-dioxane (10 mL) was stirred at room temperature. After being stirred for 1 h at same temperature, the reaction mixture was concentrated in vacuo. A solution of the residue in pyridine (50 mL) was heated at 60° C. for 4 h. After being cooled to ambient temperature, the mixture was concentrated in vacuo. The residue was poured into water, and the mixture was extracted with dichloromethane. The organic layer was washed with saturated brine, dried over magnesium sulfate, filtrated and concentrated in vacuo. The residue was triturated with hexane-ethyl acetate (1:1) to give methyl 6-hydroxy-3,5-dimethylpyrazine-2-carboxylate. MS (APCI): m/z 183 (M+H).

(d)

The preparation was performed in a similar manner as Reference Example 1.07 (b) from methyl 6-hydroxy-3,5-dimethylpyrazine-2-carboxylate (4.55 g, 25.0 mmol) to give methyl 6-chloro-3,5-dimethylpyrazine-2-carboxylate. MS (APCI): m/z 201/203 (M+H).

(e)

The preparation was performed in a similar manner as Reference Example 1.13 (d) from methyl 6-chloro-3,5-dimethylpyrazine-2-carboxylate (960 mg, 4.78 mmol) to give methyl 6-isobutyl-3,5-dimethylpyrazine-2-carboxylate. MS (APCI): m/z 223 (M+H).

(f) The preparation was performed in a similar manner as Example 1.006 (a) method A from methyl 6-isobutyl-3,5-dimethylpyrazine-2-carboxylate (945 mg, 4.25 mmol) to give 3-(6-isobutyl-3,5-dimethylpyrazin-2-yl)-3-oxopropanenitrile. MS (APCI): m/z 232 (M+H).

(g)

The preparation was performed in a similar manner as Example 1.001 (c) from 3-(6-isobutyl-3,5-dimethylpyrazin-2-yl)-3-oxopropanenitrile (972 mg, 4.20 mmol) to give 3-(6-isobutyl-3,5-dimethylpyrazin-2-yl)-1H-pyrazol-5-amine. MS (APCI): m/z 246 (M+H).

(h)

The preparation was performed in a similar manner as Example 1.006 (c) Method A from 3-(6-isobutyl-3,5-dimethylpyrazin-2-yl)-1H-pyrazol-5-amine (950 mg, 3.87 mmol) to give ethyl 3-{[3-(6-isobutyl-3,5-dimethylpyrazin-2-yl)-1H-pyrazol-5-yl]amino}-3-oxopropanoate. MS (APCI): m/z 360 (M+H).

(i)

The preparation was performed in a similar manner as Example 1.006 (d) from ethyl 3-{[3-(6-isobutyl-3,5-dimethylpyrazin-2-yl)-1H-pyrazol-5-yl]amino}-3-oxopropanoate (1.12 g, 3.12 mmol) to give 2-(6-isobutyl-3,5-dimethylpyrazin-2-yl)pyrazolo[1,5-a]pyrimidine-5,7-diol. MS (APCI): m/z 314 (M+H).

(j)

The preparation was performed in a similar manner as Example 1.001 (f) from 2-(6-isobutyl-3,5-dimethylpyrazin-2-yl)pyrazolo[1,5-a]pyrimidine-5,7-diol (845 mg, 2.70 mmol) to give 5,7-dichloro-2-(6-isobutyl-3,5-dimethylpyrazin-2-yl)pyrazolo[1,5-a]pyrimidine (the compound of Reference Example 1.14 listed in the Table of Reference Examples as described hereinafter).

Reference Example 1.15

(a)

The preparation was performed in a similar manner as Reference Example 1.13 (d) from ethyl 6-chloro-3-methylpyrazine-2-carboxylate (Reference Example 1.13 (c)) (1.50 g, 7.48 mmol) and n-propylboronic acid (1.32 g, 15.0 mmol) to give ethyl 3-methyl-6-propylpyrazine-2-carboxylate. MS (APCI): m/z 209 (M+H).

(b)

The preparation was performed in a similar manner as Example 1.006 (a) method A from ethyl 3-methyl-6-propylpyrazine-2-carboxylate (1.09 g, 5.23 mmol) to give 3-(3-methyl-6-propylpyrazin-2-yl)-3-oxopropanenitrile. MS (APCI): m/z 204 (M+H).

(c)

The preparation was performed in a similar manner as Example 1.001 (c) from 3-(3-methyl-6-propylpyrazin-2-yl)-3-oxopropanenitrile (1.07 g, 5.23 mmol) to give 3-(3-methyl-6-propylpyrazin-2-yl)-1H-pyrazol-5-amine. MS (APCI): m/z 218 (M+H).

(d)

The preparation was performed in a similar manner as Example 1.006 (c) Method A from 3-(3-methyl-6-propylpyrazin-2-yl)-1H-pyrazol-5-amine (1.15 g, 5.29 mmol) to give ethyl 3-{[3-(3-methyl-6-propylpyrazin-2-yl)-1H-pyrazol-5-yl]amino}-3-oxopropanoate. MS (APCI): m/z 332 (M+H).

(e)

The preparation was performed in a similar manner as Reference Example 1.13 (h) from ethyl 3-{[3-(3-methyl-6-propylpyrazin-2-yl)-1H-pyrazol-5-yl]amino}-3-oxopropanoate (1.07 g, 3.23 mmol) to give 2-(3-methyl-6-propylpyrazin-2-yl)pyrazolo[1,5-a]pyrimidine-5,7-diol. MS (APCI): m/z 286 (M+H).

(f)

The preparation was performed in a similar manner as Example 1.001 (f) from 2-(3-methyl-6-propylpyrazin-2-yl)pyrazolo[1,5-a]pyrimidine-5,7-diol (803 mg, 2.81 mmol) to give 5,7-dichloro-2-(3-methyl-6-propylpyrazin-2-yl)pyrazolo[1,5-a]pyrimidine (the compound of Reference Example 1.15 listed in the Table of Reference Examples as described hereinafter).

Reference Example 1.16

(a)

The preparation was performed in a similar manner as Reference Example 1.13 (d) from methyl 6-chloro-3,5-dimethylpyrazine-2-carboxylate (which is described in Reference Example 1.14 (d)) (2.30 g, 10.7 mmol) and cyclopropylboronic acid (1.84 g, 21.4 mmol) to give ethyl 6-cyclopropyl-3,5-dimethylpyrazine-2-carboxylate. MS (APCI): m/z 221 (M+H).

(b)

The preparation was performed in a similar manner as Example 1.006 (a) method A from ethyl 6-cyclopropyl-3,5-dimethylpyrazine-2-carboxylate (2.30 g, 10.4 mmol) to give 3-(6-cyclopropyl-3,5-dimethylpyrazin-2-yl)-3-oxopropanenitrile. MS (APCI): m/z 216 (M+H).

(c)

First, the preparation was performed in a similar manner as Example 1.001 (c) from 3-(6-cyclopropyl-3,5-dimethylpyrazin-2-yl)-3-oxopropanenitrile (872 mg, 4.05 mmol) to give crude compound (839 mg, 90%). Next, the preparation was performed in a similar manner as Example 1.006 (c) Method A from crude compound (839 mg) to give ethyl 3-{[3-(6-cyclopropyl-3,5-dimethylpyrazin-2-yl)-1H-pyrazol-5-yl]amino}-3-oxopropanoate. MS (APCI): m/z 344 (M+H).

(d)

The preparation was performed in a similar manner as Reference Example 1.13 (h) from ethyl 3-{[3-(6-cyclopropyl-3,5-dimethylpyrazin-2-yl)-1H-pyrazol-5-yl]amino}-3-oxopropanoate (990 mg, 2.88 mmol) to give 2-(6-cyclopropyl-3,5-dimethylpyrazin-2-yl)pyrazolo[1,5-a]pyrimidine-5,7-diol. MS (APCI): m/z 298 (M+H).

(e)

The preparation was performed in a similar manner as Example 1.001 (f) from 2-(6-cyclopropyl-3,5-dimethylpyrazin-2-yl)pyrazolo[1,5-a]pyrimidine-5,7-diol (772 mg, 2.60 mmol) to give 5,7-dichloro-2-(6-cyclopropyl-3,5-dimethylpyrazin-2-yl)pyrazolo[1,5-a]pyrimidine (the compound of Reference Example 1.16 listed in the Table of Reference Examples as described hereinafter).

Reference Example 1.17

(a)

The preparation was performed in a similar manner as Example 1.001 (d) Method B from N-(tert-butoxycarbonyl)-L-norvaline (13.0 g, 59.8 mmol) and L-threonine ethyl ester hydrochloride (9.23 g, 54.4 mmol) to give methyl N-(tert-butoxycarbonyl)-L-norvalyl-L-threoninate. MS (APCI): m/z 333 (M+H).

(b)

The preparation was performed in a similar manner as Reference Example 1.14 (b) from methyl N-(tert-butoxycarbonyl)-L-norvalyl-L-threoninate (15.8 g, 47.5 mmol) to give methyl (2S)-2-{[N-(tert-butoxycarbonyl)-L-norvalyl]amino}-3-oxobutanoate. MS (APCI): m/z 348 (M+H).

(c)

The preparation was performed in a similar manner as Example 1.172 (b) from methyl (2S)-2-{[N-(tert-butoxycarbonyl)-L-norvalyl]amino}-3-oxobutanoate (10.3 g, 31.2 mmol) to give methyl 6-hydroxy-3-methyl-5-propylpyrazine-2-carboxylate. MS (APCI): m/z 211 (M+H).

(d)

The preparation was performed in a similar manner as Reference Example 1.07 (b) from methyl 6-hydroxy-3-methyl-5-propylpyrazine-2-carboxylate (3.49 g, 16.6 mmol) to give methyl 6-chloro-3-methyl-5-propylpyrazine-2-carboxylate. MS (APCI): m/z 229/231 (M+H).

(e)

To a solution of methyl 6-chloro-3-methyl-5-propylpyrazine-2-carboxylate (3.00 g, 13.1 mmol) and triethylamine (1.83 mL, 13.1 mmol) in tetrahydrofuran (40 mL) was added palladium on carbon (5%, M, wet, 300 mg) at 0° C. under argon. The reaction mixture was stirred for 8 h under hydrogen atmosphere, and then filtrated through celite with tetrahydrofuran. To the filtrate was added manganes dioxide (1.0 g) at room temperature. After being stirred overnight, the reaction mixture was filtrated through celite with tetrahydrofuran. The filtrate was concentrated in vacuo, and the residue was poured into saturated aqueous sodium bicarbonate. The mixture was extracted with ethyl acetate. The organic layer was washed with saturated brine, dried over sodium sulfate, filtrated and concentrated in vacuo. The residue was purified by silica gel column chromatography (hexane:ethyl acetate=4:1 to 13:7) to give methyl 3-methyl-5-propylpyrazine-2-carboxylate. MS (APCI): m/z 195 (M+H).

(f)

The preparation was performed in a similar manner as Example 1.006 (a) method A from methyl 3-methyl-5-propylpyrazine-2-carboxylate (1.77 g, 9.11 mmol) to give 3-(3-methyl-5-propylpyrazin-2-yl)-3-oxopropanenitrile. MS (APCI): m/z 204 (M+H).

(g)

First, the preparation was performed in a similar manner as Example 1.001 (c) from 3-(3-methyl-5-propylpyrazin-2-yl)-3-oxopropanenitrile (2.00 mg, 9.84 mmol) to give 3-(3-methyl-5-propylpyrazin-2-yl)-1H-pyrazol-5-amine. MS (APCI): m/z 218 (M+H).

(h)

First, the preparation was performed in a similar manner as Example 1.006 (c) Method A from 3-(3-methyl-5-propylpyrazin-2-yl)-1H-pyrazol-5-amine (1.37 g, 6.31 mmol) to crude compound (2.19 g). MS (APCI): m/z 344 (M+H). Second, the preparation was performed in a similar manner as Reference Example 1.13 (h) from ethyl 3-{[3-(3-methyl-5-propylpyrazin-2-yl)-1H-pyrazol-5-yl]amino}-3-oxopropanoate (2.19 g) to give crude compound (1.04 g). MS (APCI): m/z 286 (M+H). Third, the preparation was performed in a similar manner as Example 1.001 (f) from crude compound (1.04 g) to give 5,7-dichloro-2-(3-methyl-5-propylpyrazin-2-yl)pyrazolo[1,5-a]pyrimidine (the compound of Reference Example 1.17 listed in the Table of Reference Examples as described hereinafter).

Reference Example 1.18

(a)

A solution of 3-aminopyrazole (5.00 g, 60.2 mmol) and ethyl oxalpropionate (24.3 g, 120 mmol) in ethanol (602 mL) was refluxed for 24 h. After being cooled to ambient temperature, the reaction mixture was concentrated in vacuo. The residue was triturated with chloroform and diisopropyl ether to give the crude compound (10.4 g, 78%).

A solution of the crude compound (7.38 g, 33.4 mmol) and phosphorous oxychloride (62.3 g, 668 mmol) in toluene (67 mL) was refluxed for 3 h. After being cooled to ambient temperature, the reaction mixture was concentrated in vacuo. The residue was dissolved to chloroform and poured into 10% aqueous potassium carbonate. The organic layer was separated, and the aqueous layer was extracted with chloroform. The organic layer was combined, washed with water and saturated brine, dried over sodium sulfate, filtrated and concentrated in vacuo. The residue was purified by silica gel column chromatography (hexane:ethyl acetate=9:1 to 7:3) to give crude compound (7.07 g, 88%).

A suspension of the crude compound (4.49 g, 18.7 mmol), palladium on carbon (5%, M, wet, 2.25 g), and triethylamine (2.61 mL, 18.7 mmol) in tetrahydrofuran (190 mL) was stirred at room temperature for 40 min under hydrogen atmosphere. The reaction mixture was filtrated, and the filtrate was concentrated in vacuo. The residue was purified by silica gel column chromatography (hexane:ethyl acetate=4:1 to 2:3) to give ethyl 6-methylpyrazolo[1,5-a]pyrimidine-5-carboxylate. MS (APCI): m/z 206 (M+H).

(b)

The preparation was performed in a similar manner as Example 1.006 (a) method A from ethyl 6-methylpyrazolo[1,5-a]pyrimidine-5-carboxylate (3.42 g, 16.7 mmol) to give 3-(6-methylpyrazolo[1,5-a]pyrimidin-5-yl)-3-oxopropionitrile. MS (APCI): m/z 201 (M+H).

(c)

First, the preparation was performed in a similar manner as Example 1.001 (c) from 3-(6-methylpyrazolo[1,5-a]pyrimidin-5-yl)-3-oxopropionitrile (2.45 g, 12.2 mmol) to give 3-(6-methylpyrazolo[1.5-a]pyrimidin-5-yl)-1H-pyrazol-5-amine. MS (APCI): m/z 215 (M+H).

(d)

The preparation was performed in a similar manner as Example 1.006 (c) Method A from 3-(6-methylpyrazolo[1.5-a]pyrimidin-5-yl)-1H-pyrazol-5-amine (2.30 g, 10.7 mmol) to give ethyl 3-{[3-(6-methylpyrazolo[1,5-a]pyrimidin-5-yl)-1H-pyrazol-5-yl]amino}-3-oxopropanoate. MS (APCI): m/z 329 (M+H).

(e)

The preparation was performed in a similar manner as Example 1.006 (d) from ethyl 3-{[3-(6-methylpyrazolo[1,5-a]pyrimidin-5-yl)-1H-pyrazol-5-yl]amino}-3-oxopropanoate (3.20 g, 9.75 mmol) to give 6'-methyl-2,5'-bipyrazolo[1,5-a]pyrimidine-5,7-diol. MS (APCI): m/z 283 (M+H).

(f)

The preparation was performed in a similar manner as Example 1.001 (f) from 6'-methyl-2,5'-bipyrazolo[1,5-a]pyrimidine-5,7-diol (2.86 g, 9.75 mmol) to give 5,7-dichloro-6'-methyl-2,5'-bipyrazolo[1,5-a]pyrimidine (the compound of Reference Example 1.18 listed in the Table of Reference Examples as described hereinafter).

The following abbreviations are utilized in the specification:

"MS (APCI)" means mass spectrometry (Atmospheric Pressure Chemical Ionization mass spectrometry), "MS (ESI)" means mass spectrometry (Electro Spray Ionization mass spectrometry), "Me" means methyl group;

"Et" means ethyl group;

"Pr" means propyl group;

"Bu" means butyl group; and

"Boc" means tert-butoxycarbonyl group.

The structural formula and physical properties, etc. of the compounds of the Examples and the Reference Examples are shown in the following Tables of Examples and Tables of Reference Examples.

TABLE OF EXAMPLES

| Example | Structure | Salt | MS (APCI) |
|---|---|---|---|
| 1.001 | 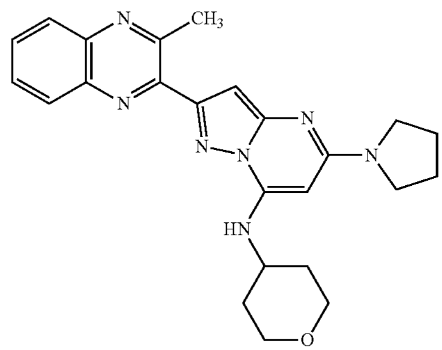 [SMILES: Cc1nc2ccccc2nc1-c1cc2nc(N3CCCC3)cc(NC3CCOCC3)n2n1] | HCl 2 HCl | 430 (M + H) |
| 1.002 | 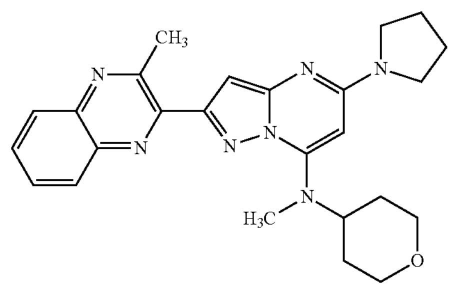 [SMILES: Cc1nc2ccccc2nc1-c1cc2nc(N3CCCC3)cc(N(C)C3CCOCC3)n2n1] | HCl 3/2 HCl | 444 (M + H) |
| 1.003 | 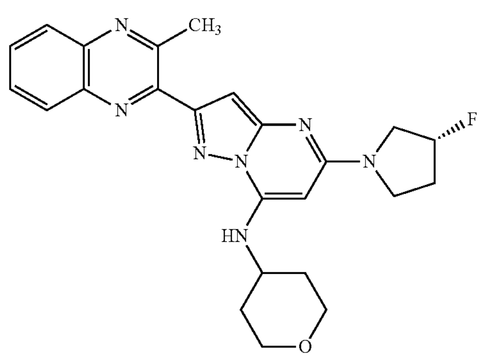 [SMILES: Cc1nc2ccccc2nc1-c1cc2nc(N3CC[C@@H](F)C3)cc(NC3CCOCC3)n2n1] | HCl 2 HCl | 448 (M + H) |
| 1.004 | 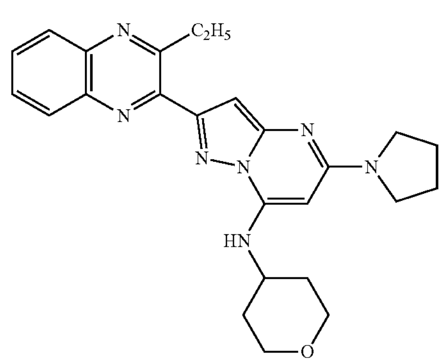 [SMILES: CCc1nc2ccccc2nc1-c1cc2nc(N3CCCC3)cc(NC3CCOCC3)n2n1] | 2 HCl | 444 (M + H) |

TABLE OF EXAMPLES-continued

| Example | Structure | Salt | MS (APCI) |
|---|---|---|---|
| 1.005 | 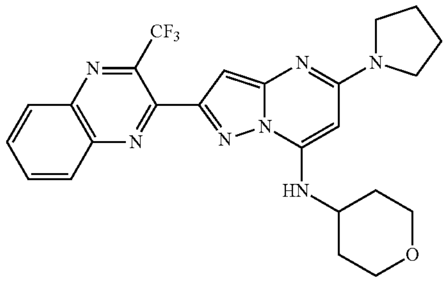 [SMILES: FC(F)(F)c1nc2ccccc2nc1-c1cc2nc(N3CCCC3)cc(NC3CCOCC3)n2n1] | HCl | 484 (M + H) |
| 1.006 | 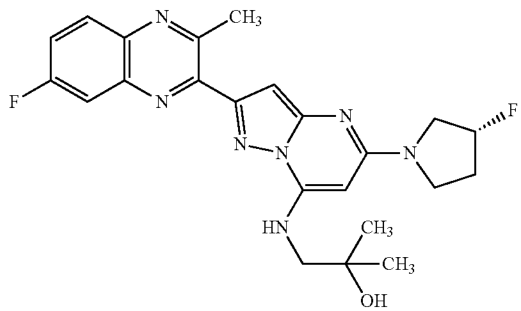 [SMILES: Cc1nc2ccc(F)cc2nc1-c1cc2nc(N3CC[C@@H](F)C3)cc(NCC(C)(C)O)n2n1] | HCl | 454 (M + H) |
| 1.007 | 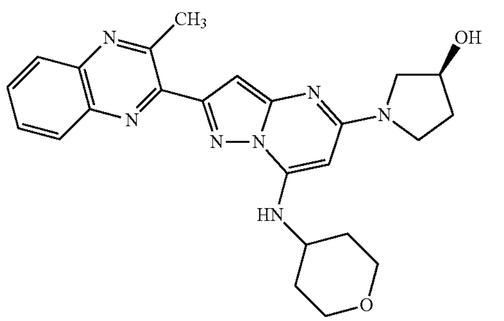 [SMILES: Cc1nc2ccccc2nc1-c1cc2nc(N3CC[C@H](O)C3)cc(NC3CCOCC3)n2n1] | Free form | 446 (M + H) |
| 1.008 | 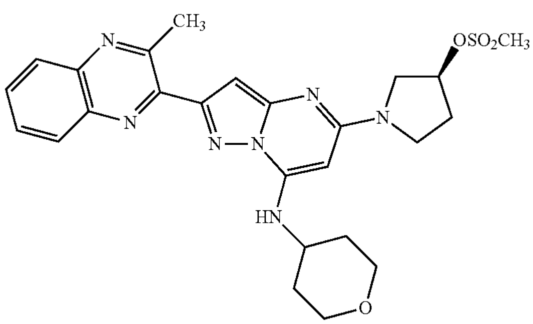 | Free form | 524 (M + H) |
| 1.009 | 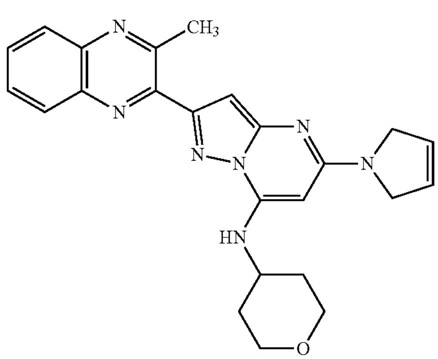 [SMILES: Cc1nc2ccccc2nc1-c1cc2nc(N3CC=CC3)cc(NC3CCOCC3)n2n1] | Free form | 428 (M + H) |

TABLE OF EXAMPLES-continued

| Example | Structure | Salt | MS (APCI) |
|---|---|---|---|
| 1.010 | 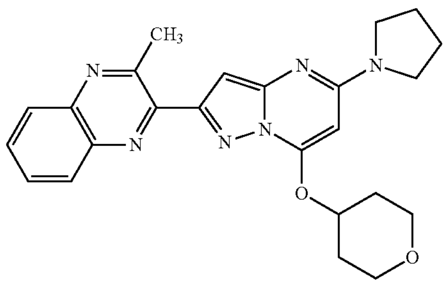 | HCl 2 HCl | 431 (M + H) |
| 1.011 | 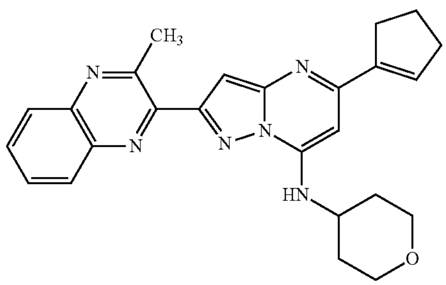 [SMILES: Cc1nc2ccccc2nc1-c1cc2nc(C3=CCCC3)cc(NC3CCOCC3)n2n1] | Free form | 427 (M + H) |
| 1.012 | 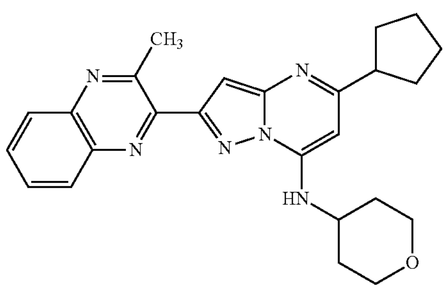 [SMILES: Cc1nc2ccccc2nc1-c1cc2nc(C3CCCC3)cc(NC3CCOCC3)n2n1] | Free form | 429 (M + H) |
| 1.013 | 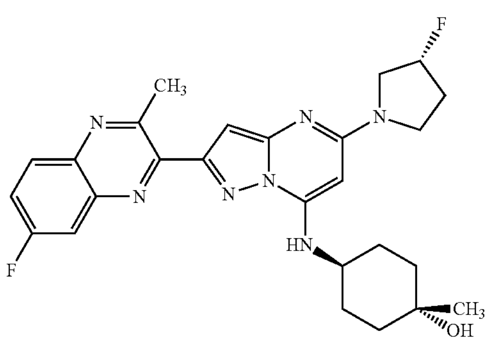 [SMILES: Cc1nc2ccc(F)cc2nc1-c1cc2nc(N3CC[C@@H](F)C3)cc(N[C@H]3CC[C@](C)(O)CC3)n2n1] | HCl | 494 (M + H) |
| 1.014 | 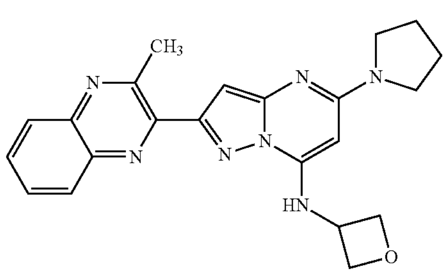 [SMILES: Cc1nc2ccccc2nc1-c1cc2nc(N3CCCC3)cc(NC3COC3)n2n1] | Free form | 402 (M + H) |

TABLE OF EXAMPLES-continued
| Example | Structure | Salt | MS (APCI) |
|---|---|---|---|
| 1.015 | 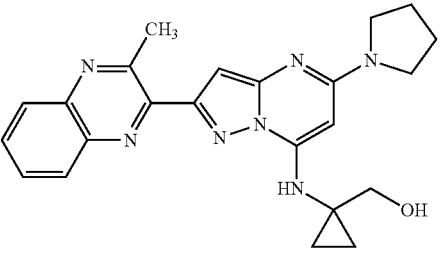 [SMILES: Cc1nc2ccccc2nc1-c1cc2nc(N3CCCC3)cc(NC3(CO)CC3)n2n1] | HCl | 416 (M + H) |
| 1.016 | 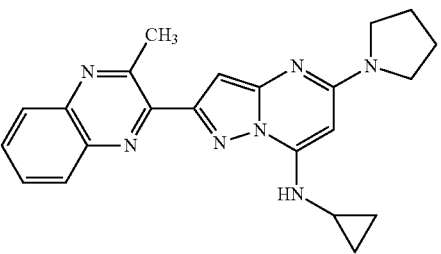 [SMILES: Cc1nc2ccccc2nc1-c1cc2nc(N3CCCC3)cc(NC3CC3)n2n1] | HCl | 386 (M + H) |
| 1.017 | 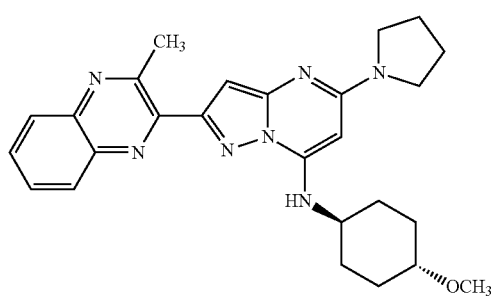 [SMILES: CO[C@H]1CC[C@H](Nc2cc(N3CCCC3)nc3cc(-c4nc5ccccc5nc4C)nn23)CC1] | HCl<br>3/2 HCl | 458 (M + H) |
| 1.018 | 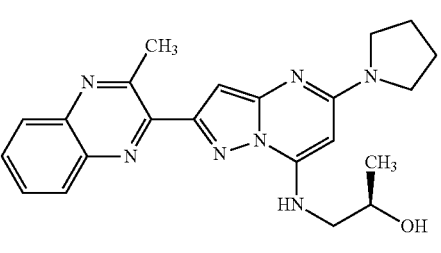 [SMILES: Cc1nc2ccccc2nc1-c1cc2nc(N3CCCC3)cc(NC[C@@H](C)O)n2n1] | HCl | 404 (M + H) |
| 1.019 | 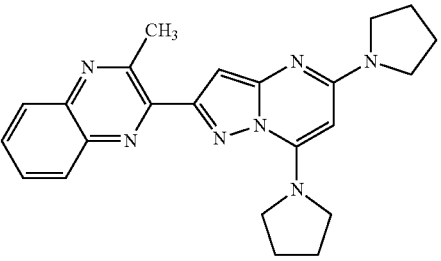 [SMILES: Cc1nc2ccccc2nc1-c1cc2nc(N3CCCC3)cc(N3CCCC3)n2n1] | 2 HCl | 400 (M + H) |
| 1.020 | 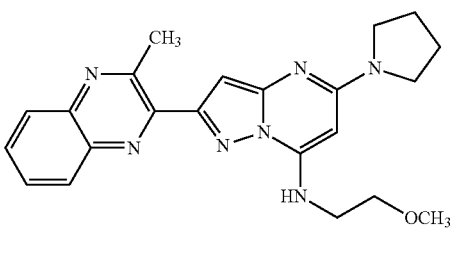 [SMILES: COCCNc1cc(N2CCCC2)nc2cc(-c3nc4ccccc4nc3C)nn12] | 2 HCl | 404 (M + H) |

TABLE OF EXAMPLES-continued

| Example | Structure | Salt | MS (APCI) |
|---|---|---|---|
| 1.021 | 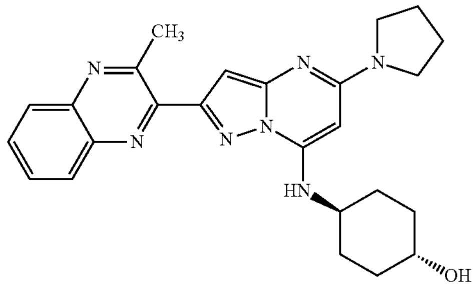 [SMILES: Cc1nc2ccccc2nc1-c1cc2nc(N3CCCC3)cc(N[C@H]3CC[C@H](O)CC3)n2n1] | HCl 2 HCl | 444 (M + H) |
| 1.022 | 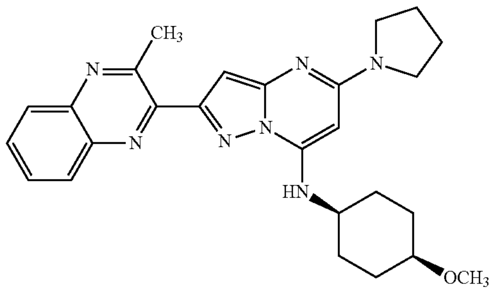 [SMILES: CO[C@H]1CC[C@@H](Nc2cc(N3CCCC3)nc3cc(-c4nc5ccccc5nc4C)nn23)CC1] | HCl 3/2 HCl | 458 (M + H) |
| 1.023 | 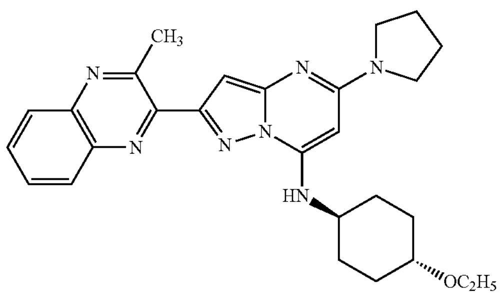 [SMILES: CCO[C@H]1CC[C@H](Nc2cc(N3CCCC3)nc3cc(-c4nc5ccccc5nc4C)nn23)CC1] | HCl 3/2 HCl | 472 (M + H) |
| 1.024 | 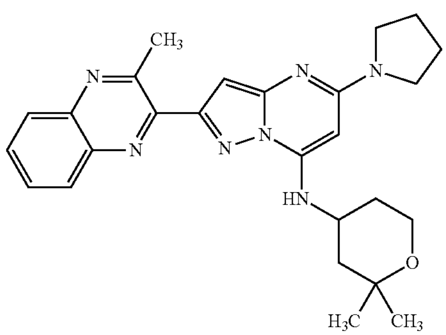 [SMILES: Cc1nc2ccccc2nc1-c1cc2nc(N3CCCC3)cc(NC3CCOC(C)(C)C3)n2n1] | 3/2 HCl | 458 (M + H) |
| 1.025 | 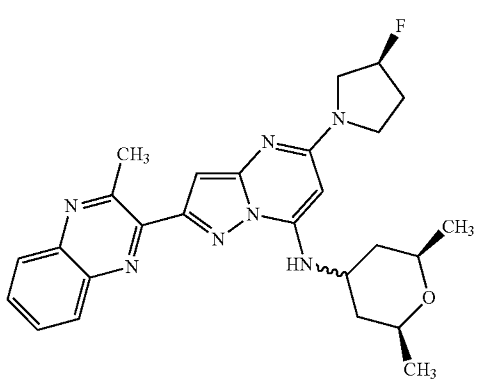 [SMILES: Cc1nc2ccccc2nc1-c1cc2nc(N3CC[C@H](F)C3)cc(NC3C[C@@H](C)O[C@@H](C)C3)n2n1] | 3/2 HCl | 476 (M + H) |

TABLE OF EXAMPLES-continued
| Example | Structure | Salt | MS (APCI) |
|---|---|---|---|
| 1.026 | 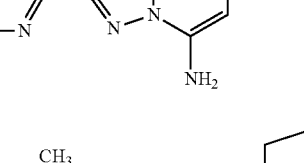 | Free form | 346 (M + H) |
| 1.027 | 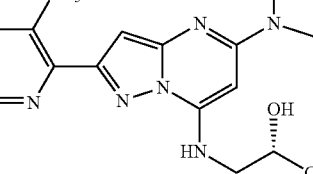 | HCl | 458 (M + H) |
| 1.028 | 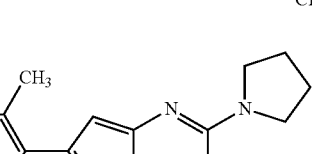 | HCl<br>2 HCl | 458 (M + H) |
| 1.029 | 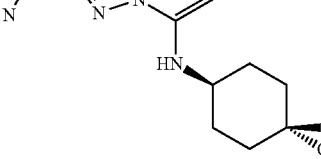 | 3/2 HCl | 430 (M + H) |
| 1.030 | 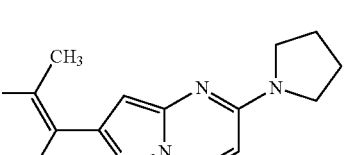 | HCl | 418 (M + H) |
| 1.031 | 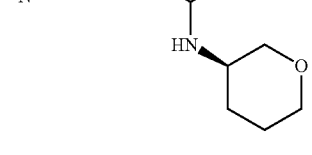 | HCl | 399 (M + H) |

TABLE OF EXAMPLES-continued

| Example | Structure | Salt | MS (APCI) |
|---|---|---|---|
| 1.032 | 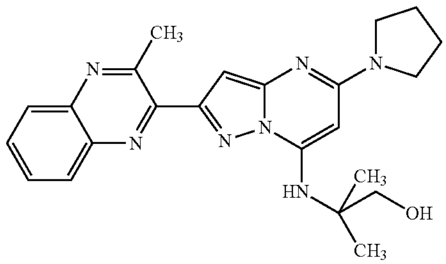 [SMILES: Cc1nc2ccccc2nc1-c1cc2nc(N3CCCC3)cc(NC(C)(C)CO)n2n1] | HCl | 418 (M + H) |
| 1.033 | 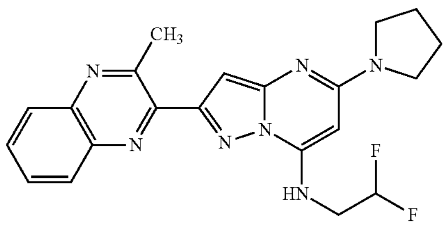 [SMILES: Cc1nc2ccccc2nc1-c1cc2nc(N3CCCC3)cc(NCC(F)F)n2n1] | HCl | 410 (M + H) |
| 1.034 | 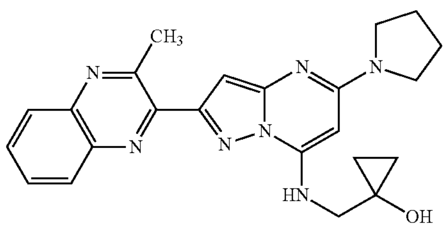 [SMILES: Cc1nc2ccccc2nc1-c1cc2nc(N3CCCC3)cc(NCC3(O)CC3)n2n1] | HCl | 416 (M + H) |
| 1.035 | 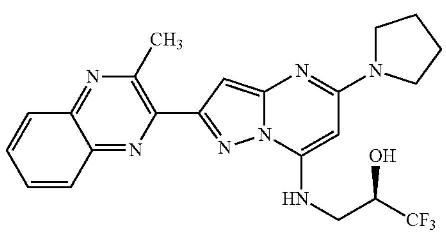 [SMILES: Cc1nc2ccccc2nc1-c1cc2nc(N3CCCC3)cc(NC[C@@H](O)C(F)(F)F)n2n1] | HCl | 458 (M + H) |
| 1.036 | 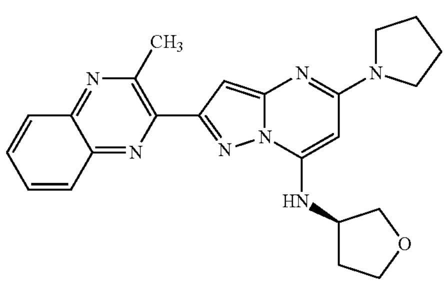 [SMILES: Cc1nc2ccccc2nc1-c1cc2nc(N3CCCC3)cc(N[C@@H]3CCOC3)n2n1] | HCl | 416 (M + H) |
| 1.037 | 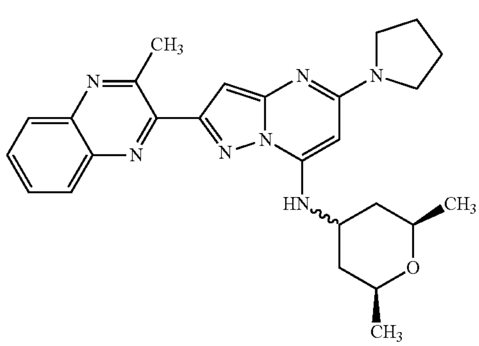 [SMILES: Cc1nc2ccccc2nc1-c1cc2nc(N3CCCC3)cc(NC3C[C@@H](C)O[C@@H](C)C3)n2n1] | 2 HCl | 458 (M + H) |

TABLE OF EXAMPLES-continued

| Example | Structure | Salt | MS (APCI) |
|---|---|---|---|
| 1.038 | 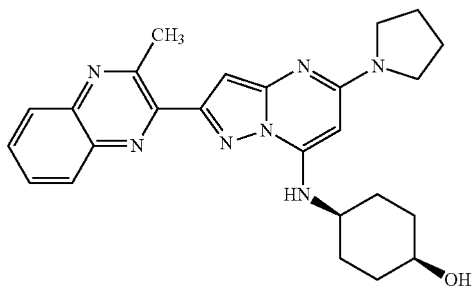 [SMILES: Cc1nc2ccccc2nc1-c1cc2nc(N3CCCC3)cc(N[C@H]3CC[C@@H](O)CC3)n2n1] | HCl 2 HCl | 444 (M + H) |
| 1.039 | 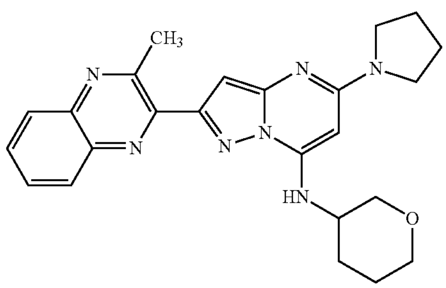 | 2 HCl | 430 (M + H) |
| 1.040 | 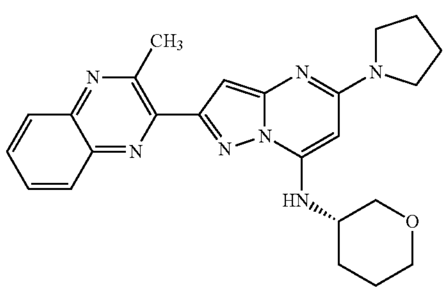 [SMILES: Cc1nc2ccccc2nc1-c1cc2nc(N3CCCC3)cc(N[C@H]3CCCOC3)n2n1] | 3/2 HCl | 430 (M + H) |
| 1.041 | 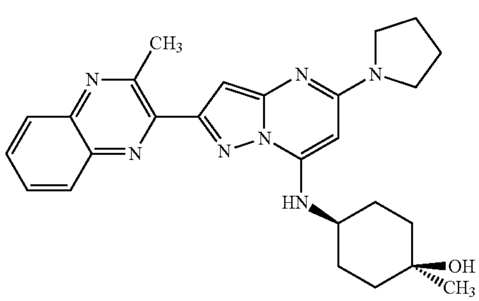 [SMILES: Cc1nc2ccccc2nc1-c1cc2nc(N3CCCC3)cc(N[C@H]3CC[C@@](C)(O)CC3)n2n1] | HCl | 458 (M + H) |
| 1.042 | 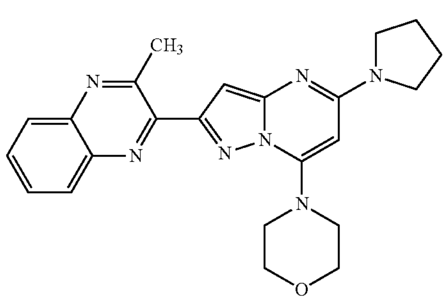 [SMILES: Cc1nc2ccccc2nc1-c1cc2nc(N3CCCC3)cc(N3CCOCC3)n2n1] | HCl | 416 (M + H) |

TABLE OF EXAMPLES-continued

| Example | Structure | Salt | MS (APCI) |
|---|---|---|---|
| 1.043 | 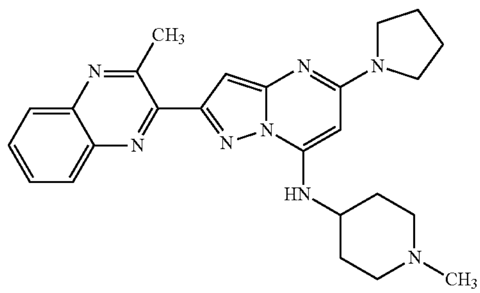 [SMILES: Cc1nc2ccccc2nc1-c1cc2nc(N3CCCC3)cc(NC3CCN(C)CC3)n2n1] | 5/2 HCl | 443 (M + H) |
| 1.044 | 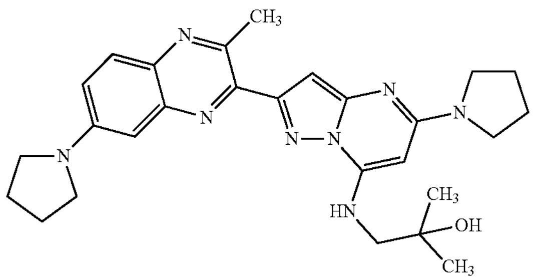 [SMILES: Cc1nc2ccc(N3CCCC3)cc2nc1-c1cc2nc(N3CCCC3)cc(NCC(C)(C)O)n2n1] | Free form | 487 (M + H) |
| 1.045 | 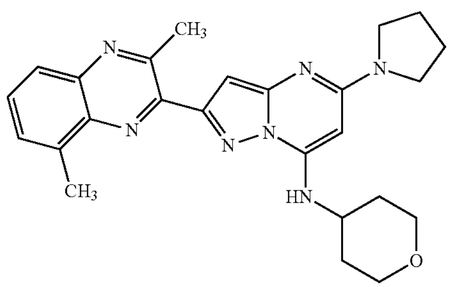 [SMILES: Cc1nc2cccc(C)c2nc1-c1cc2nc(N3CCCC3)cc(NC3CCOCC3)n2n1] | 5/2 HCl | 444 (M + H) |
| 1.046 | 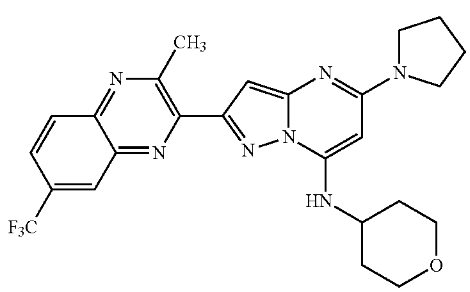 [SMILES: Cc1nc2ccc(C(F)(F)F)cc2nc1-c1cc2nc(N3CCCC3)cc(NC3CCOCC3)n2n1] | HCl | 498 (M + H) |
| 1.047 | 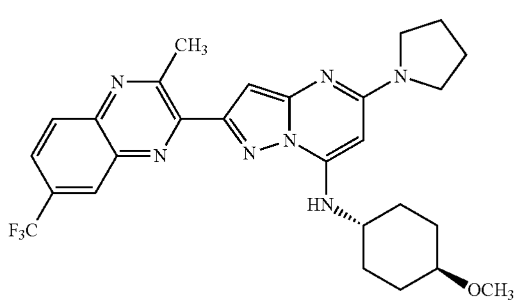 [SMILES: CO[C@H]1CC[C@H](Nc2cc(N3CCCC3)nc3cc(-c4nc5cc(C(F)(F)F)ccc5nc4C)nn23)CC1] | 5/4 HCl | 526 (M + H) |

TABLE OF EXAMPLES-continued

| Example | Structure | Salt | MS (APCI) |
|---------|-----------|------|-----------|
| 1.048 | 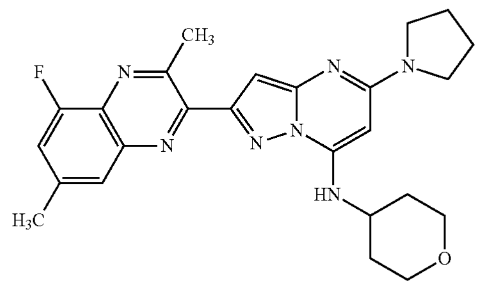 [SMILES: Cc1cc(F)c2nc(C)c(-c3cc4nc(N5CCCC5)cc(NC5CCOCC5)n4n3)nc2c1] | 2 HCl | 462 (M + H) |
| 1.049 | 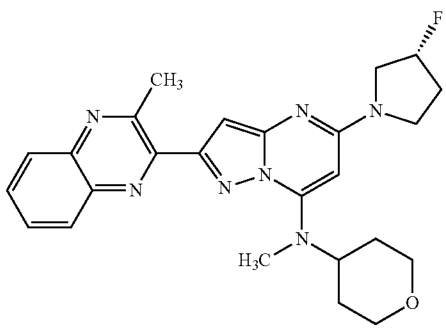 [SMILES: Cc1nc2ccccc2nc1-c1cc2nc(N3CC[C@@H](F)C3)cc(N(C)C3CCOCC3)n2n1] | HCl | 462 (M + H) |
| 1.050 | 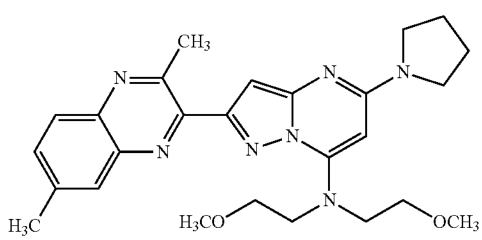 [SMILES: COCCN(CCOC)c1cc(N2CCCC2)nc2cc(-c3nc4cc(C)ccc4nc3C)nn12] | 2 HCl | 476 (M + H) |
| 1.051 | 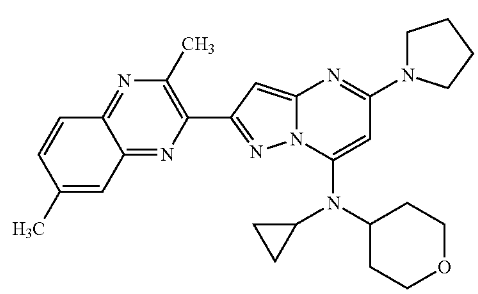 [SMILES: Cc1ccc2nc(C)c(-c3cc4nc(N5CCCC5)cc(N(C5CCOCC5)C5CC5)n4n3)nc2c1] | 2 HCl | 484 (M + H) |
| 1.052 | 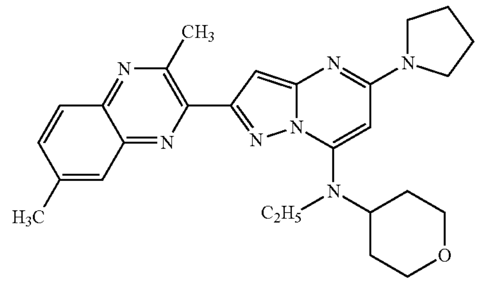 [SMILES: CCN(c1cc(N2CCCC2)nc2cc(-c3nc4cc(C)ccc4nc3C)nn12)C1CCOCC1] | 2 HCl | 472 (M + H) |

TABLE OF EXAMPLES-continued

| Example | Structure | Salt | MS (APCI) |
|---|---|---|---|
| 1.053 | 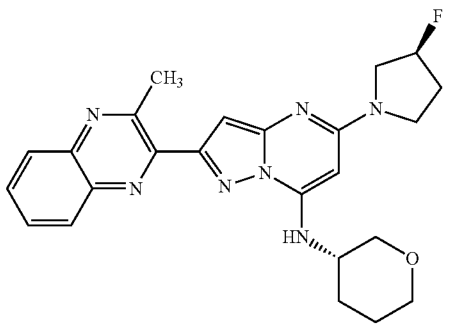 [SMILES: Cc1nc2ccccc2nc1-c1cc2nc(N3CC[C@H](F)C3)cc(N[C@H]3CCCOC3)n2n1] | HCl | 448 (M + H) |
| 1.054 | 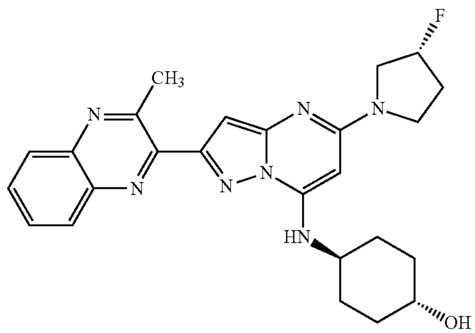 [SMILES: Cc1nc2ccccc2nc1-c1cc2nc(N3CC[C@@H](F)C3)cc(N[C@H]3CC[C@H](O)CC3)n2n1] | HCl | 462 (M + H) |
| 1.055 | 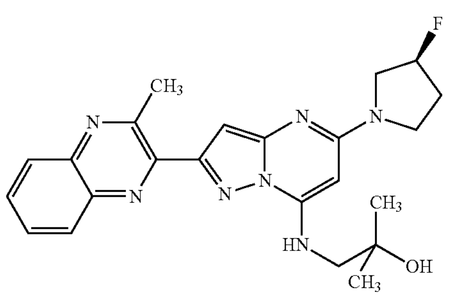 [SMILES: Cc1nc2ccccc2nc1-c1cc2nc(N3CC[C@H](F)C3)cc(NCC(C)(C)O)n2n1] | HCl | 436 (M + H) |
| 1.056 | 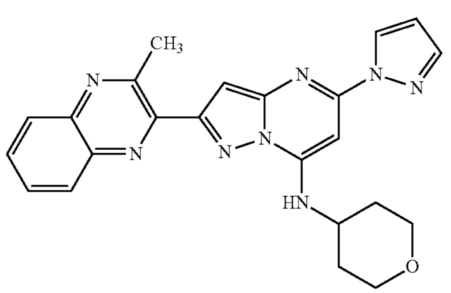 [SMILES: Cc1nc2ccccc2nc1-c1cc2nc(-n3cccn3)cc(NC3CCOCC3)n2n1] | Free form | 427 (M + H) |
| 1.057 | 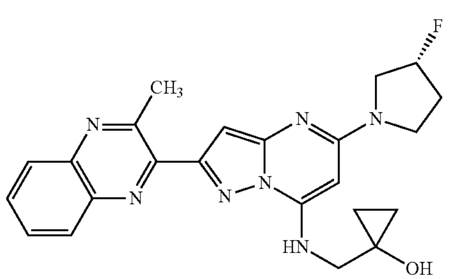 [SMILES: Cc1nc2ccccc2nc1-c1cc2nc(N3CC[C@@H](F)C3)cc(NCC3(O)CC3)n2n1] | HCl | 434 (M + H) |

TABLE OF EXAMPLES-continued

| Example | Structure | Salt | MS (APCI) |
|---|---|---|---|
| 1.058 | 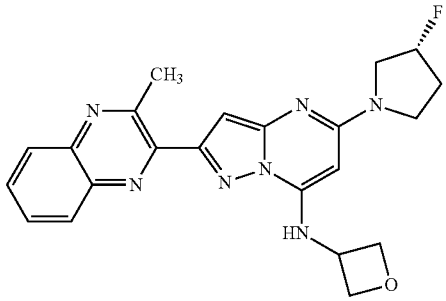 [SMILES: Cc1nc2ccccc2nc1-c1cc2nc(N3CC[C@@H](F)C3)cc(NC3COC3)n2n1] | Free form | 420 (M + H) |
| 1.059 | 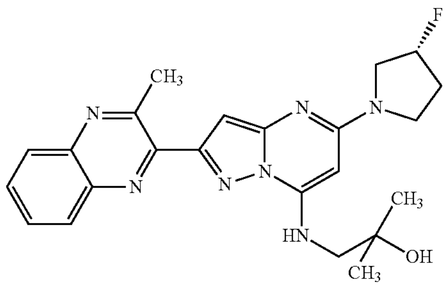 [SMILES: Cc1nc2ccccc2nc1-c1cc2nc(N3CC[C@@H](F)C3)cc(NCC(C)(C)O)n2n1] | HCl | 436 (M + H) |
| 1.060 | 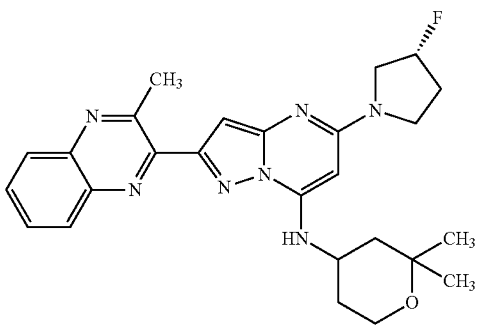 [SMILES: Cc1nc2ccccc2nc1-c1cc2nc(N3CC[C@@H](F)C3)cc(NC3CCOC(C)(C)C3)n2n1] | 3/2 HCl | 476 (M + H) |
| 1.061 | 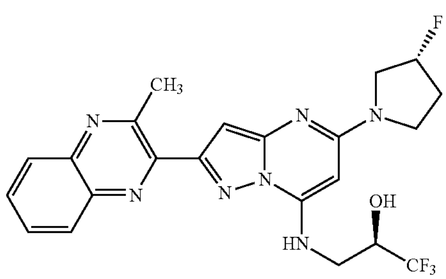 [SMILES: Cc1nc2ccccc2nc1-c1cc2nc(N3CC[C@@H](F)C3)cc(NC[C@@H](O)C(F)(F)F)n2n1] | 3/2 HCl | 476 (M + H) |
| 1.062 | 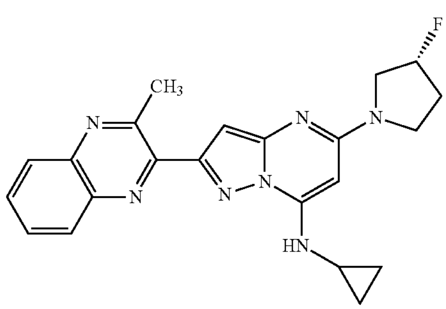 [SMILES: Cc1nc2ccccc2nc1-c1cc2nc(N3CC[C@@H](F)C3)cc(NC3CC3)n2n1] | HCl | 404 (M + H) |

TABLE OF EXAMPLES-continued

| Example | Structure | Salt | MS (APCI) |
|---|---|---|---|
| 1.063 | 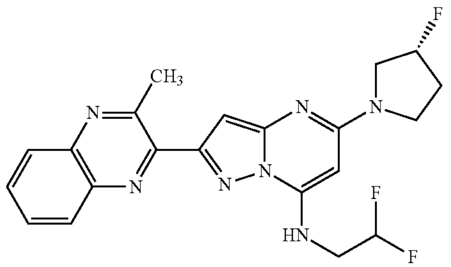 [SMILES: Cc1nc2ccccc2nc1-c1cc2nc(N3CC[C@@H](F)C3)cc(NCC(F)F)n2n1] | HCl | 428 (M + H) |
| 1.064 | 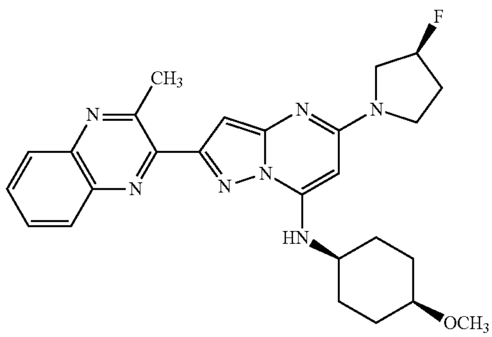 [SMILES: CO[C@H]1CC[C@@H](Nc2cc(N3CC[C@H](F)C3)nc3cc(-c4nc5ccccc5nc4C)nn23)CC1] | HCl | 476 (M + H) |
| 1.065 | 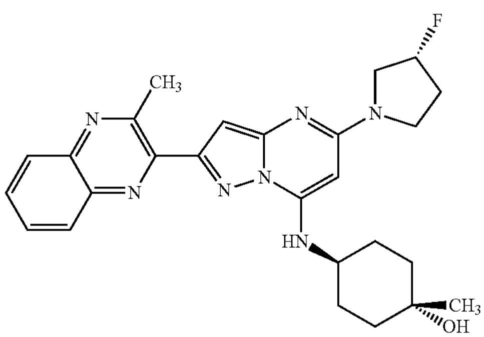 [SMILES: Cc1nc2ccccc2nc1-c1cc2nc(N3CC[C@@H](F)C3)cc(N[C@H]3CC[C@](C)(O)CC3)n2n1] | HCl | 476 (M + H) |
| 1.066 | 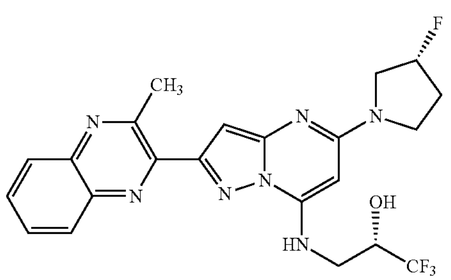 [SMILES: Cc1nc2ccccc2nc1-c1cc2nc(N3CC[C@@H](F)C3)cc(NC[C@H](O)C(F)(F)F)n2n1] | 2 HCl | 476 (M + H) |
| 1.067 | 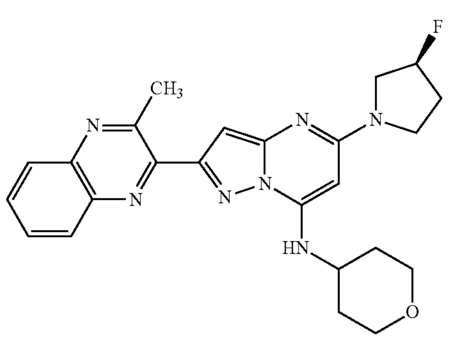 [SMILES: Cc1nc2ccccc2nc1-c1cc2nc(N3CC[C@H](F)C3)cc(NC3CCOCC3)n2n1] | HCl | 448 (M + H) |

TABLE OF EXAMPLES-continued

| Example | Structure | Salt | MS (APCI) |
|---|---|---|---|
| 1.068 | 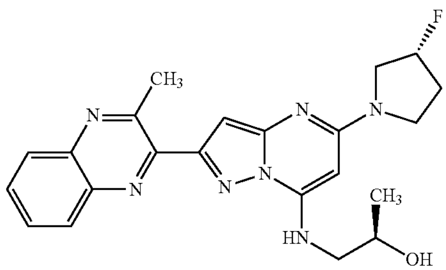 [SMILES: Cc1nc2ccccc2nc1-c1cc2nc(N3CC[C@@H](F)C3)cc(NC[C@@H](C)O)n2n1] | HCl | 422 (M + H) |
| 1.069 | 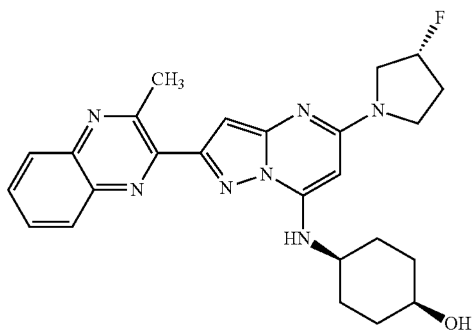 [SMILES: Cc1nc2ccccc2nc1-c1cc2nc(N3CC[C@@H](F)C3)cc(N[C@H]3CC[C@@H](O)CC3)n2n1] | HCl | 462 (M + H) |
| 1.070 | 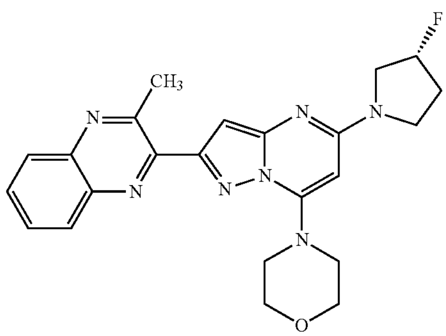 [SMILES: Cc1nc2ccccc2nc1-c1cc2nc(N3CC[C@@H](F)C3)cc(N3CCOCC3)n2n1] | HCl | 434 (M + H) |
| 1.071 | 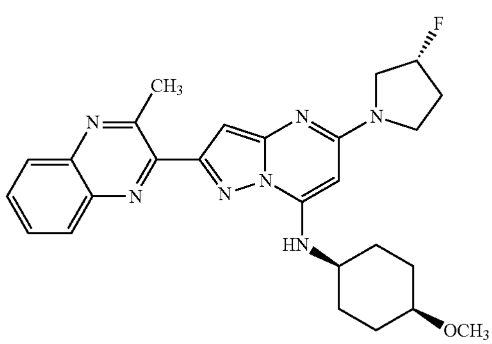 [SMILES: CO[C@H]1CC[C@@H](Nc2cc(N3CC[C@@H](F)C3)nc3cc(-c4nc5ccccc5nc4C)nn23)CC1] | 3/2 HCl | 476 (M + H) |
| 1.072 | 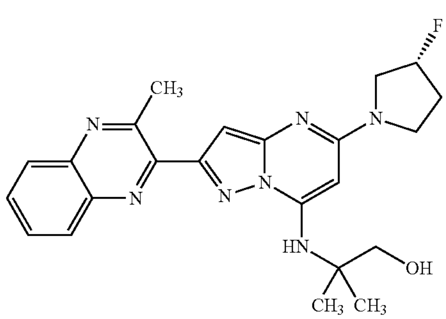 [SMILES: Cc1nc2ccccc2nc1-c1cc2nc(N3CC[C@@H](F)C3)cc(NC(C)(C)CO)n2n1] | HCl | 436 (M + H) |

TABLE OF EXAMPLES-continued

| Example | Structure | Salt | MS (APCI) |
|---------|-----------|------|-----------|
| 1.073 | 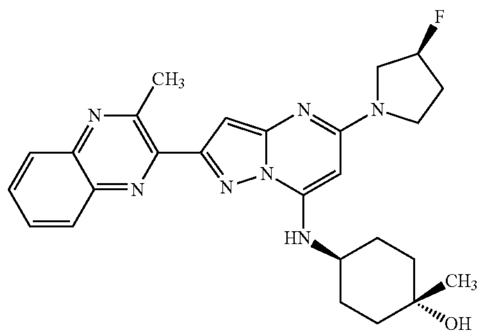 [SMILES: Cc1nc2ccccc2nc1-c1cc2nc(N3CC[C@H](F)C3)cc(N[C@H]3CC[C@](C)(O)CC3)n2n1] | HCl | 476 (M + H) |
| 1.074 | 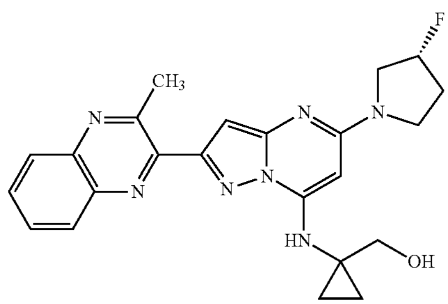 [SMILES: Cc1nc2ccccc2nc1-c1cc2nc(N3CC[C@@H](F)C3)cc(NC3(CO)CC3)n2n1] | HCl | 434 (M + H) |
| 1.075 | 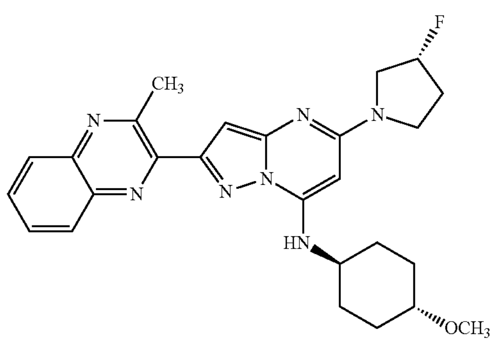 [SMILES: CO[C@H]1CC[C@H](Nc2cc(N3CC[C@@H](F)C3)nc3cc(-c4nc5ccccc5nc4C)nn23)CC1] | HCl 3/2 HCl | 476 (M + H) |
| 1.076 | 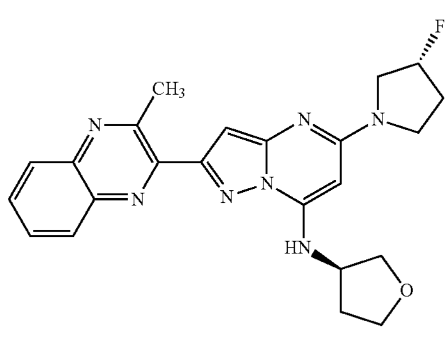 [SMILES: Cc1nc2ccccc2nc1-c1cc2nc(N3CC[C@@H](F)C3)cc(N[C@@H]3CCOC3)n2n1] | Free form | 434 (M + H) |

TABLE OF EXAMPLES-continued

| Example | Structure | Salt | MS (APCI) |
|---|---|---|---|
| 1.077 | 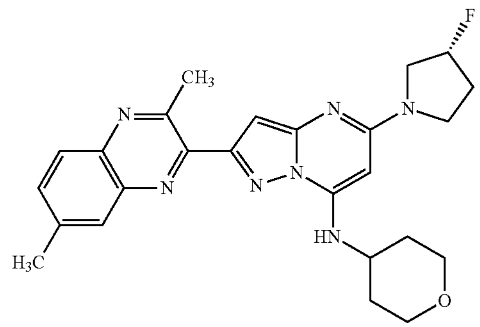 [SMILES: Cc1ccc2nc(C)c(-c3cc4nc(N5CC[C@@H](F)C5)cc(NC5CCOCC5)n4n3)nc2c1] | HCl 3/2 HCl | 462 (M + H) |
| 1.078 | 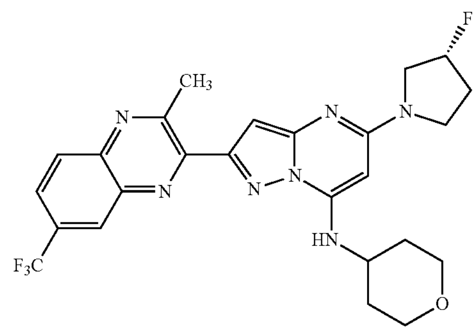 [SMILES: Cc1nc2ccc(C(F)(F)F)cc2nc1-c1cc2nc(N3CC[C@@H](F)C3)cc(NC3CCOCC3)n2n1] | 3/2 HCl | 516 (M + H) |
| 1.079 | 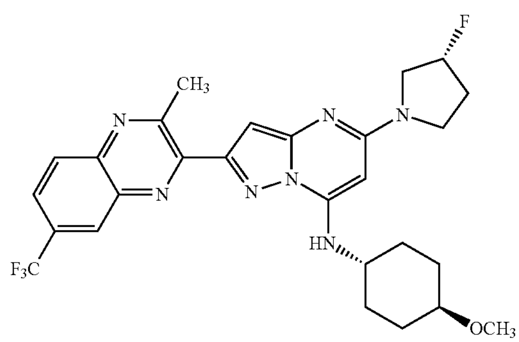 [SMILES: CO[C@H]1CC[C@H](Nc2cc(N3CC[C@@H](F)C3)nc3cc(-c4nc5cc(C(F)(F)F)ccc5nc4C)nn23)CC1] | HCl | 544 (M + H) |
| 1.080 | 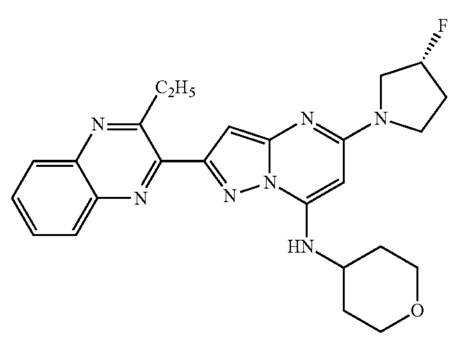 [SMILES: CCc1nc2ccccc2nc1-c1cc2nc(N3CC[C@@H](F)C3)cc(NC3CCOCC3)n2n1] | 2 HCl | 462 (M + H) |

TABLE OF EXAMPLES-continued
| Example | Structure | Salt | MS (APCI) |
|---|---|---|---|
| 1.081 | 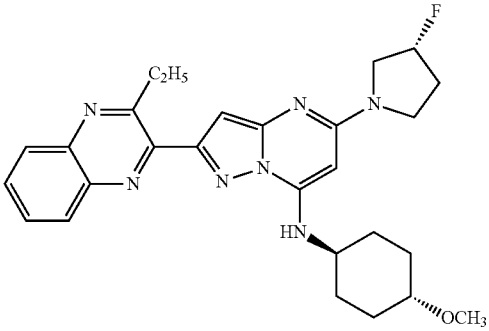 [SMILES: CCc1nc2ccccc2nc1-c1cc2nc(N3CC[C@@H](F)C3)cc(N[C@H]3CC[C@H](OC)CC3)n2n1] | 2 HCl | 490 (M + H) |
| 1.082 | 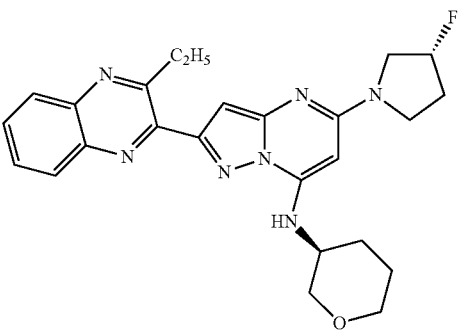 [SMILES: CCc1nc2ccccc2nc1-c1cc2nc(N3CC[C@@H](F)C3)cc(N[C@H]3CCCOC3)n2n1] | 3/2 HCl | 462 (M + H) |
| 1.083 | 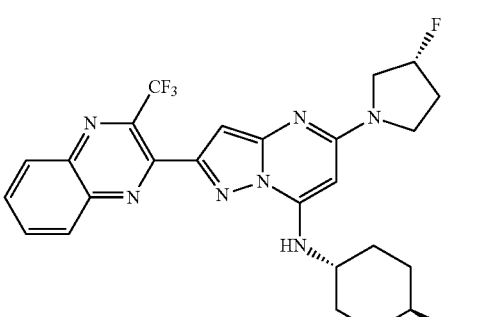 | HCl | 530 (M + H) |
| 1.084 | 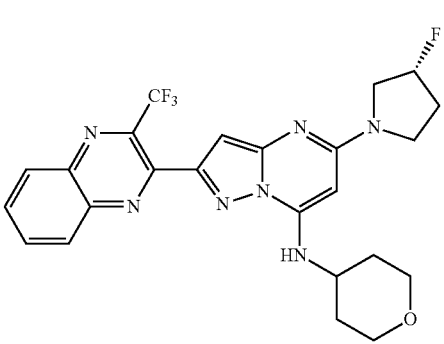 [SMILES: F[C@@H]1CCN(c2cc(NC3CCOCC3)n3nc(-c4nc5ccccc5nc4C(F)(F)F)cc3n2)C1] | HCl | 502 (M + H) |

TABLE OF EXAMPLES-continued

| Example | Structure | Salt | MS (APCI) |
|---|---|---|---|
| 1.085 | 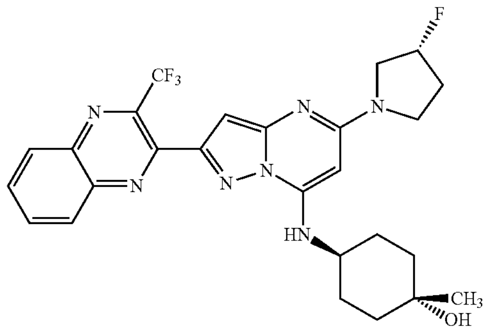 | HCl | 530 (M + H) |
| 1.086 | 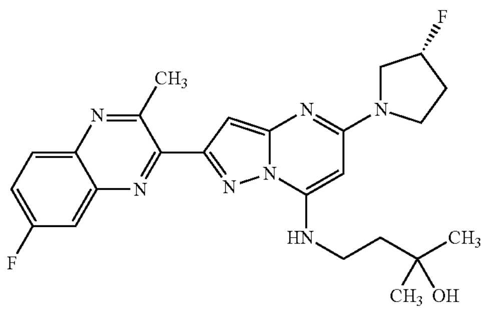 [SMILES: Cc1nc2ccc(F)cc2nc1-c1cc2nc(N3CC[C@@H](F)C3)cc(NCCC(C)(C)O)n2n1] | HCl | 468 (M + H) |
| 1.087 | 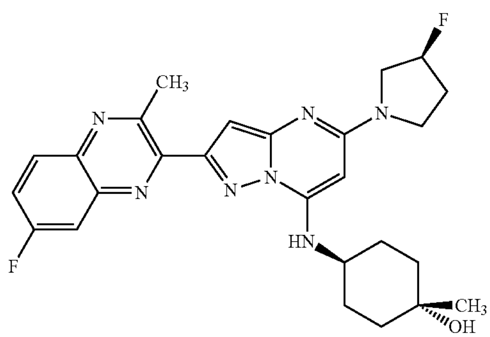 [SMILES: Cc1nc2ccc(F)cc2nc1-c1cc2nc(N3CC[C@H](F)C3)cc(N[C@H]3CC[C@](C)(O)CC3)n2n1] | HCl | 494 (M + H) |
| 1.088 | 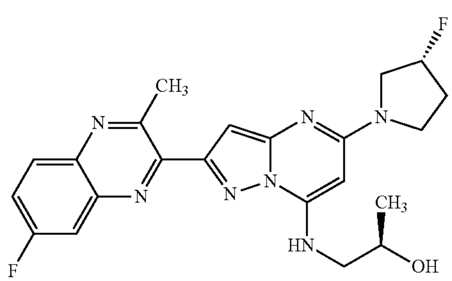 [SMILES: Cc1nc2ccc(F)cc2nc1-c1cc2nc(N3CC[C@@H](F)C3)cc(NC[C@@H](C)O)n2n1] | 9/10 HCl | 440 (M + H) |
| 1.089 | 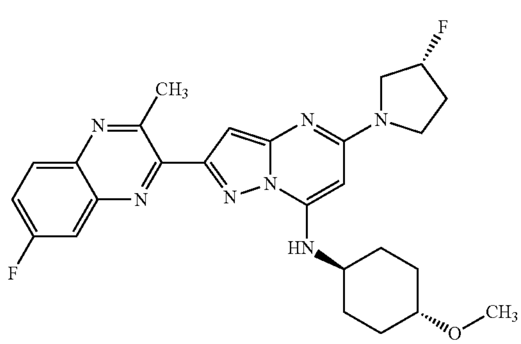 [SMILES: CO[C@H]1CC[C@H](Nc2cc(N3CC[C@@H](F)C3)nc3cc(-c4nc5cc(F)ccc5nc4C)nn23)CC1] | HCl | 494 (M + H) |

TABLE OF EXAMPLES-continued

| Example | Structure | Salt | MS (APCI) |
|---|---|---|---|
| 1.090 | 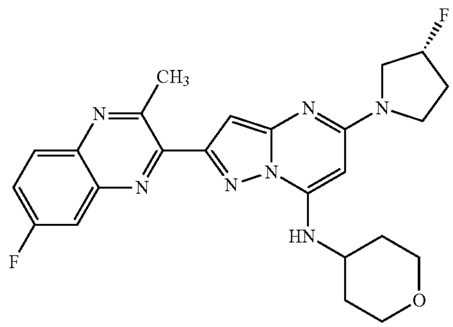 [SMILES: Cc1nc2ccc(F)cc2nc1-c1cc2nc(N3CC[C@@H](F)C3)cc(NC3CCOCC3)n2n1] | HCl | 466 (M + H) |
| 1.091 | 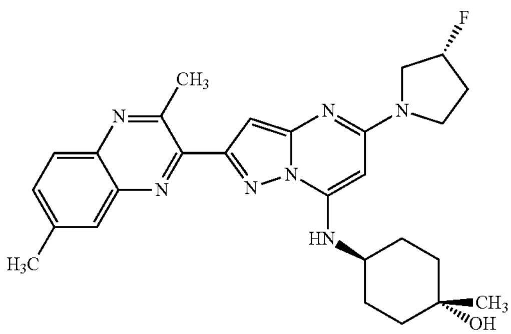 [SMILES: Cc1ccc2nc(C)c(-c3cc4nc(N5CC[C@@H](F)C5)cc(N[C@H]5CC[C@](C)(O)CC5)n4n3)nc2c1] | HCl | 490 (M + H) |
| 1.092 | 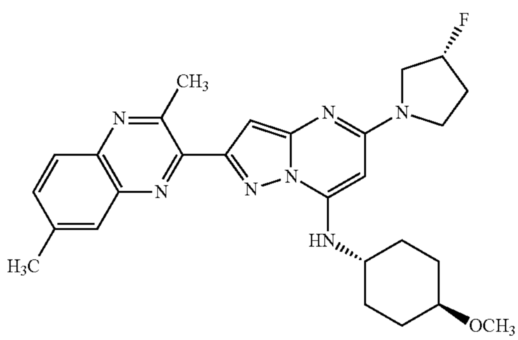 [SMILES: CO[C@H]1CC[C@H](Nc2cc(N3CC[C@@H](F)C3)nc3cc(-c4nc5cc(C)ccc5nc4C)nn23)CC1] | HCl 4/5 HCl | 490 (M + H) |
| 1.093 | 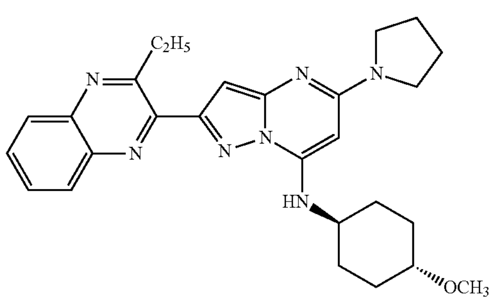 [SMILES: CCc1nc2ccccc2nc1-c1cc2nc(N3CCCC3)cc(N[C@H]3CC[C@H](OC)CC3)n2n1] | 2 HCl | 472 (M + H) |
| 1.094 | 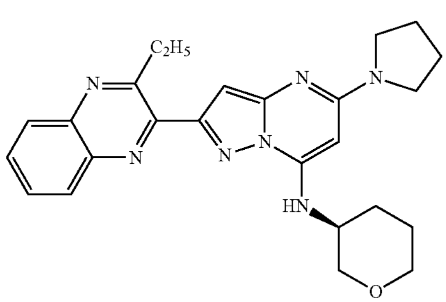 [SMILES: CCc1nc2ccccc2nc1-c1cc2nc(N3CCCC3)cc(N[C@H]3CCCOC3)n2n1] | 3/2 HCl | 444 (M + H) |

TABLE OF EXAMPLES-continued

| Example | Structure | Salt | MS (APCI) |
|---|---|---|---|
| 1.095 | 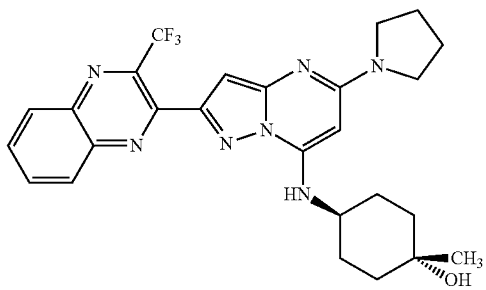 [SMILES: C[C@]1(O)CC[C@H](Nc2cc(N3CCCC3)nc3cc(-c4nc5ccccc5nc4C(F)(F)F)nn23)CC1] | 3/4 HCl | 512 (M + H) |
| 1.096 | 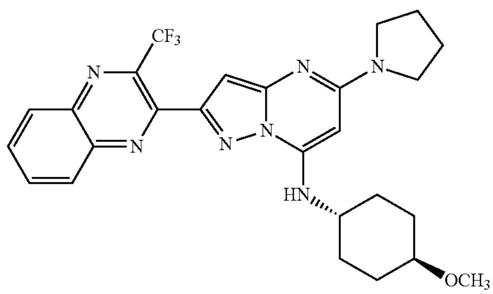 [SMILES: CO[C@H]1CC[C@H](Nc2cc(N3CCCC3)nc3cc(-c4nc5ccccc5nc4C(F)(F)F)nn23)CC1] | HCl | 512 (M + H) |
| 1.097 | 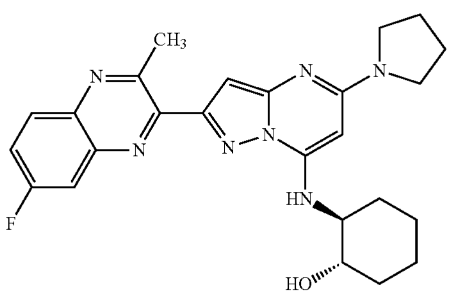 [SMILES: Cc1nc2ccc(F)cc2nc1-c1cc2nc(N3CCCC3)cc(N[C@H]3CCCC[C@@H]3O)n2n1] | HCl | 462 (M + H) |
| 1.098 | 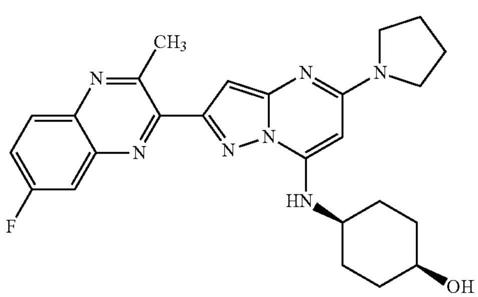 [SMILES: Cc1nc2ccc(F)cc2nc1-c1cc2nc(N3CCCC3)cc(N[C@H]3CC[C@@H](O)CC3)n2n1] | HCl | 462 (M + H) |
| 1.099 | 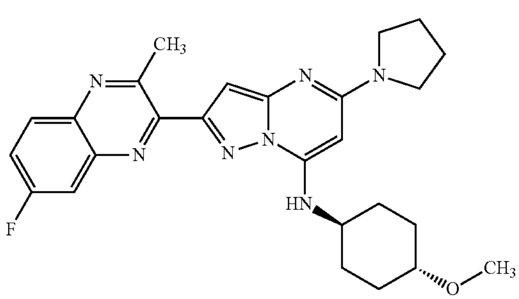 [SMILES: CO[C@H]1CC[C@H](Nc2cc(N3CCCC3)nc3cc(-c4nc5cc(F)ccc5nc4C)nn23)CC1] | HCl | 476 (M + H) |

TABLE OF EXAMPLES-continued

| Example | Structure | Salt | MS (APCI) |
|---|---|---|---|
| 1.100 | 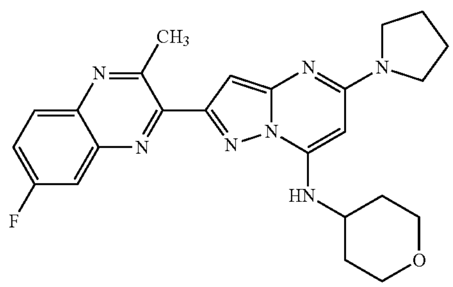 [SMILES: Cc1nc2ccc(F)cc2nc1-c1cc2nc(N3CCCC3)cc(NC3CCOCC3)n2n1] | HCl | 448 (M + H) |
| 1.101 | 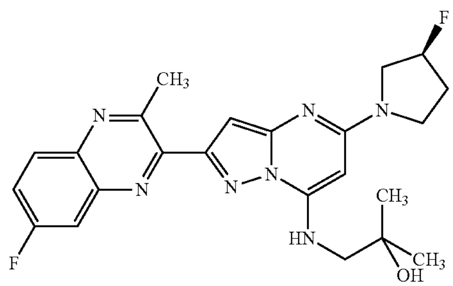 [SMILES: Cc1nc2ccc(F)cc2nc1-c1cc2nc(N3CC[C@H](F)C3)cc(NCC(C)(C)O)n2n1] | HCl | 454 (M + H) |
| 1.102 | 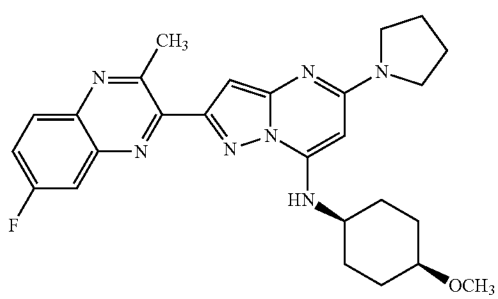 [SMILES: CO[C@H]1CC[C@@H](Nc2cc(N3CCCC3)nc3cc(-c4nc5cc(F)ccc5nc4C)nn23)CC1] | HCl | 476 (M + H) |
| 1.103 | 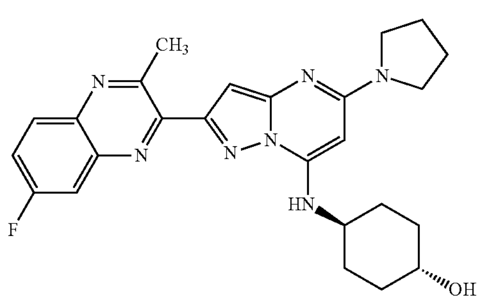 [SMILES: Cc1nc2ccc(F)cc2nc1-c1cc2nc(N3CCCC3)cc(N[C@H]3CC[C@H](O)CC3)n2n1] | HCl | 462 (M + H) |
| 1.104 | 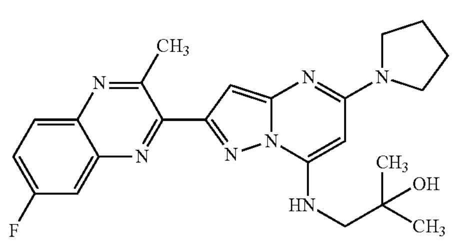 [SMILES: Cc1nc2ccc(F)cc2nc1-c1cc2nc(N3CCCC3)cc(NCC(C)(C)O)n2n1] | HCl | 436 (M + H) |

TABLE OF EXAMPLES-continued

| Example | Structure | Salt | MS (APCI) |
|---------|-----------|------|-----------|
| 1.105 | 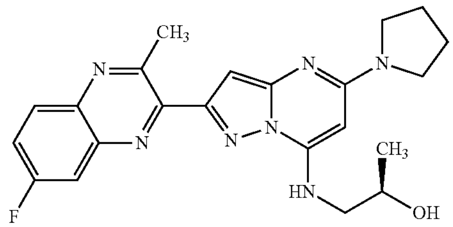 [SMILES: Cc1nc2ccc(F)cc2nc1-c1cc2nc(N3CCCC3)cc(NC[C@@H](C)O)n2n1] | HCl | 422 (M + H) |
| 1.106 | 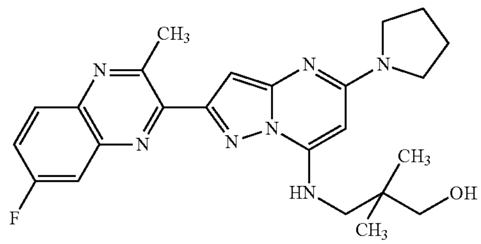 [SMILES: Cc1nc2ccc(F)cc2nc1-c1cc2nc(N3CCCC3)cc(NCC(C)(C)CO)n2n1] | HCl | 450 (M + H) |
| 1.107 | 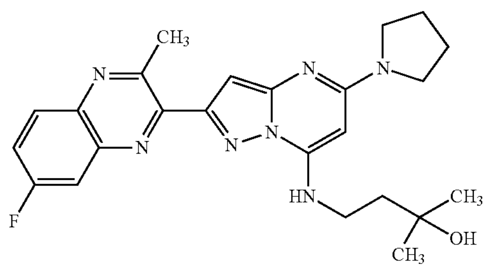 [SMILES: Cc1nc2ccc(F)cc2nc1-c1cc2nc(N3CCCC3)cc(NCCC(C)(C)O)n2n1] | HCl | 450 (M + H) |
| 1.108 | 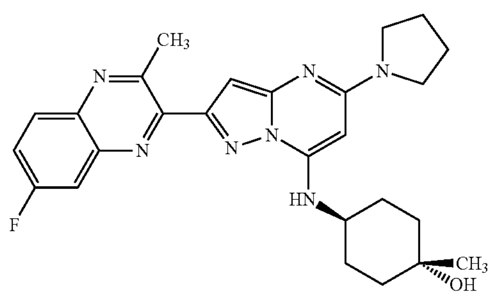 [SMILES: Cc1nc2ccc(F)cc2nc1-c1cc2nc(N3CCCC3)cc(N[C@H]3CC[C@](C)(O)CC3)n2n1] | HCl | 476 (M + H) |
| 1.109 | 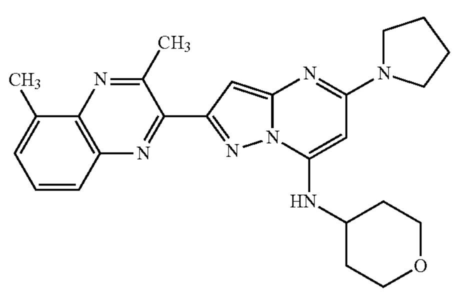 [SMILES: Cc1nc2c(C)cccc2nc1-c1cc2nc(N3CCCC3)cc(NC3CCOCC3)n2n1] | 2 HCl | 444 (M + H) |

TABLE OF EXAMPLES-continued

| Example | Structure | Salt | MS (APCI) |
|---------|-----------|------|-----------|
| 1.110 | 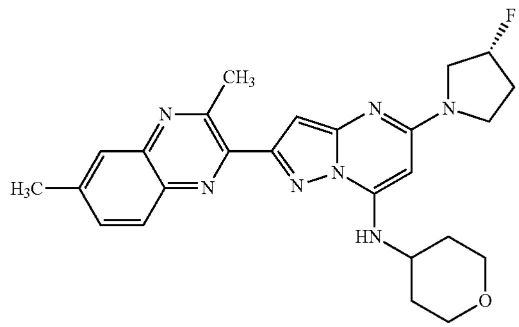 [SMILES: Cc1ccc2nc(-c3cc4nc(N5CC[C@@H](F)C5)cc(NC5CCOCC5)n4n3)c(C)nc2c1] | Free form | 462 (M + H) |
| 1.111 | 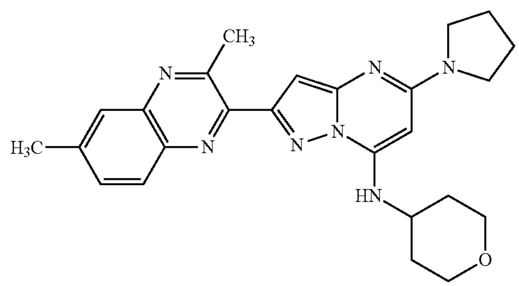 [SMILES: Cc1ccc2nc(-c3cc4nc(N5CCCC5)cc(NC5CCOCC5)n4n3)c(C)nc2c1] | 2 HCl | 444 (M + H) |
| 1.112 | 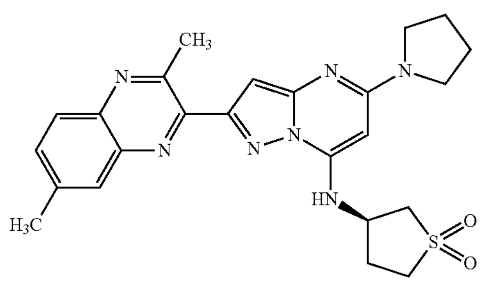 [SMILES: Cc1ccc2nc(C)c(-c3cc4nc(N5CCCC5)cc(N[C@@H]5CCS(=O)(=O)C5)n4n3)nc2c1] | 2 HCl | 478 (M + H) |
| 1.113 | 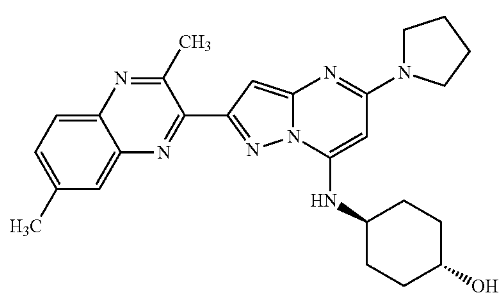 [SMILES: Cc1ccc2nc(C)c(-c3cc4nc(N5CCCC5)cc(N[C@H]5CC[C@H](O)CC5)n4n3)nc2c1] | HCl | 458 (M + H) |
| 1.114 | 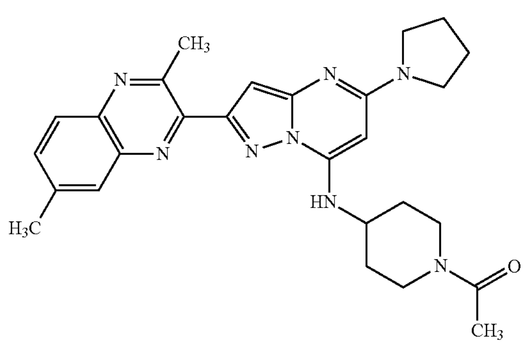 [SMILES: CC(=O)N1CCC(Nc2cc(N3CCCC3)nc3cc(-c4nc5cc(C)ccc5nc4C)nn23)CC1] | 5/2 HCl | 485 (M + H) |

TABLE OF EXAMPLES-continued

| Example | Structure | Salt | MS (APCI) |
|---|---|---|---|
| 1.115 | 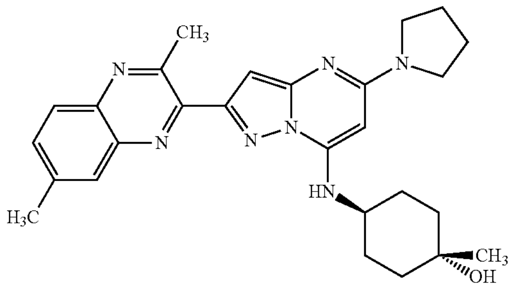 [SMILES: Cc1ccc2nc(C)c(-c3cc4nc(N5CCCC5)cc(N[C@H]5CC[C@](C)(O)CC5)n4n3)nc2c1] | HCl<br>2 HCl | 472 (M + H) |
| 1.116 | 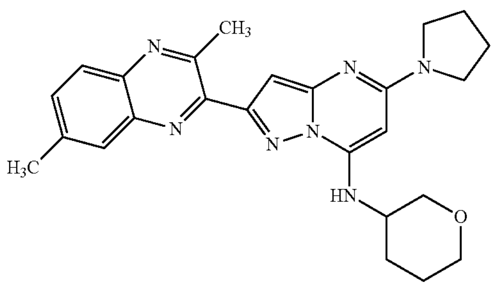 [SMILES: Cc1ccc2nc(C)c(-c3cc4nc(N5CCCC5)cc(NC5CCCOC5)n4n3)nc2c1] | 3/2 HCl | 444 (M + H) |
| 1.117 | 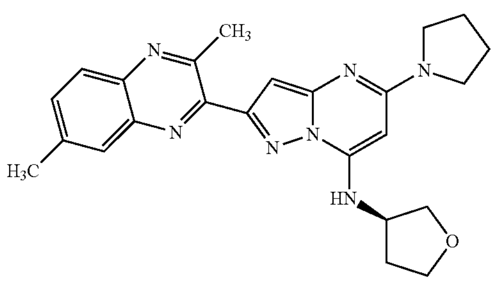 [SMILES: Cc1ccc2nc(C)c(-c3cc4nc(N5CCCC5)cc(N[C@@H]5CCOC5)n4n3)nc2c1] | 2 HCl | 430 (M + H) |
| 1.118 | 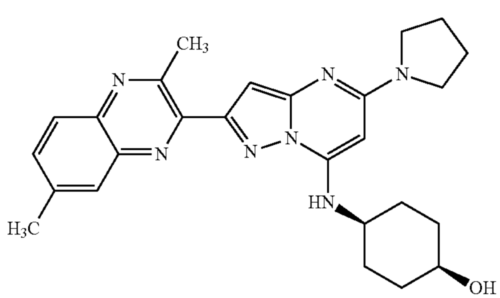 [SMILES: Cc1ccc2nc(C)c(-c3cc4nc(N5CCCC5)cc(N[C@H]5CC[C@@H](O)CC5)n4n3)nc2c1] | HCl | 458 (M + H) |
| 1.119 | 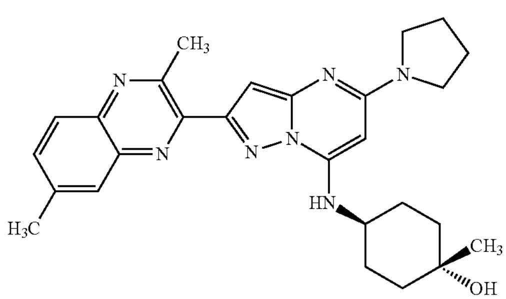 [SMILES: Cc1ccc2nc(C)c(-c3cc4nc(N5CCCC5)cc(N[C@H]5CC[C@](C)(O)CC5)n4n3)nc2c1] | HCl | 472 (M + H) |

TABLE OF EXAMPLES-continued

| Example | Structure | Salt | MS (APCI) |
|---|---|---|---|
| 1.120 | 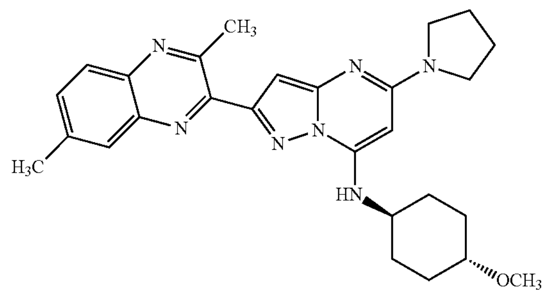 [SMILES: CO[C@H]1CC[C@H](Nc2cc(N3CCCC3)nc3cc(-c4nc5cc(C)ccc5nc4C)nn23)CC1] | HCl 2 HCl | 472 (M + H) |
| 1.121 | 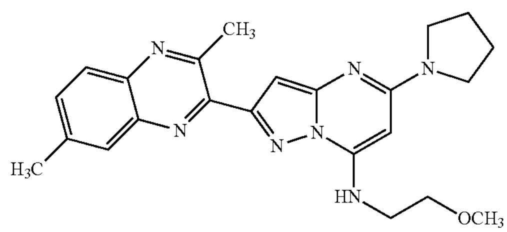 [SMILES: COCCNc1cc(N2CCCC2)nc2cc(-c3nc4cc(C)ccc4nc3C)nn12] | 2 HCl | 418 (M + H) |
| 1.122 | 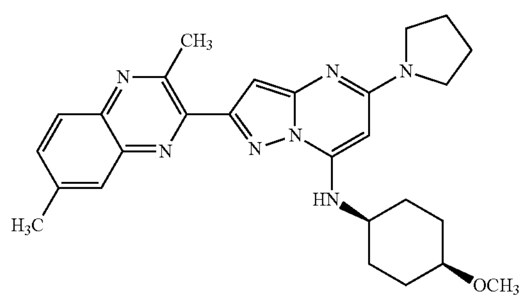 [SMILES: CO[C@H]1CC[C@@H](Nc2cc(N3CCCC3)nc3cc(-c4nc5cc(C)ccc5nc4C)nn23)CC1] | HCl | 472 (M + H) |
| 1.123 | 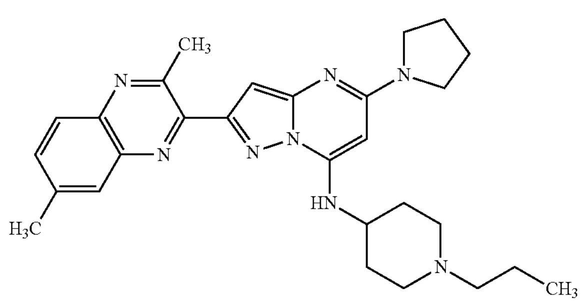 [SMILES: CCCN1CCC(Nc2cc(N3CCCC3)nc3cc(-c4nc5cc(C)ccc5nc4C)nn23)CC1] | 3 HCl | 485 (M + H) |
| 1.124 | 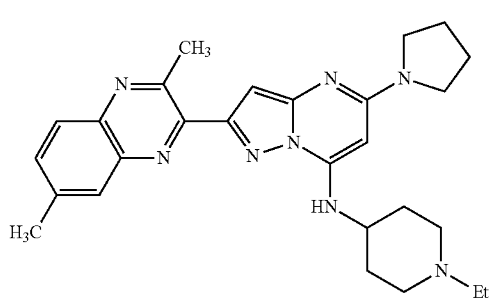 [SMILES: CCN1CCC(Nc2cc(N3CCCC3)nc3cc(-c4nc5cc(C)ccc5nc4C)nn23)CC1] | 3 HCl | 471 (M + H) |

TABLE OF EXAMPLES-continued

| Example | Structure | Salt | MS (APCI) |
|---|---|---|---|
| 1.125 | 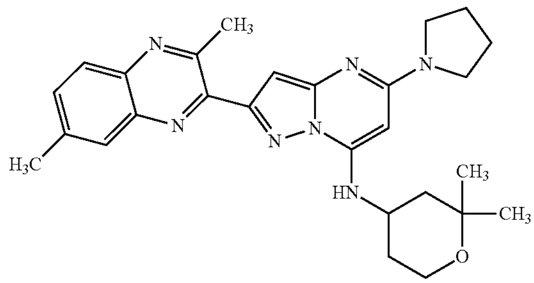 | 2 HCl | 472 (M + H) |
| 1.126 | 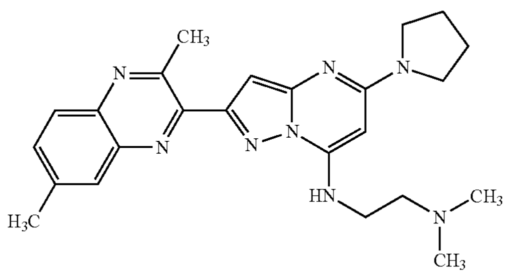 [SMILES: Cc1ccc2nc(C)c(-c3cc4nc(N5CCCC5)cc(NCCN(C)C)n4n3)nc2c1] | 3 HCl | 431 (M + H) |
| 1.127 | 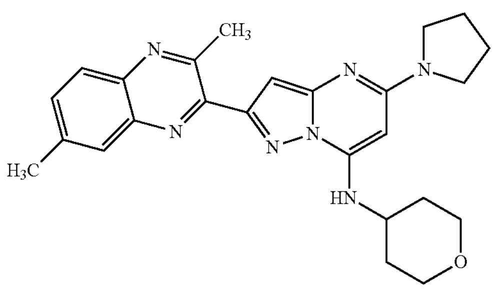 [SMILES: Cc1ccc2nc(C)c(-c3cc4nc(N5CCCC5)cc(NC5CCOCC5)n4n3)nc2c1] | HCl<br>2 HCl | 444 (M + H) |
| 1.128 | 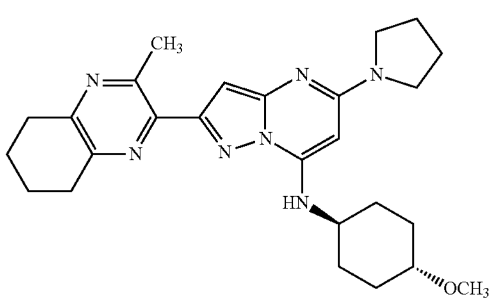 [SMILES: CO[C@H]1CC[C@H](Nc2cc(N3CCCC3)nc3cc(-c4nc5c(nc4C)CCCC5)nn23)CC1] | HCl | 462 (M + H) |
| 1.129 | 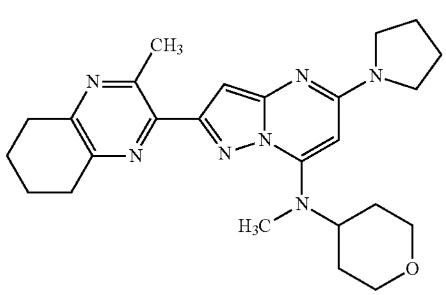 [SMILES: Cc1nc2c(nc1-c1cc3nc(N4CCCC4)cc(N(C)C4CCOCC4)n3n1)CCCC2] | HCl | 448 (M + H) |

TABLE OF EXAMPLES-continued

| Example | Structure | Salt | MS (APCI) |
|---|---|---|---|
| 1.130 | 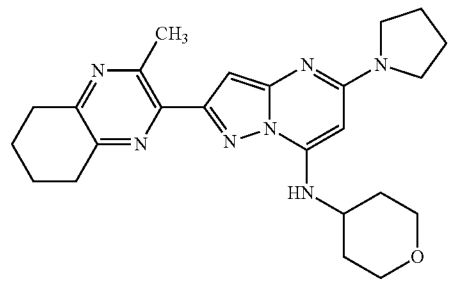 [SMILES: Cc1nc2c(nc1-c1cc3nc(N4CCCC4)cc(NC4CCOCC4)n3n1)CCCC2] | Free form | 434 (M + H) |
| 1.131 | 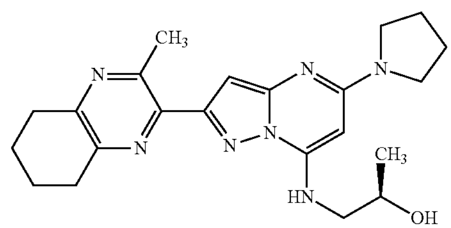 [SMILES: Cc1nc2c(nc1-c1cc3nc(N4CCCC4)cc(NC[C@@H](C)O)n3n1)CCCC2] | 3/5 HCl | 408 (M + H) |
| 1.132 | 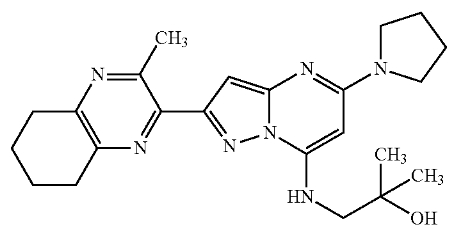 [SMILES: Cc1nc2c(nc1-c1cc3nc(N4CCCC4)cc(NCC(C)(C)O)n3n1)CCCC2] | HCl | 422 (M + H) |
| 1.133 | 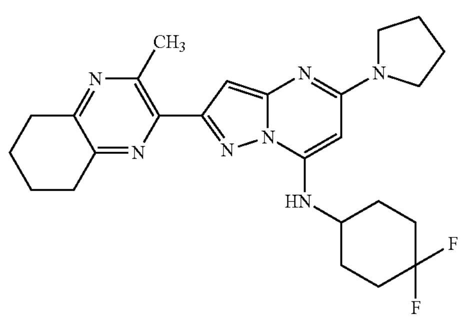 [SMILES: Cc1nc2c(nc1-c1cc3nc(N4CCCC4)cc(NC4CCC(F)(F)CC4)n3n1)CCCC2] | Free form | 468 (M + H) |
| 1.134 | 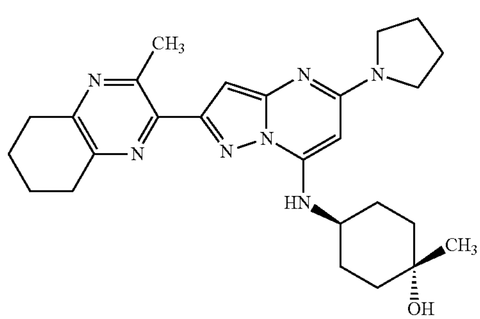 [SMILES: Cc1nc2c(nc1-c1cc3nc(N4CCCC4)cc(N[C@H]4CC[C@](C)(O)CC4)n3n1)CCCC2] | HCl | 462 (M + H) |

TABLE OF EXAMPLES-continued

| Example | Structure | Salt | MS (APCI) |
|---|---|---|---|
| 1.135 | 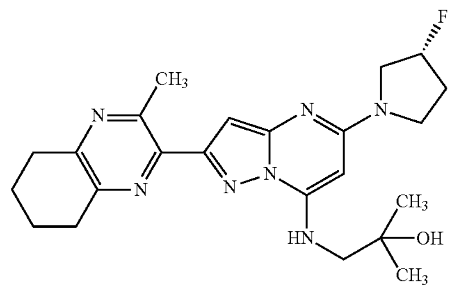 [SMILES: Cc1nc2c(nc1-c1cc3nc(N4CC[C@@H](F)C4)cc(NCC(C)(C)O)n3n1)CCCC2] | HCl | 440 (M + H) |
| 1.136 | 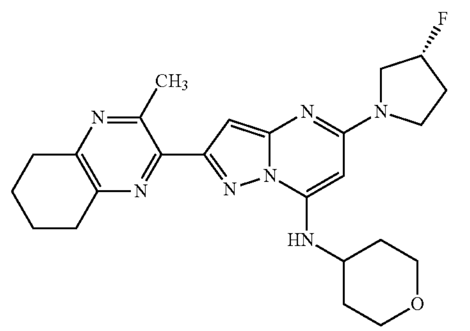 [SMILES: Cc1nc2c(nc1-c1cc3nc(N4CC[C@@H](F)C4)cc(NC4CCOCC4)n3n1)CCCC2] | 3/4 HCl | 452 (M + H) |
| 1.137 | 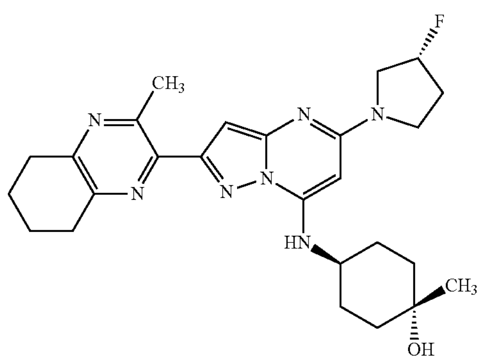 [SMILES: Cc1nc2c(nc1-c1cc3nc(N4CC[C@@H](F)C4)cc(N[C@H]4CC[C@](C)(O)CC4)n3n1)CCCC2] | HCl | 480 (M + H) |
| 1.138 | 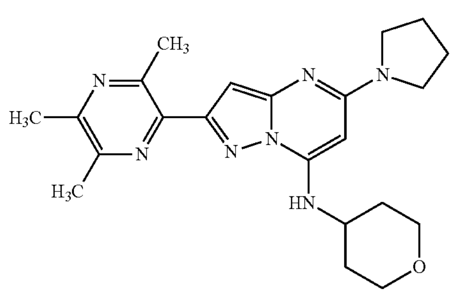 [SMILES: Cc1nc(C)c(-c2cc3nc(N4CCCC4)cc(NC4CCOCC4)n3n2)nc1C] | Free form | 408 (M + H) |
| 1.139 | 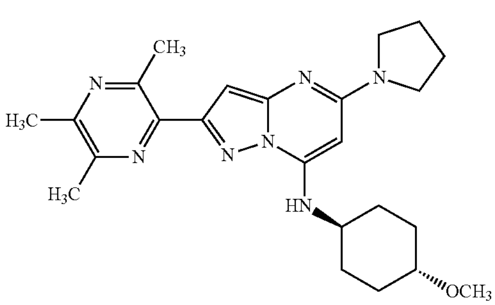 [SMILES: CO[C@H]1CC[C@H](Nc2cc(N3CCCC3)nc3cc(-c4nc(C)c(C)nc4C)nn23)CC1] | Free form | 436 (M + H) |

TABLE OF EXAMPLES-continued
| Example | Structure | Salt | MS (APCI) |
|---|---|---|---|
| 1.140 | 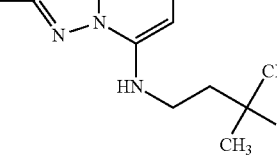 | 6/5 HCl | 410 (M + H) |
| 1.141 | 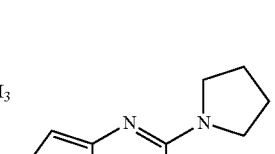 | HCl | 436 (M + H) |
| 1.142 | 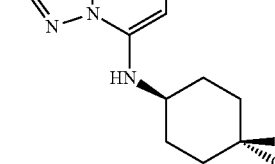 | Free form | 396 (M + H) |
| 1.143 | 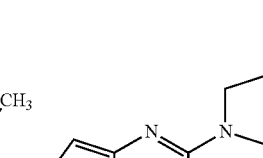 | HCl | 422 (M + H) |
| 1.144 | 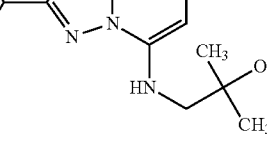 | HCl<br>Free form | 422 (M + H) |

TABLE OF EXAMPLES-continued

| Example | Structure | Salt | MS (APCI) |
|---|---|---|---|
| 1.145 | 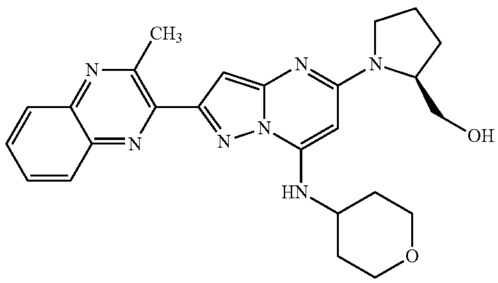 [SMILES: Cc1nc2ccccc2nc1-c1cc2nc(N3CCC[C@H]3CO)cc(NC3CCOCC3)n2n1] | HCl | 460 (M + H) |
| 1.146 | 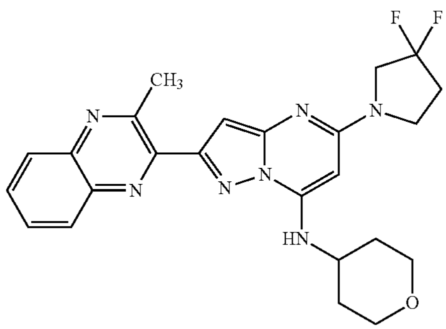 | 3/2 HCl | 446 (M + H) |
| 1.147 | 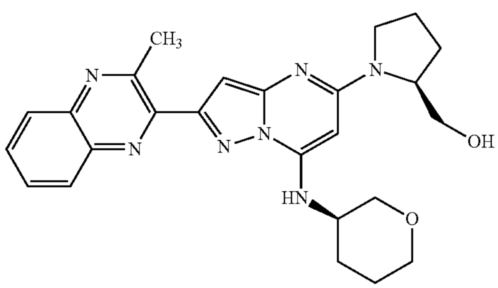 [SMILES: Cc1nc2ccccc2nc1-c1cc2nc(N3CCC[C@H]3CO)cc(N[C@@H]3CCCOC3)n2n1] | 3/2 HCl | 460 (M + H) |
| 1.148 | 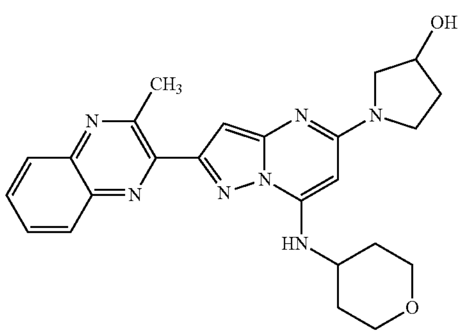 [SMILES: Cc1nc2ccccc2nc1-c1cc2nc(N3CCC(O)C3)cc(NC3CCOCC3)n2n1] | HCl | 446 (M + H) |
| 1.149 | 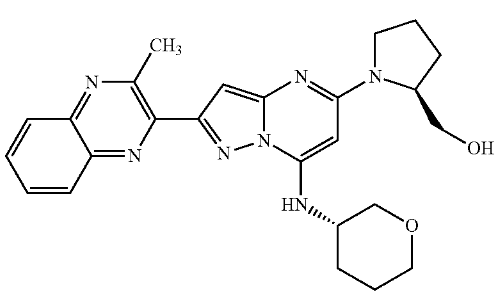 [SMILES: Cc1nc2ccccc2nc1-c1cc2nc(N3CCC[C@H]3CO)cc(N[C@H]3CCCOC3)n2n1] | 3/2 HCl | 460 (M + H) |

TABLE OF EXAMPLES-continued

| Example | Structure | Salt | MS (APCI) |
|---|---|---|---|
| 1.150 | 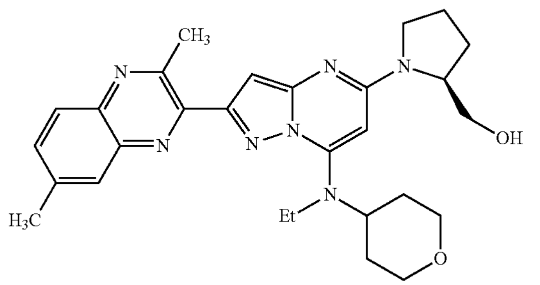 [SMILES: CCN(c1cc(N2CCC[C@H]2CO)nc2cc(-c3nc4cc(C)ccc4nc3C)nn12)C1CCOCC1] | 3/2 HCl | 502 (M + H) |
| 1.151 | 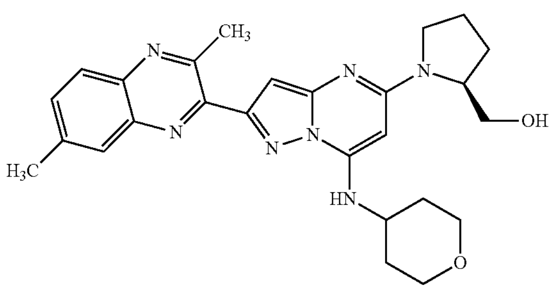 [SMILES: Cc1ccc2nc(C)c(-c3cc4nc(N5CCC[C@H]5CO)cc(NC5CCOCC5)n4n3)nc2c1] | HCl | 474 (M + H) |
| 1.152 | 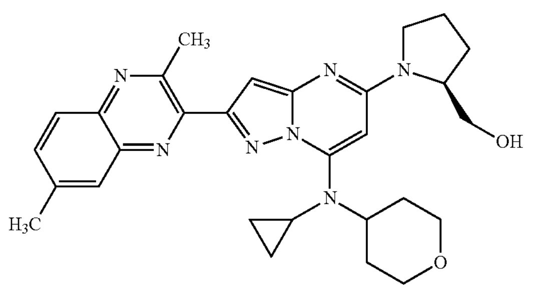 [SMILES: Cc1ccc2nc(C)c(-c3cc4nc(N5CCC[C@H]5CO)cc(N(C5CCOCC5)C5CC5)n4n3)nc2c1] | 3/2 HCl | 514 (M + H) |
| 1.153 | 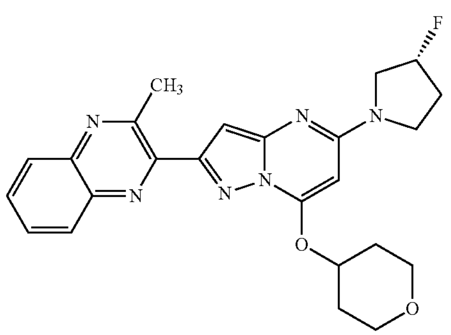 [SMILES: Cc1nc2ccccc2nc1-c1cc2nc(N3CC[C@@H](F)C3)cc(OC3CCOCC3)n2n1] | HCl | 449 (M + H) |
| 1.154 | 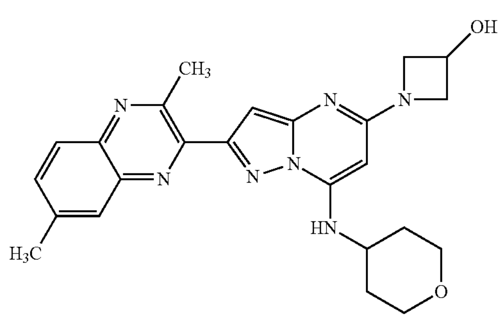 [SMILES: Cc1ccc2nc(C)c(-c3cc4nc(N5CC(O)C5)cc(NC5CCOCC5)n4n3)nc2c1] | 2 HCl | 446 (M + H) |

TABLE OF EXAMPLES-continued

| Example | Structure | Salt | MS (APCI) |
|---|---|---|---|
| 1.155 | 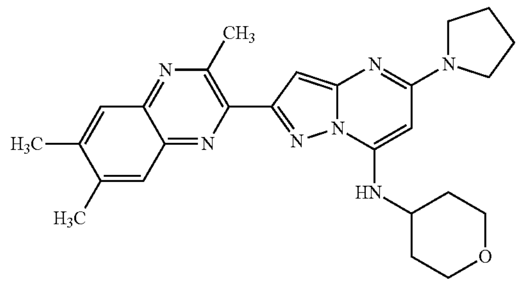 [SMILES: Cc1cc2nc(C)c(-c3cc4nc(N5CCCC5)cc(NC5CCOCC5)n4n3)nc2cc1C] | 2 HCl | 458 (M + H) |
| 1.156 | 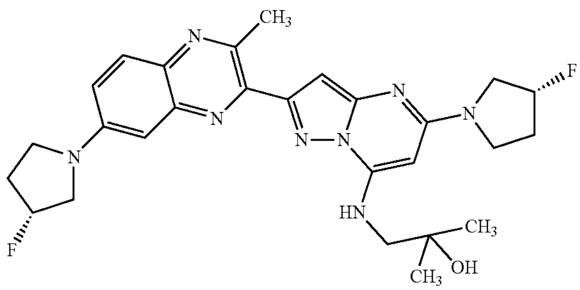 [SMILES: Cc1nc2ccc(N3CC[C@@H](F)C3)cc2nc1-c1cc2nc(N3CC[C@@H](F)C3)cc(NCC(C)(C)O)n2n1] | Free form | 523 (M + H) |
| 1.157 | 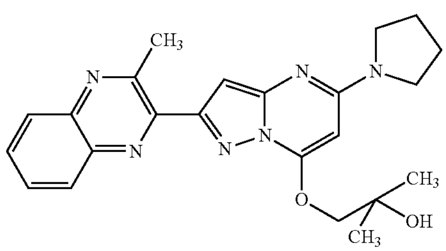 [SMILES: Cc1nc2ccccc2nc1-c1cc2nc(N3CCCC3)cc(OCC(C)(C)O)n2n1] | Free form | 419 (M + H) |
| 1.158 | 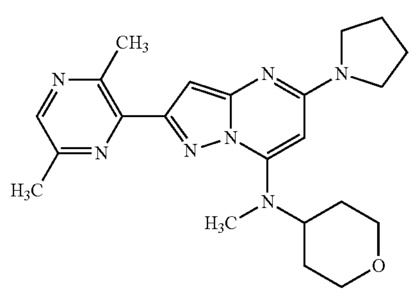 [SMILES: Cc1cnc(C)c(-c2cc3nc(N4CCCC4)cc(N(C)C4CCOCC4)n3n2)n1] | Free form | 408 (M + H) |
| 1.159 | 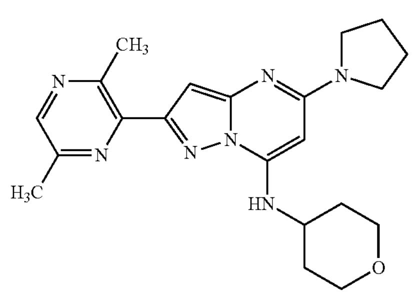 [SMILES: Cc1cnc(C)c(-c2cc3nc(N4CCCC4)cc(NC4CCOCC4)n3n2)n1] | Free form | 394 (M + H) |

TABLE OF EXAMPLES-continued

| Example | Structure | Salt | MS (APCI) |
|---|---|---|---|
| 1.160 | (3,5,6-trimethylpyrazin-2-yl / pyrazolo[1,5-a]pyrimidine with 3-fluoropyrrolidin-1-yl and 2-hydroxy-2-methylpropylamino substituents) | Free form | 414 (M + H) |
| 1.161 | (4-methylquinolin-2-yl / pyrazolo[1,5-a]pyrimidine with 3-fluoropyrrolidin-1-yl and tetrahydropyran-4-ylamino substituents) | 2 HCl | 447 (M + H) |
| 1.162 | (3-methylquinolin-2-yl / pyrazolo[1,5-a]pyrimidine with 3-fluoropyrrolidin-1-yl and tetrahydropyran-4-ylamino substituents) | 2 HCl | 447 (M + H) |
| 1.163 | (3-methylquinoxalin-2-yl / pyrazolo[1,5-a]pyrimidine with morpholin-4-yl and tetrahydropyran-4-ylamino substituents) | 2 HCl | 446 (M + H) |
| 1.164 | (3,6,7-trimethylquinoxalin-2-yl / pyrazolo[1,5-a]pyrimidine with 2-(hydroxymethyl)pyrrolidin-1-yl and tetrahydropyran-4-ylamino substituents) | 2 HCl | 488 (M + H) |

TABLE OF EXAMPLES-continued
| Example | Structure | Salt | MS (APCI) |
|---|---|---|---|
| 1.165 | 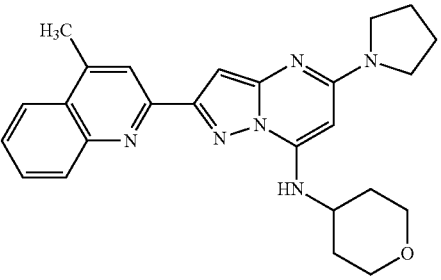 [SMILES: Cc1cc(-c2cc3nc(N4CCCC4)cc(NC4CCOCC4)n3n2)nc2ccccc12] | 2 HCl | 429 (M + H) |
| 1.166 | 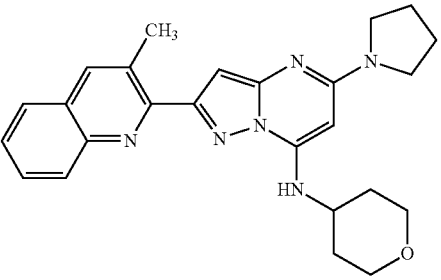 [SMILES: Cc1cc2ccccc2nc1-c1cc2nc(N3CCCC3)cc(NC3CCOCC3)n2n1] | 2 HCl | 429 (M + H) |
| 1.167 | 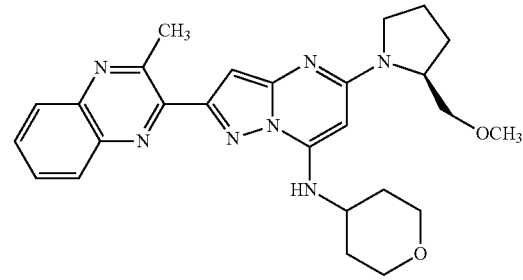 [SMILES: COC[C@@H]1CCCN1c1cc(NC2CCOCC2)n2nc(-c3nc4ccccc4nc3C)cc2n1] | 2 HCl | 474 (M + H) |
| 1.168 | 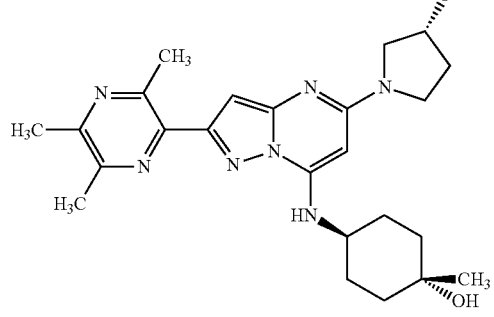 | Free form | 454 (M + H) |
| 1.169 | 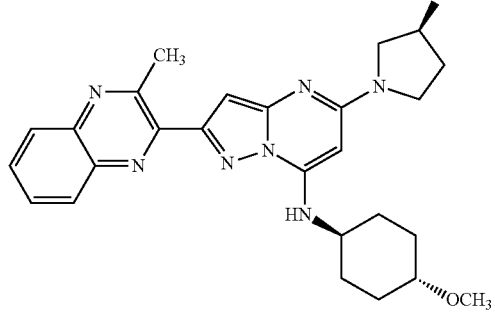 | 3/2 HCl | 476 (M + H) |

TABLE OF EXAMPLES-continued

| Example | Structure | Salt | MS (APCI) |
|---|---|---|---|
| 1.170 | 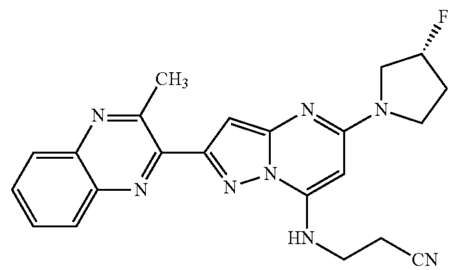 [SMILES: Cc1nc2ccccc2nc1-c1cc2nc(N3CC[C@@H](F)C3)cc(NCCC#N)n2n1] | HCl | 417 (M + H) |
| 1.171 | 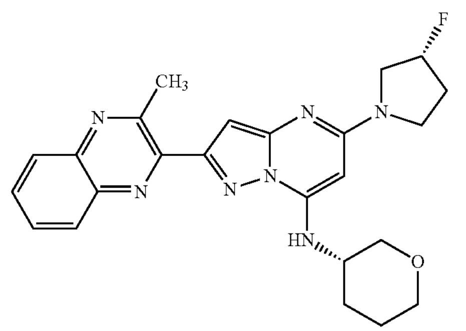 [SMILES: Cc1nc2ccccc2nc1-c1cc2nc(N3CC[C@@H](F)C3)cc(N[C@H]3CCCOC3)n2n1] | HCl | 448 (M + H) |
| 1.172 | 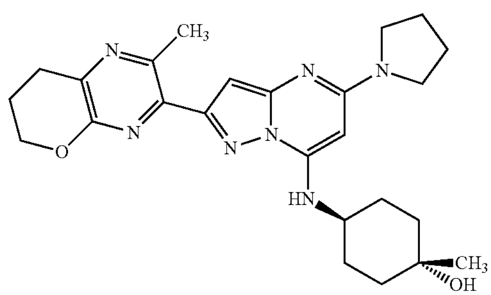 [SMILES: Cc1nc2c(nc1-c1cc3nc(N4CCCC4)cc(N[C@H]4CC[C@](C)(O)CC4)n3n1)OCCC2] | 3/2 HCl | 464 (M + H) |
| 1.173 | 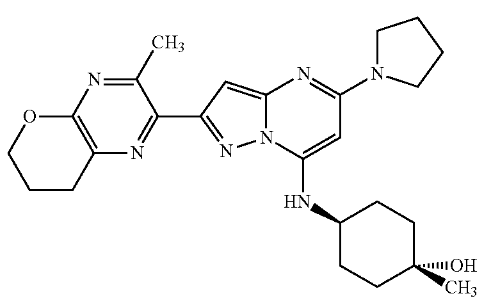 [SMILES: Cc1nc2c(nc1-c1cc3nc(N4CCCC4)cc(N[C@H]4CC[C@](C)(O)CC4)n3n1)CCCO2] | 3/2 HCl | 464 (M + H) |
| 1.174 | 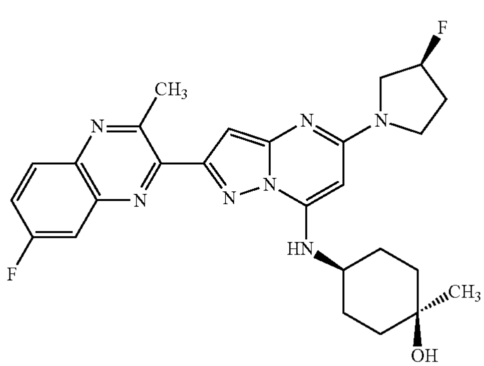 [SMILES: Cc1nc2ccc(F)cc2nc1-c1cc2nc(N3CC[C@H](F)C3)cc(N[C@H]3CC[C@@](C)(O)CC3)n2n1] | HCl | 494 (M + H) |

TABLE OF EXAMPLES-continued

| Example | Structure | Salt | MS (APCI) |
| --- | --- | --- | --- |
| 1.175 | 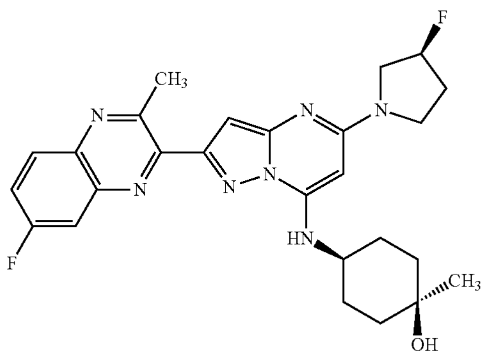 [SMILES: Cc1nc2ccc(F)cc2nc1-c1cc2nc(N3CC[C@H](F)C3)cc(N[C@H]3CC[C@@](C)(O)CC3)n2n1] | HCl | 494 (M + H) |
| 1.176 | 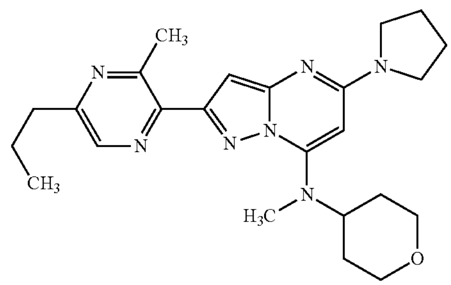 [SMILES: CCCc1cnc(-c2cc3nc(N4CCCC4)cc(N(C)C4CCOCC4)n3n2)c(C)n1] | Free form | 436 (M + H) |
| 1.177 | 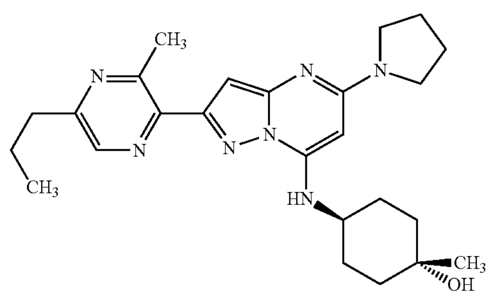 [SMILES: CCCc1cnc(-c2cc3nc(N4CCCC4)cc(N[C@H]4CC[C@](C)(O)CC4)n3n2)c(C)n1] | Free form | 450 (M + H) |
| 1.178 | 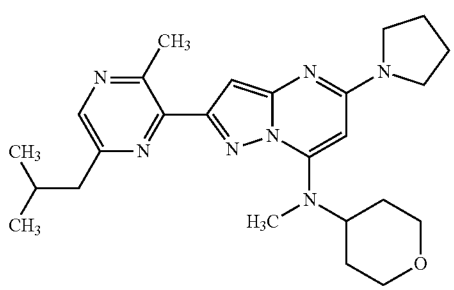 [SMILES: Cc1ncc(CC(C)C)nc1-c1cc2nc(N3CCCC3)cc(N(C)C3CCOCC3)n2n1] | Free form | 450 (M + H) |
| 1.179 | 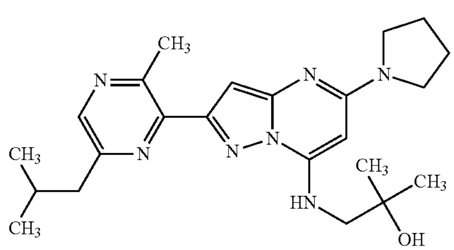 [SMILES: Cc1ncc(CC(C)C)nc1-c1cc2nc(N3CCCC3)cc(NCC(C)(C)O)n2n1] | Free form | 424 (M + H) |

TABLE OF EXAMPLES-continued

| Example | Structure | Salt | MS (APCI) |
|---|---|---|---|
| 1.180 | 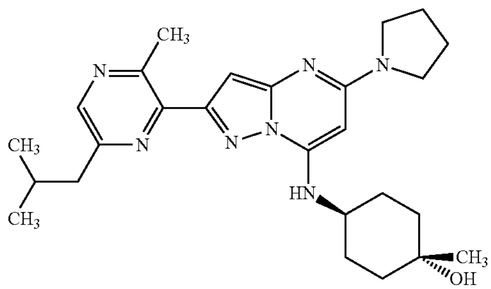 [SMILES: Cc1ncc(CC(C)C)nc1-c1cc2nc(N3CCCC3)cc(N[C@H]3CC[C@](C)(O)CC3)n2n1] | Free form | 464 (M + H) |
| 1.181 | 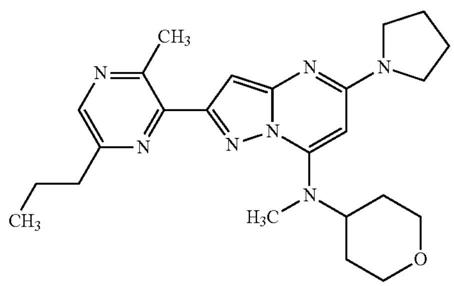 [SMILES: CCCc1cnc(C)c(-c2cc3nc(N4CCCC4)cc(N(C)C4CCOCC4)n3n2)n1] | HCl | 436 (M + H) |
| 1.182 | 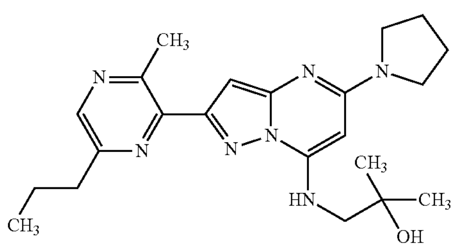 [SMILES: CCCc1cnc(C)c(-c2cc3nc(N4CCCC4)cc(NCC(C)(C)O)n3n2)n1] | HCl | 410 (M + H) |
| 1.183 | 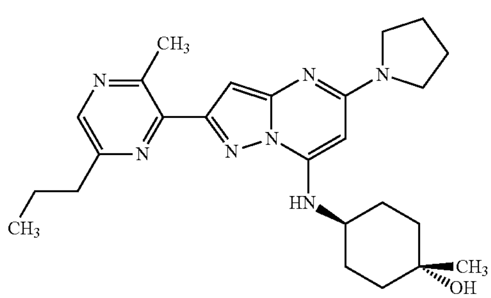 [SMILES: CCCc1cnc(C)c(-c2cc3nc(N4CCCC4)cc(N[C@H]4CC[C@](C)(O)CC4)n3n2)n1] | HCl | 450 (M + H) |
| 1.184 | 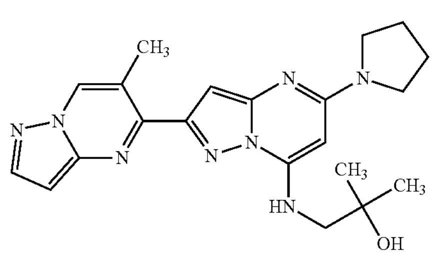 [SMILES: Cc1cn2nccc2nc1-c1cc2nc(N3CCCC3)cc(NCC(C)(C)O)n2n1] | HCl | 407 (M + H) |

TABLE OF EXAMPLES-continued
| Example | Structure | Salt | MS (APCI) |
|---|---|---|---|
| 1.185 | 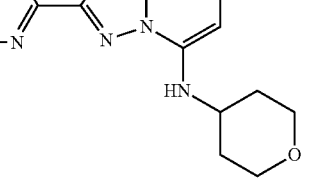 | Free form | 450 (M + H) |
| 1.186 | 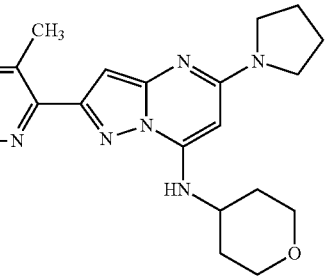 | Free form | 436 (M + H) |
| 1.187 | 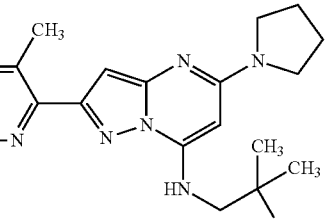 | Free form | 438 (M + H) |
| 1.188 | 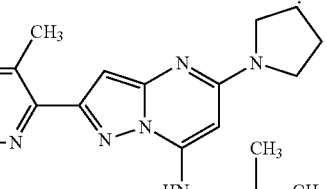 | Free form | 456 (M + H) |
| 1.189 | 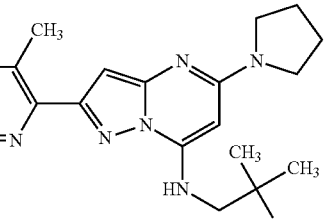 | HCl | 422 (M + H) |

TABLE OF EXAMPLES-continued

| Example | Structure | Salt | MS (APCI) |
|---|---|---|---|
| 1.190 | 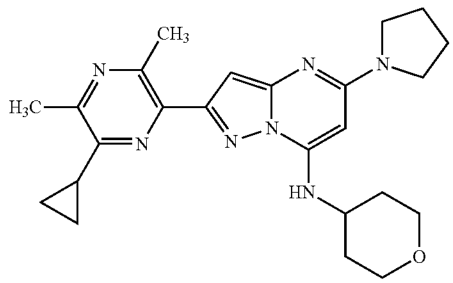 [SMILES: Cc1nc(C)c(C2CC2)nc1-c1cc2nc(N3CCCC3)cc(NC3CCOCC3)n2n1] | HCl | 434 (M + H) |
| 1.191 | 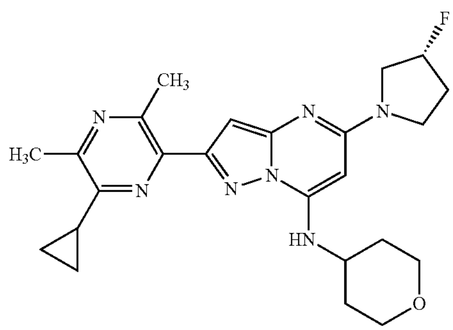 [SMILES: Cc1nc(C)c(C2CC2)nc1-c1cc2nc(N3CC[C@@H](F)C3)cc(NC3CCOCC3)n2n1] | HCl | 452 (M + H) |
| 1.192 | 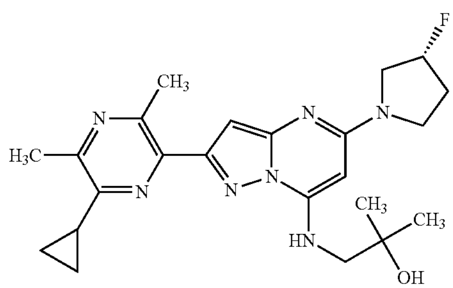 [SMILES: Cc1nc(C)c(C2CC2)nc1-c1cc2nc(N3CC[C@@H](F)C3)cc(NCC(C)(C)O)n2n1] | 2 HCl | 440 (M + H) |
| 1.193 | 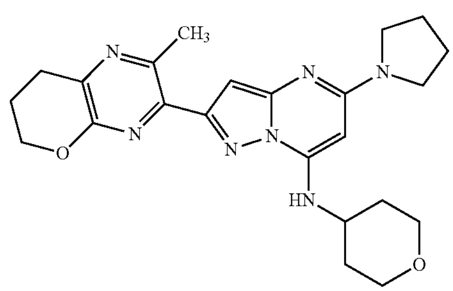 [SMILES: Cc1nc2c(nc1-c1cc3nc(N4CCCC4)cc(NC4CCOCC4)n3n1)OCCC2] | 3/2 HCl | 436 (M + H) |
| 1.194 | 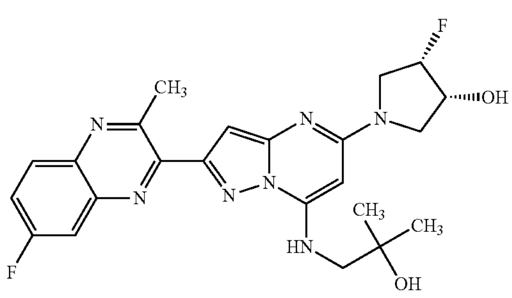 [SMILES: Cc1nc2ccc(F)cc2nc1-c1cc2nc(N3C[C@@H](O)[C@@H](F)C3)cc(NCC(C)(C)O)n2n1] | Free form | 470 (M + H) |

TABLE OF EXAMPLES-continued

| Example | Structure | Salt | MS (APCI) |
| --- | --- | --- | --- |
| 1.195 | 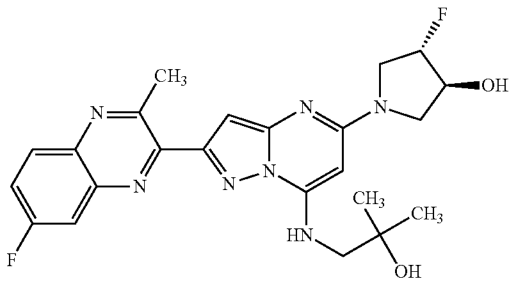 [SMILES: Cc1nc2ccc(F)cc2nc1-c1cc2nc(N3C[C@H](O)[C@@H](F)C3)cc(NCC(C)(C)O)n2n1] | Free form | 470 (M + H) |
| 1.196 | 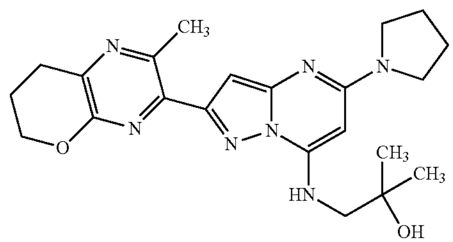 [SMILES: Cc1nc2c(nc1-c1cc3nc(N4CCCC4)cc(NCC(C)(C)O)n3n1)OCCC2] | 3/2 HCl | 424 (M + H) |
| 1.197 | 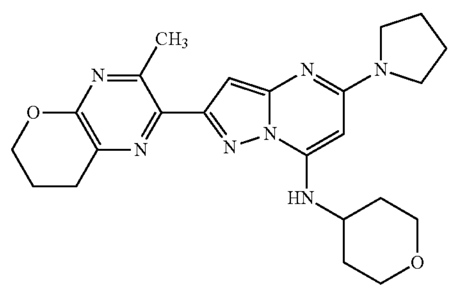 [SMILES: Cc1nc2c(nc1-c1cc3nc(N4CCCC4)cc(NC4CCOCC4)n3n1)CCCO2] | 5/2 HCl | 436 (M + H) |
| 1.198 | 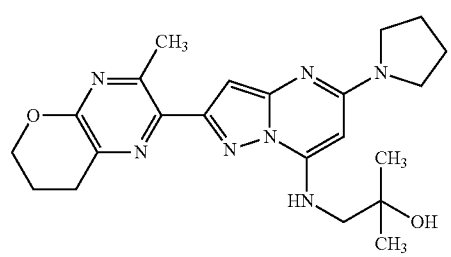 [SMILES: Cc1nc2c(nc1-c1cc3nc(N4CCCC4)cc(NCC(C)(C)O)n3n1)CCCO2] | 3/2 HCl | 424 (M + H) |
| 1.199 | 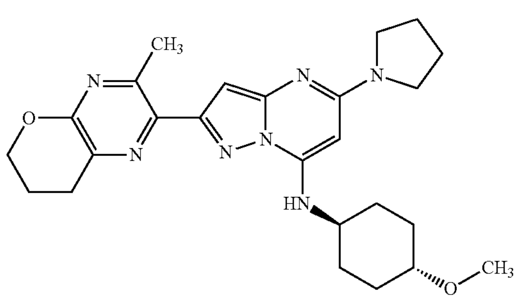 [SMILES: CO[C@H]1CC[C@H](Nc2cc(N3CCCC3)nc3cc(-c4nc5c(nc4C)OCCC5)nn23)CC1] | 3/2*HCl | 464 (M + H) |

TABLE OF EXAMPLES-continued

| Example | Structure | Salt | MS (APCI) |
|---|---|---|---|
| 1.200 | 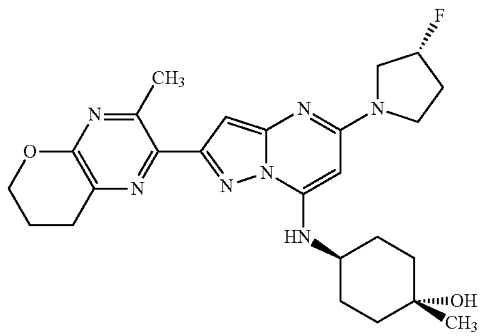 [SMILES: Cc1nc2c(nc1-c1cc3nc(N4CC[C@@H](F)C4)cc(N[C@H]4CC[C@](C)(O)CC4)n3n1)CCCO2] | 3/2*HCl | 482 (M + H) |
| 2.001 | 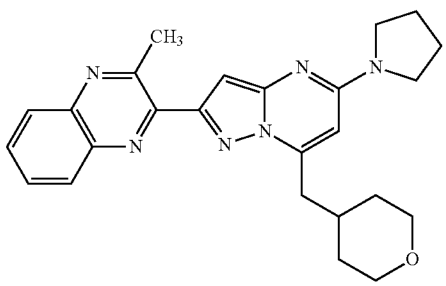 [SMILES: Cc1nc2ccccc2nc1-c1cc2nc(N3CCCC3)cc(CC3CCOCC3)n2n1] | Free form | 429 (M + H) |
| 3.001 | 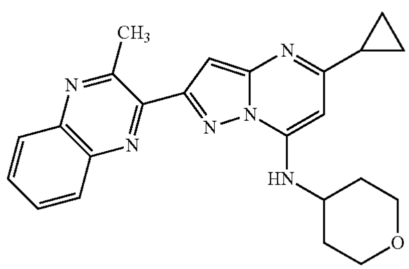 [SMILES: Cc1nc2ccccc2nc1-c1cc2nc(C3CC3)cc(NC3CCOCC3)n2n1] | Free form | 401 (M + H) |
| 4.001 | 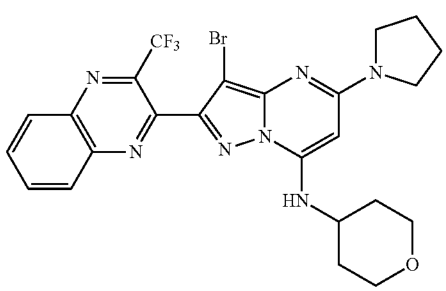 [SMILES: FC(F)(F)c1nc2ccccc2nc1-c1nn2c(NC3CCOCC3)cc(N3CCCC3)nc2c1Br] | Free form | 562/564 (M + H). |
| 4.002 | 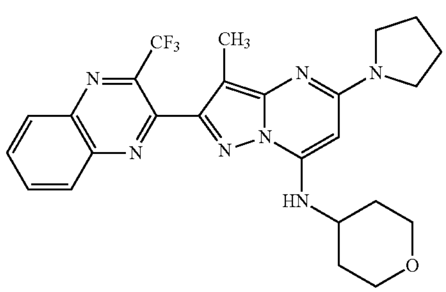 | Free form | 498 (M + H) |

TABLE OF EXAMPLES-continued
| Example | Structure | Salt | MS (APCI) |
|---|---|---|---|
| 4.003 | 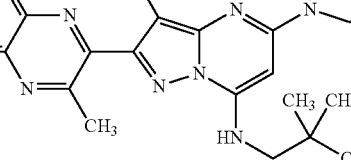 | Free form | 532/534 (M + H) |
| 4.004 | 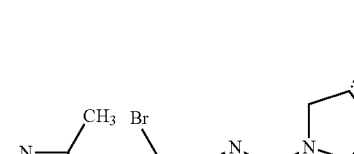 | Free form | 526/528 (M + H) |
| 4.005 | 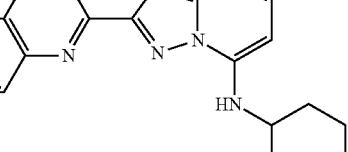 | Free form | 522/524 (M + H) |
| 5.001 | 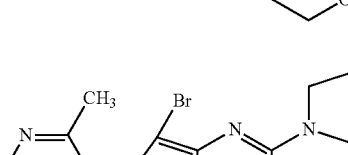 | Free form | 431 (M + H) |
| 5.002 | 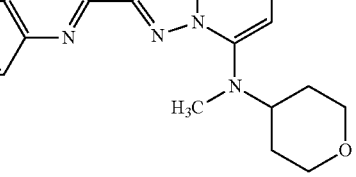 | Free form | 431 (M + H) |

| Reference Example | Structure | Salt | MS (APCI) |
|---|---|---|---|
| 1.01 | 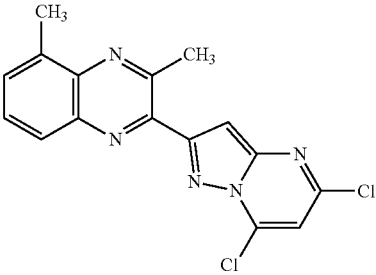 [SMILES: Cc1nc2c(C)cccc2nc1-c1cc2nc(Cl)cc(Cl)n2n1] | Free form | 344/346 (M + H) |
| 1.02 | 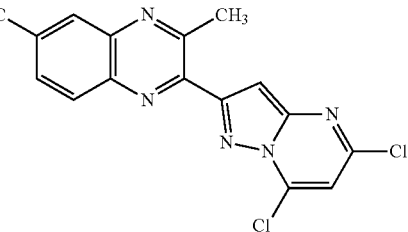 | Free form | 344/346 (M + H) |
| 1.03 | 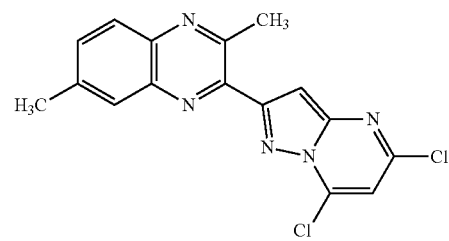 | Free form | 344/346 (M + H) |
| 1.04 | 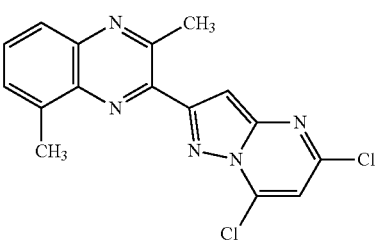 [SMILES: Cc1nc2cccc(C)c2nc1-c1cc2nc(Cl)cc(Cl)n2n1] | Free form | 344/346 (M + H) |
| 1.05 | 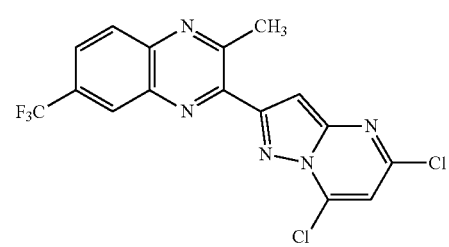 [SMILES: Cc1nc2ccc(C(F)(F)F)cc2nc1-c1cc2nc(Cl)cc(Cl)n2n1] | Free form | 398/400 (M + H) |
| 1.06 | 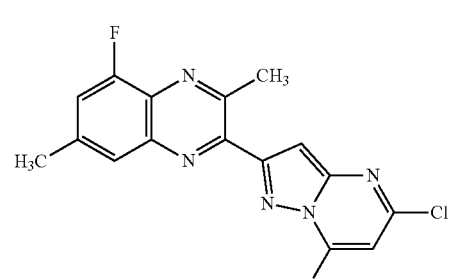 | Free form | 362/364 (M + H) |

-continued

Table of Reference Examples

| Reference Example | Structure | Salt | MS (APCI) |
|---|---|---|---|
| 1.07 | 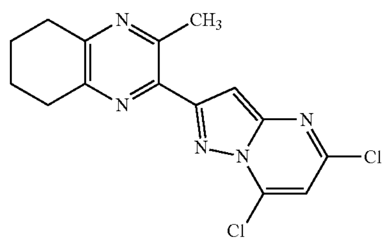 [SMILES: Cc1nc2c(nc1-c1cc3nc(Cl)cc(Cl)n3n1)CCCC2] | Free form | 334/336 (M + H) |
| 1.08 | 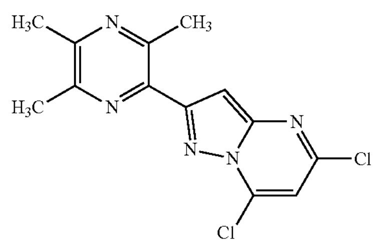 [SMILES: Cc1nc(C)c(-c2cc3nc(Cl)cc(Cl)n3n2)nc1C] | Free form | 308/310 (M + H) |
| 1.09 | 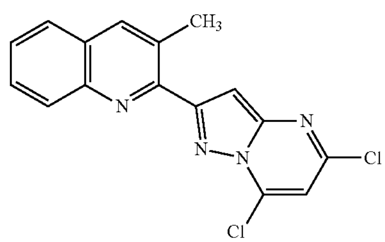 [SMILES: Cc1cc2ccccc2nc1-c1cc2nc(Cl)cc(Cl)n2n1] | Free form | 329/331 (M + H) |
| 1.10 | 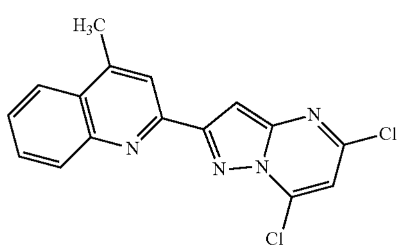 [SMILES: Cc1cc(-c2cc3nc(Cl)cc(Cl)n3n2)nc2ccccc12] | Free form | 329/331 (M + H) |
| 1.11 | 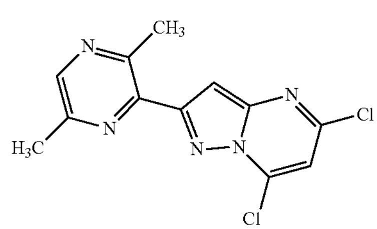 [SMILES: Cc1cnc(C)c(-c2cc3nc(Cl)cc(Cl)n3n2)n1] | Free form | 294/296 (M + H) |
| 1.12 | 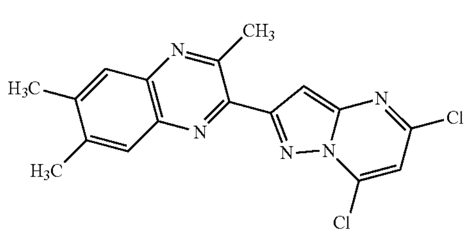 [SMILES: Cc1cc2nc(C)c(-c3cc4nc(Cl)cc(Cl)n4n3)nc2cc1C] | Free form | 358/360 (M + H) |

-continued

| Table of Reference Examples | | | |
|---|---|---|---|
| Reference Example | Structure | Salt | MS (APCI) |
| 1.13 | | Free form | 336/338 (M + H) |
| 1.14 | | Free form | 350/352 (M + H) |
| 1.15 | | Free form | 322/324 (M + H) |
| 1.16 | | Free form | 334/336 (M + H) |
| 1.17 | | Free form | 322/324 (M + H) |
| 1.18 | | Free form | 319/321 (M + H) |

The invention claimed is:
1. A compound represented by formula [I]:

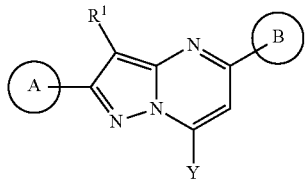

wherein:
R¹ is hydrogen, halogen, lower alkyl or cyano;
Ring A is an optionally substituted heterocyclic group;
Ring B is an optionally substituted 3 to 6-membered monocyclic group; and
Y is optionally substituted amino,
optionally substituted cyclic amino,
optionally substituted aliphatic 3 to 6-membered monocyclyloxy,
optionally substituted lower alkyl or
optionally substituted lower alkyl-O—,
or a pharmaceutically acceptable salt thereof.

2. The compound of claim 1 or a pharmaceutically acceptable salt thereof, wherein Y is optionally substituted amino.

3. The compound of claim 1 or a pharmaceutically acceptable salt thereof, wherein
Y is represented by formula [III]:

 —Z—R²  [III]

wherein:
Z is —N(R³)—, —O— or $C_{1-2}$ alkylene;
R³ is hydrogen; lower alkyl optionally substituted by 1 to 2 substituent(s) which are the same or different and selected from hydroxy and lower alkoxy; or lower cycloalkyl; and
R² is
(1) lower alkyl optionally substituted by 1 to 3 substituent(s) which are the same or different and selected from the group consisting of hydroxy, halogen, cyano, lower alkoxy, lower cycloalkyl, hydroxy-substituted lower cycloalkyl, halo-lower alkyl and mono- or di-lower alkyl amino; or
(2) an optionally substituted aliphatic 3 to 6-membered monocyclic group.

4. The compound of claim 3 or a pharmaceutically acceptable salt thereof, wherein
the "optionally substituted heterocyclic group" represented by Ring A is a heterocyclic group optionally substituted by 1 to 6 substituent(s) which are the same or different and selected from the group consisting of lower alkyl; lower cycloalkyl; halogen; halo-lower alkyl; hydroxy; lower-alkoxy; halo-lower alkoxy; amino optionally substituted by 1 to 2 substituent(s) which are the same or different and selected from lower-alkyl and halogen; and cyclic amino optionally substituted by 1 to 3 substituent(s) which are the same or different and selected from lower-alkyl and halogen,
and,
the "optionally substituted 3 to 6-membered monocyclic group" represented by Ring B is a 3 to 6-membered monocyclic group optionally substituted by 1 to 3 substituent(s) which are same or different and selected from the group consisting of halogen; oxo; hydroxy; lower alkyl optionally substituted by 1 to 2 substituent(s) which are the same or different and selected from hydroxy and lower alkoxy; lower alkoxy; lower alkylsulfonyloxy; and amino optionally substituted by 1 to 2 substituent(s) which are the same or different and selected from lower alkyl,
and,
the "optionally substituted aliphatic 3 to 6-membered monocyclic group" represented by R² is an aliphatic 3 to 6-membered monocyclic group optionally substituted by 1 to 3 substituent(s) which are the same or different and selected from the group consisting of halogen; oxo; hydroxy; lower alkanoyl; lower alkoxy; and lower alkyl optionally substituted by 1 to 2 substituent(s) which are the same or different and selected from hydroxy and lower alkoxy.

5. The compound of claim 3, or a pharmaceutically acceptable salt thereof, wherein
the heterocyclic moiety in the "optionally substituted heterocyclic group" represented by Ring A is monocyclic or bicylic heteroaryl containing 1 to 3 nitrogen atoms as a hetero atom or a group having an aliphatic 5 to 6-membered ring fused thereon;
and,
the monocycle moiety in the "optionally substituted 3 to 6-membered monocyclic group" represented by Ring B is a 4 to 6-membered monocyclic nitrogen-containing heterocyclic group or 3 to 6-membered monocyclic hydrocarbon group,
and,
the monocycle moiety in the "optionally substituted aliphatic 3 to 6-membered monocyclic group" represented by R² is
4 to 6-membered aliphatic monocyclic heterocyclic group containing 1 to 2 hetero atom(s) selected from oxygen atom, nitrogen atom and sulfur atom; or
$C_{3-6}$ cycloalkyl.

6. The compound of claim 3, or a pharmaceutically acceptable salt thereof, wherein
the heterocyclic moiety in the "optionally substituted heterocyclic group" represented by Ring A is selected from the group consisting of pyridyl, pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl and pyrazolo[1,5-a]pyrimidinyl,
and,
the monocycle moiety in the "optionally substituted 3 to 6-membered monocyclic group" represented by Ring B is selected from the group consisting of pyrrolidinyl, azetidinyl, imidazolidinyl, pyrazolidinyl, piperidinyl, piperazinyl, morpholinyl, thiomorpholinyl and $C_{3-6}$ cycloalkyl, or unsaturated monocyclic group thereof;
and,
the monocycle moiety in the "optionally substituted aliphatic 3 to 6-membered monocyclic group" represented by R² is selected from the group consisting of tetrahydropyranyl, tetrahydrofuranyl, oxetanyl, tetrahydrothiopyranyl, tetrahydrothienyl, thietanyl, piperidyl, and $C_{3-6}$ cycloalkyl.

7. The compound of claim 3, or a pharmaceutically acceptable salt thereof, wherein
the heterocyclic moiety in the "optionally substituted heterocyclic group" represented by Ring A is selected from the group consisting of pyridin-2-yl, pyrazin-2-yl, quinolin-2-yl, quinoxalin-2-yl, 5,6,7,8-tetrahydroquinoxalin-2-yl, 7,8-dihydro-6H-pyrano[2,3-b]pyrano-2-yl, 7,8-dihydro-6H-pyrano[2,3-b]pyrazin-3-yl, pyrido[3,4-b]pyrazin-2-yl and pyrido[3,4-b]pyrazin-3-yl, and,
the monocycle moiety in the "optionally substituted 3 to 6-membered monocyclic group" represented by Ring B is selected from the group consisting of 1-pyrrolidinyl, 1-azetidinyl, 1-pyrazolidinyl, cyclopentyl and cyclopentenyl,
and,
the monocycle moiety in the "optionally substituted aliphatic 3 to 6-membered monocyclic group" represented by $R^2$ is selected from the group consisting of 3- or 4-tetrahydropyranyl, 3-tetrahydrofuranyl, 3-oxetanyl, 3- or 4-tetrahydrothiopyranyl, 3-tetrahydrothienyl, 3-thietanyl, 4-piperidyl, and $C_{3-6}$ cycloalkyl.

8. The compound of claim 3 or a pharmaceutically acceptable salt thereof, wherein
Ring A is pyrazinyl, quinolyl, quinoxalinyl, 5,6,7,8-tetrahydroquinoxalinyl, 7,8-dihydro-6H-pyrano[2,3-b]pyrazinyl, pyrido[3,4-b]pyrazinyl and pyrazolo[1,5-a]pyrimidinyl, each of which is optionally substituted by 1 to 3 substituent(s) which are the same or different and selected from the group consisting of lower alkyl; lower cycloalkyl; halogen; halo-lower alkyl; and cyclic amino optionally substituted by 1 to 3 substituent(s) which are the same or different and selected from lower-alkyl and halogen,
and,
Ring B is 1-pyrrolidinyl, 1-azetidinyl, 1-pyrazolyl, cyclopropyl, cyclopentyl, or cyclopenten-1-yl, each of which is optionally substituted by 1 to 3 substituent(s) which are the same or different and selected from the group consisting of halogen; hydroxy; lower alkyl optionally substituted by 1 to 2 substituent(s) which are the same or different and selected from hydroxy, lower alkoxy,
and,
$R^2$ is
(1) lower alkyl optionally substituted by 1 to 3 substituent(s) which are the same or different and selected from the group consisting of hydroxy, halogen, cyano, lower alkoxy, hydroxy-substituted lower cycloalkyl, halolower alkyl and mono- or di-lower alkyl amino; or
(2) 3- or 4-tetrahydropyranyl, 3-tetrahydrofuranyl, 3-oxetanyl, 3-tetrahydrothienyl, 4-piperidyl, or $C_{3-6}$cycloalkyl, each of which is optionally substituted by 1 to 3 substituent(s) which are the same or different and selected from the group consisting of halogen; oxo; hydroxy; lower alkanoyl; lower alkoxy; and lower alkyl optionally substituted by 1 to 2 substituent(s) which are the same or different and selected from hydroxy and lower alkoxy,
and,
$R^3$ is hydrogen.

9. The compound of claim 8 or a pharmaceutically acceptable salt thereof, wherein
Ring A is pyrazin-2-yl and quinoxalin-2-yl, each of which is optionally substituted by 1 to 3 substituent(s) which are the same or different and selected from the group consisting of lower alkyl, and halogen,
Ring B is 1-pyrrolidinyl which is optionally substituted by 1 to 3 substituent(s) which are the same or different and selected from the group consisting of halogen; hydroxy; lower alkyl optionally substituted by 1 to 2 substituent(s) which are the same or different and selected from hydroxy, lower alkoxy.

10. The compound of claim 1 or a pharmaceutically acceptable salt thereof, wherein $R^1$ is hydrogen.

11. The compound of claim 1 or a pharmaceutically acceptable salt thereof, wherein $R^1$ is hydrogen, and, Z is —N($R^3$)—.

12. The compound of claim 1 or a pharmaceutically acceptable salt thereof, selected from the group consisting of
2-(3-methylquinoxalin-2-yl)-5-pyrrolidin-1-yl-N-(tetrahydro-2H-pyran-4-yl)pyrazolo[1,5-a]pyrimidin-7-amine;
N-Methyl-2-(3-methylquinoxalin-2-yl)-5-pyrrolidin-1-yl-N-(tetrahydro-2H-pyran-4-yl)pyrazolo[1,5-a]pyrimidin-7-amine;
5-[(3R)-3-fluoropyrrolidin-1-yl]-2-(3-methylquinoxalin-2-yl)-N-(tetrahydro-2H-pyran-4-yl)pyrazolo[1,5-a]pyrimidin-7-amine;
1-({2-(7-fluoro-3-methylquinoxalin-2-yl)-5-[(3R)-3-fluoropyrrolidin-1-yl]pyrazolo[1,5-a]pyrimidin-7-yl}amino)-2-methylpropan-2-ol;
5-(2,5-dihydro-1H-pyrrol-1-yl)-2-(3-methylquinoxalin-2-yl)-N-(tetrahydro-2H-pyran-4-yl)pyrazolo[1,5-a]pyrimidin-7-amine;
2-methyl-3-[5-pyrrolidin-1-yl-7-(tetrahydro-2H-pyran-4-yloxy)pyrazolo[1,5-a]pyrimidin-2-yl]quinoxaline;
5-cyclopent-1-en-1-yl-2-(3-methylquinoxalin-2-yl)-N-(tetrahydro-2H-pyran-4-yl)pyrazolo[1,5-a]pyrimidin-7-amine;
trans-4-({2-(7-fluoro-3-methylquinoxalin-2-yl)-5-[(3R)-3-fluoropyrrolidin-1-yl]pyrazolo[1,5-a]pyrimidin-7-yl}amino)-1-methylcyclohexanol;
2-(5,7-dipyrrolidin-1-ylpyrazolo[1,5-a]pyrimidin-2-yl)-3-methylquinoxaline;
(2S)-1,1,1-trifluoro-3-{[2-(3-methylquinoxalin-2-yl)-5-pyrrolidin-1-ylpyrazolo[1,5-a]pyrimidin-7-yl]amino}propan-2-ol;
3-{[2-(3-methylquinoxalin-2-yl)-5-pyrrolidin-1-ylpyrazolo[1,5-a]pyrimidin-7-yl]amino}propanenitrile;
N-(trans-4-methoxycyclohexyl)-2-[3-methyl-7-(trifluoromethyl)quinoxalin-2-yl]-5-pyrrolidin-1-ylpyrazolo[1,5-a]pyrimidin-7-amine;
2-(3,7-dimethylquinoxalin-2-yl)-N,N-bis(2-methoxyethyl)-5-pyrrolidin-1-ylpyrazolo[1,5-a]pyrimidin-7-amine;
5-[(3R)-3-fluoropyrrolidin-1-yl]-2-(3-methylquinoxalin-2-yl)-N-oxetan-3-ylpyrazolo[1,5-a]pyrimidin-7-amine;
1-{[5-[(3R)-3-fluoropyrrolidin-1-yl]-2-(3-methylquinoxalin-2-yl)pyrazolo[1,5-a]pyrimidin-7-yl]amino}-2-methylpropan-2-ol;
N-cyclopropyl-5-[(3R)-3-fluoropyrrolidin-1-yl]-2-(3-methylquinoxalin-2-yl)pyrazolo[1,5-a]pyrimidin-7-amine;
2-(3-ethylquinoxalin-2-yl)-5-[(3R)-3-fluoropyrrolidin-1-yl]-N-(trans-4-methoxycyclohexyl)pyrazolo[1,5-a]pyrimidin-7-amine;
trans-4-({5-[(3R)-3-fluoropyrrolidin-1-yl]-2-[3-(trifluoromethyl)quinoxalin-2-yl]pyrazolo[1,5-a]pyrimidin-7-yl}amino)-1-methylcyclohexanol;
(1S,2S)-2-{[2-(7-fluoro-3-methylquinoxalin-2-yl)-5-pyrrolidin-1-ylpyrazolo[1,5-a]pyrimidin-7-yl]amino}cyclohexanol;
2-(3,5-dimethylquinoxalin-2-yl)-5-pyrrolidin-1-yl-N-(tetrahydro-2H-pyran-4-yl)pyrazolo[1,5-a]pyrimidin-7-amine;
2-(3,6-dimethylquinoxalin-2-yl)-5-pyrrolidin-1-yl-N-(tetrahydro-2H-pyran-4-yl)pyrazolo[1,5-a]pyrimidin-7-amine;
2-(3,7-dimethylquinoxalin-2-yl)-N-[(3R)-1,1-dioxidotetrahydro-3-thienyl]-5-pyrrolidin-1-ylpyrazolo[1,5-a]pyrimidin-7-amine;

N-(1-acetylpiperidin-4-yl)-2-(3,7-dimethylquinoxalin-2-yl)-5-pyrrolidin-1-ylpyrazolo[1,5-a]pyrimidin-7-amine;

2-(3,7-dimethylquinoxalin-2-yl)-N-(1-propylpiperidin-4-yl)-5-pyrrolidin-1-ylpyrazolo[1,5-a]pyrimidin-7-amine;

N'-[2-(3,7-dimethylquinoxalin-2-yl)-5-pyrrolidin-1-ylpyrazolo[1,5-a]pyrimidin-7-yl]-N,N-dimethyl-ethane-1,2-diamine;

N-(4,4-difluorocyclohexyl)-2-(3-methyl-5,6,7,8-tetrahydroquinoxalin-2-yl)-5-pyrrolidin-1-ylpyrazolo[1,5-a]pyrimidin-7-amine;

N-methyl-5-pyrrolidin-1-yl-N-(tetrahydro-2H-pyran-4-yl)-2-(3,5,6-trimethylpyrazin-2-yl)pyrazolo[1,5-a]pyrimidin-7-amine;

((2S)-1-{2-(3-methylquinoxalin-2-yl)-7-[(3R)-tetrahydro-2H-pyran-3-ylamino]pyrazolo[1,5-a]pyrimidin-5-yl}pyrrolidin-2-yl)methanol;

{(2S)-1-[7-[cyclopropyl(tetrahydro-2H-pyran-4-yl)amino]-2-(3,7-dimethylquinoxalin-2-yl)pyrazolo[1,5-a]pyrimidin-5-yl]pyrrolidin-2-yl}methanol;

1-[2-(3,7-dimethylquinoxalin-2-yl)-7-(tetrahydro-2H-pyran-4-ylamino)pyrazolo[1,5-a]pyrimidin-5-yl]azetidin-3-ol;

2-methyl-3-[5-pyrrolidin-1-yl-7-(tetrahydro-2H-pyran-4-ylmethyl)pyrazolo[1,5-a]pyrimidin-2-yl]quinoxaline;

trans-1-methyl-4-{[2-(3-methyl-7,8-dihydro-6H-pyrano[2,3-b]pyrazin-2-yl)-5-pyrrolidin-1-ylpyrazolo[1,5-a]pyrimidin-7-yl]amino}cyclohexanol;

cis-4-({2-(7-fluoro-3-methylquinoxalin-2-yl)-5-[(3R)-3-fluoropyrrolidin-1-yl]pyrazolo[1,5-a]pyrimidin-7-yl}amino)-1-methylcyclohexanol;

N-methyl-2-(3-methyl-6-propylpyrazin-2-yl)-5-pyrrolidin-1-yl-N-(tetrahydro-2H-pyran-4-yl)pyrazolo[1,5-a]pyrimidin-7-amine;

2-methyl-1-[(6'-methyl-5-pyrrolidin-1-yl-2,5'-bipyrazolo[1,5-a]pyrimidin-7-yl)amino]propan-2-ol;

1-{[2-(6-isobutyl-3,5-dimethylpyrazin-2-yl)-5-pyrrolidin-1-ylpyrazolo[1,5-a]pyrimidin-7-yl]amino}-2-methylpropan-2-ol;

1-{[2-(6-cyclopropyl-3,5-dimethylpyrazin-2-yl)-5-pyrrolidin-1-ylpyrazolo[1,5-a]pyrimidin-7-yl]amino}-2-methylpropan-2-ol;

2-(6-cyclopropyl-3,5-dimethylpyrazin-2-yl)-5-pyrrolidin-1-yl-N-(tetrahydro-2H-pyran-4-yl)pyrazolo[1,5-a]pyrimidin-7-amine;

2-(3-methyl-7,8-dihydro-6H-pyrano[2,3-b]pyrazin-2-yl)-5-pyrrolidin-1-yl-N-(tetrahydro-2H-pyran-4-yl)pyrazolo[1,5-a]pyrimidin-7-amine;

2-methyl-1-{[2-(3-methyl-7,8-dihydro-6H-pyrano[2,3-b]pyrazin-2-yl)-5-pyrrolidin-1-ylpyrazolo[1,5-a]pyrimidin-7-yl]amino}propan-2-ol;

N-(trans-4-methoxycyclohexyl)-2-(3-methyl-7,8-dihydro-6H-pyrano[2,3-b]pyrazin-2-yl)-5-pyrrolidin-1-ylpyrazolo[1,5-a]pyrimidin-7-amine;

2-(2-methylpyrido[3,4-b]pyrazin-3-yl)-5-pyrrolidin-1-yl-N-(tetrahydro-2H-pyran-4-yl)pyrazolo[1,5-a]pyrimidin-7-amine; and 2-(3-methylpyrido[3,4-b]pyrazin-2-yl)-5-pyrrolidin-1-yl-N-(tetrahydro-2H-pyran-4-yl)pyrazolo[1,5-a]pyrimidin-7-amine.

13. A method of treating schizophrenia, anxiety disorder, drug addiction, a disease comprising as a symptom a deficiency in cognition, mood disorder or mood episode, comprising administering to the patient an effective amount of the compound of claim 1 or a pharmaceutically acceptable salt thereof.

14. A pharmaceutical composition comprising the compound of claim 1 or a pharmaceutically acceptable salt thereof and a pharmaceutically acceptable carrier or diluent.

* * * * *